(12) United States Patent
Menon et al.

(10) Patent No.: US 9,131,697 B2
(45) Date of Patent: Sep. 15, 2015

(54) SPIROCYCLIC ISOXAZOLINES AS ANTIPARASITIC AGENTS

(71) Applicant: Zoetis Services LLC, Florham Park, NJ (US)

(72) Inventors: Sanjay Menon, Kalamazoo, MI (US); Susan M. K. Sheehan, Kalamazoo, MI (US); Valerie A. Vaillancourt, Kalamazoo, MI (US)

(73) Assignee: Zoetis Services LLC, Florham Park, NJ (US)

(*) Notice: Subject to any disclaimer, the term of this patent is extended or adjusted under 35 U.S.C. 154(b) by 0 days.

(21) Appl. No.: 14/423,951

(22) PCT Filed: Sep. 4, 2013

(86) PCT No.: PCT/US2013/057935
§ 371 (c)(1),
(2) Date: Feb. 25, 2015

(87) PCT Pub. No.: WO2014/039484
PCT Pub. Date: Mar. 13, 2014

(65) Prior Publication Data
US 2015/0181882 A1 Jul. 2, 2015

Related U.S. Application Data

(60) Provisional application No. 61/698,004, filed on Sep. 7, 2012.

(51) Int. Cl.
| | |
|---|---|
| C07D 491/20 | (2006.01) |
| C07D 495/20 | (2006.01) |
| C07D 491/107 | (2006.01) |
| C07D 495/10 | (2006.01) |
| A01N 43/90 | (2006.01) |

(52) U.S. Cl.
CPC .............. *A01N 43/90* (2013.01); *C07D 491/20* (2013.01); *C07D 495/10* (2013.01)

(58) Field of Classification Search
None
See application file for complete search history.

(56) References Cited

U.S. PATENT DOCUMENTS

| | | | |
|---|---|---|---|
| 8,415,310 B2 | 4/2013 | Vaillancourt et al. | |
| 8,466,115 B2 * | 6/2013 | Curtis et al. | 514/30 |
| 2011/0166193 A1 | 7/2011 | Renold et al. | |

FOREIGN PATENT DOCUMENTS

| | | |
|---|---|---|
| WO | 2010/025998 | 3/2010 |
| WO | 2012/017359 | 2/2012 |
| WO | 2012/120399 | 9/2012 |

OTHER PUBLICATIONS

PCT International Search Report, PCT/US2013/057935 filed Sep. 4, 2013 (3 pages).

* cited by examiner

*Primary Examiner* — Michael Barker
(74) *Attorney, Agent, or Firm* — Paul M. Misiak

(57) ABSTRACT

The invention recites spirocyclic isoxazoline derivatives of Formula (1) stereoisomers thereof, veterinary or pharmaceutical acceptable salts thereof, compositions thereof, processes for making, and their use as a parasiticide in an animal. The variables $W^1$, $W^2$, $W^3$, W, X, $R^{1a}$, $R^{1b}$, $R^{1c}$, $R^2$, $R^3$, $R^4$, and n are as described herein.

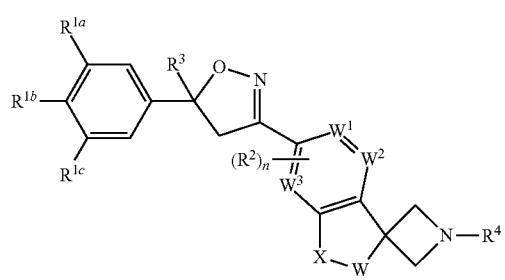

(1)

19 Claims, No Drawings

SPIROCYCLIC ISOXAZOLINES AS ANTIPARASITIC AGENTS

CROSS-REFERENCE TO RELATED APPLICATIONS

This application is a 371 filing of International Application No. PCT/US2013/057935 filed Sep. 4, 2013, now pending, which claims the benefit of U.S. Provisional Application 61/698,004 filed Sep. 7, 2012.

FIELD OF THE INVENTION

This invention relates to spirocyclic isoxazoline derivatives having parasiticidal activity. The compounds of interest are spirocyclic isoxazoline derivatives with an azetidine moiety. The invention also relates to processes of making said spirocyclic isoxazoline derivatives, compositions and methods of use thereof.

BACKGROUND

There is a need for improved antiparasitic agents for use with animals, and in particular there is a need for improved insecticides and acaricides. Furthermore there is a need for improved topical and oral products with convenient administration and which contain one or more of such antiparasitic agents which can be used to effectively treat ectoparasites, such as insects (e.g., fleas, lice, and flies) and acarids (e.g., mites and ticks). Such products would be particularly useful for the treatment of animals including: birds (e.g., chickens and turkeys), fish, companion animals (e.g., cats, dogs, llamas, and horses), and livestock (e.g., cattle, bison, swine, sheep, deer, elk, and goats). The compounds of the instant invention would also be particularly useful as an insecticide for plants.

The compounds currently available for insecticidal and acaricidal treatment of animals do not always demonstrate good activity, good speed of action, or a long duration of action. Most treatments contain hazardous chemicals that can have serious consequences, including neurotoxicity and lethality from accidental ingestion. Persons applying these agents are generally advised to limit their exposure. Pet collars and tags have been utilized to overcome some problems, but these are susceptible to chewing, ingestion, and subsequent toxicological affects to the animal. Thus, current treatments achieve varying degrees of success which depend partly on toxicity, method of administration, and efficacy. Currently, some agents are actually becoming ineffective due to parasitic resistance.

Isoxazoline derivatives have been disclosed in the art as having insecticidal and acaricidal activity. For example, WO2007/105814, WO2008/122375, and WO2009/035004 recite certain alkylene linked amides. WO2010/032437 discloses that the benzyl amide can be moved to the position ortho to the isoxazoline. Further, WO2007/075459 discloses phenyl isoxazolines substituted with 5- to 6-membered heterocycles, and WO2010/084067 and WO2010/025998 disclose phenyl isoxazolines substituted with 10- to 11-membered fused aryl and heteroaryls. Chiral processes for manufacturing isoxazolines have been reported in WO2011/104089 and WO2009/063910. Some spiro-azetidine isobenzofuran derivatives for the treatment of diabetes and hyperlipidemia were described in WO2008/096746. Spirocyclic azetidines were published in WO2012/017359. In addition, spiroisoxazolines were recently filed in PCT/IB2012/050842. However, none of these citations exemplify pyridyl spirocyclic substituted isoxazolines, or processes of manufacturing the same, nor does the prior art indicate that such compounds would be useful against a spectrum of parasitic species relevant to companion animals, livestock or fowl against the range of parasitic morphological lifecycle stages.

Despite the availability of effective, broad spectrum antiparasitic agents, there remains a need for a safer, convenient, efficacious, and environmentally friendly product that will overcome the ever-present threat of resistance development.

The present invention overcomes one or more of the various disadvantages of, or improves upon, the properties of existing compounds. In particular the present invention develops new spirocyclic isoxazoline substituted azetidine compounds which demonstrate such properties.

SUMMARY

The present invention provides Formula (1) compounds, stereoisomers thereof, veterinary or pharmaceutically acceptable salts thereof, which act as parasiticides, in particular, ectoparasiticides; therefore may be used to prevent, treat, repel, and control acarids and insect infection and infestation in animals. In addition, the invention contemplates the control and prevention of tick borne diseases, for example, Lyme disease, canine and bovine anaplasmosis, canine ehrlichiosis, canine rickettsiosis, canine and bovine babesiosis, epizootic bovine abortion, and theileriosis. Thus, according to the invention, there is provided a compound of Formula (1)

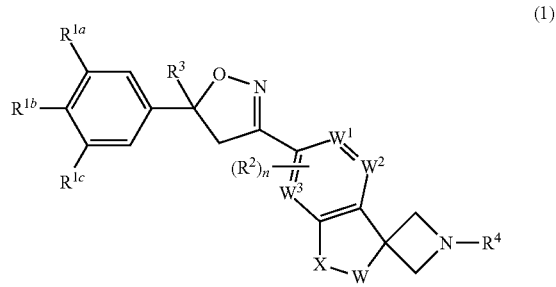

(1)

wherein $W^1$, $W^2$, and $W^3$ are each independently C or N;

X is —S(O)$_p$ or O and W is CH$_2$, or W is —S(O)$_p$ or O and X is CH$_2$; with the proviso that if W or X is O then one of $W^1$, $W^2$, and $W^3$ is N and if $W^1$, $W^2$, and $W^3$ are all C then one of X or W is —S(O)$_p$;

$R^{1a}$, $R^{1b}$, and $R^{1c}$ are each independently hydrogen, halo, cyano, hydroxyl, nitro, C$_1$-C$_6$alkyl, C$_1$-C$_6$haloalkyl, C$_1$-C$_6$alkoxy, C$_0$-C$_3$alkylC$_3$-C$_6$ cycloalkyl, C$_1$-C$_6$haloalkoxy, —C(O)NH$_2$, —SF$_5$, or —S(O)$_p$R;

$R^2$ is halo, cyano, C$_1$-C$_6$alkyl, C$_1$-C$_6$haloalkyl, nitro, hydroxyl, —C(O)NR$^a$R$^b$, C$_2$-C$_6$alkenyl, C$_2$-C$_6$alkynyl, —S(O)$_p$R, or —OR;

$R^3$ is cyano, C$_1$-C$_6$alkyl, C$_1$-C$_6$haloalkyl, —C(O)NR$^a$R$^b$, C$_2$-C$_6$alkenyl, C$_2$-C$_6$alkynyl, C$_2$-C$_6$haloalkenyl, or C$_2$-C$_6$haloalkynyl;

$R^4$ is hydrogen, C$_1$-C$_6$alkyl, C$_0$-C$_6$alkylC$_3$-C$_6$cycloalkyl, —C(O)R$^5$, —C(S)R$^5$, —C(O)NR$^a$R$^5$, —C(O)C(O)NR$^a$R$^5$, —S(O)$_p$R$^c$, —S(O)$_2$NR$^a$R$^5$, —C(NR$^6$)R$^5$, —C(NR$^6$)NR$^a$R$^5$, C$_0$-C$_6$alkylphenyl, C$_0$-C$_6$alkylheteroaryl, or C$_0$-C$_6$alkylheterocycle;

$R^5$ is hydrogen, C$_1$-C$_6$alkyl, C$_2$-C$_6$alkenyl, C$_0$-C$_6$alkylC$_3$-C$_6$cycloalkyl, C$_0$-C$_6$alkylphenyl, C$_0$-C$_6$alkylheteroaryl, or C$_0$-C$_6$alkylheterocycle;

R⁶ is hydrogen, $C_1$-$C_6$alkyl, hydroxyl, cyano, nitro, —S(O)$_p$R$^c$, or $C_1$-$C_6$alkoxy;

R is $C_1$-$C_6$alkyl or $C_3$-$C_6$cycloalkyl optionally substituted with at least one halo substituent;

R$^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

R$^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

R$^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R, —SCN, or —C(O)NR$^a$R$^b$;

each of R⁴ and R⁵ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, —S(O)$_p$R$^c$, —SH, —S(O)$_p$NR$^a$R$^b$, —NR$^a$R$^b$, —NR$^a$C(O)R$^b$, —SC(O)R, —SCN, or —C(O)NR$^a$R$^b$; and wherein each of R⁴ and R⁵ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =NR⁶, hydroxyl, $C_1$-$C_6$alkoxy, $C_1$-$C_6$alkyl, hydroxyl$C_1$-$C_6$alkyl-, $C_1$-$C_6$haloalkyl, —SH, —S(O)$_p$R, and $C_1$-$C_6$haloalkoxy;

n is the integer 0, 1, or 2, and when n is 2, each R² may be identical or different from each other; and p is the integer 0, 1, or 2;

stereoisomers thereof, and veterinary or pharmaceutical acceptable salts thereof.

In another aspect of the invention are compounds of Formula (1.1), (1.2), (1.3), and (1.4) of Formula (1)

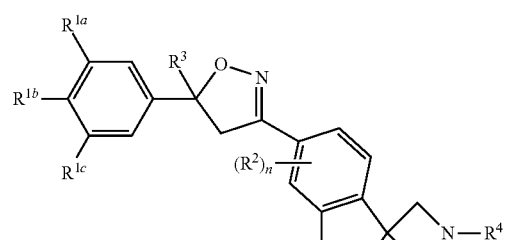
(1.1)

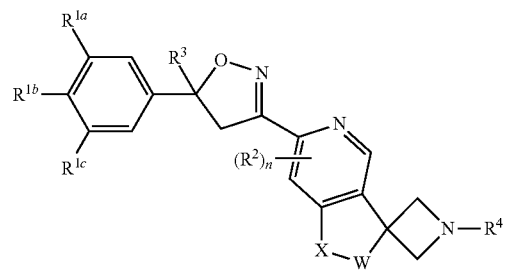
(1.2)

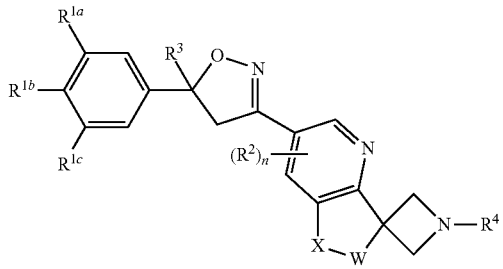
(1.3)

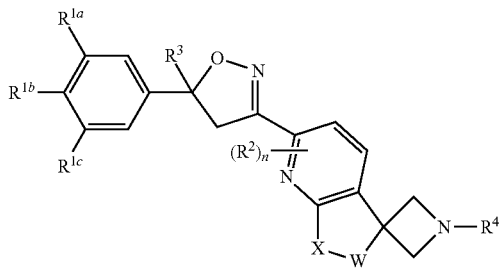
(1.4)

wherein R$^{1a}$, R$^{1b}$, R$^{1c}$, R², R³, R⁴, X, W, and n are as defined above, stereoisomers thereof, and veterinary or pharmaceutical acceptable salts thereof.

In another aspect of the invention are compounds of Formula (1.1a) or (1.1b)

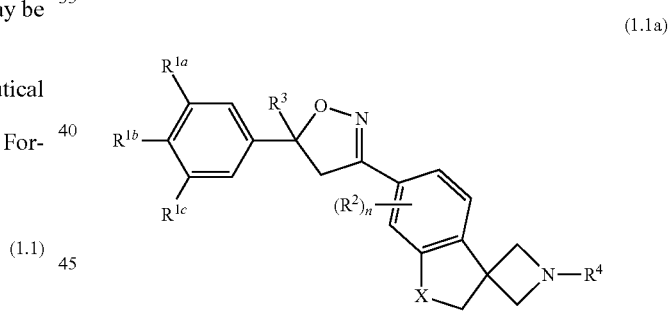
(1.1a)

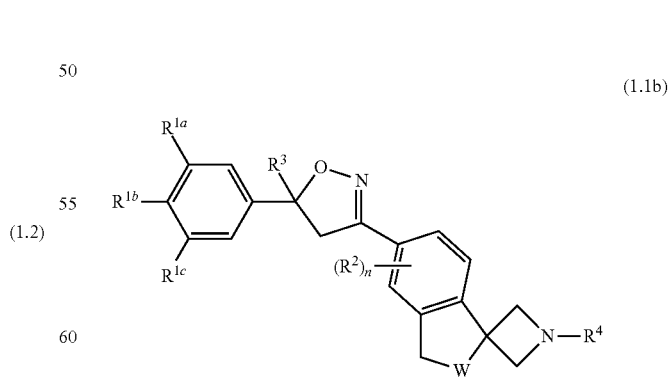
(1.1b)

wherein R$^{1a}$, R$^{1b}$, R$^{1c}$, R², R³, R⁴, and n are as defined above, and X and W are each —S(O)$_p$, wherein p is as defined above, stereoisomers thereof, and veterinary or pharmaceutical acceptable salts thereof.

In another aspect of the invention are compounds of Formula (1.2a) or (1.2b)

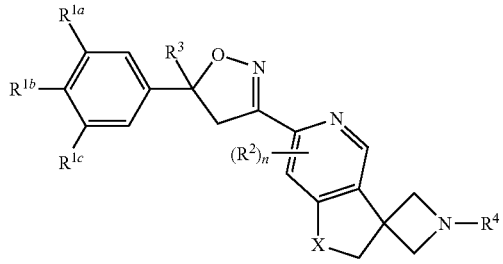
(1.2a)

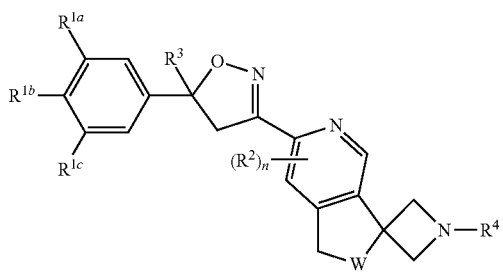
(1.2b)

wherein $R^{1a}$, $R^{1b}$, $R^{1c}$, $R^2$, $R^3$, $R^4$, and n are as defined above, and X and W are each O, stereoisomers thereof, and veterinary or pharmaceutical acceptable salts thereof.

In another aspect of the invention are compounds of Formula (1.2a) or (1.2b) wherein $R^{1a}$, $R^{1b}$, $R^{1c}$, $R^2$, $R^3$, $R^4$, and n are as defined above, and X and W are each —S(O)$_p$, wherein p is as defined above, stereoisomers thereof, and veterinary or pharmaceutical acceptable salts thereof.

In another aspect of the invention are compounds of Formula (1.3a) or (1.3b)

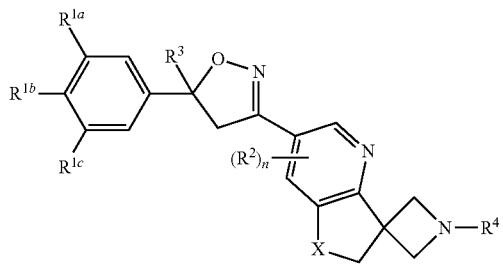
(1.3a)

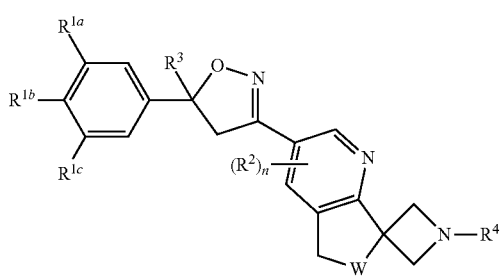
(1.3b)

wherein $R^{1a}$, $R^{1b}$, $R^{1c}$, $R^2$, $R^3$, $R^4$, and n are as defined above, and X and W are each O, stereoisomers thereof, and veterinary or pharmaceutical acceptable salts thereof.

In another aspect of the invention are compounds of Formula (1.3a) or (1.3b) wherein $R^{1a}$, $R^{1b}$, $R^{1c}$, $R^2$, $R^3$, $R^4$, and n are as defined above, and X and W are each —S(O)$_p$, wherein p is as defined above, stereoisomers thereof, and veterinary or pharmaceutical acceptable salts thereof.

In another aspect of the invention are compounds of Formula (1.4a) or (1.4b)

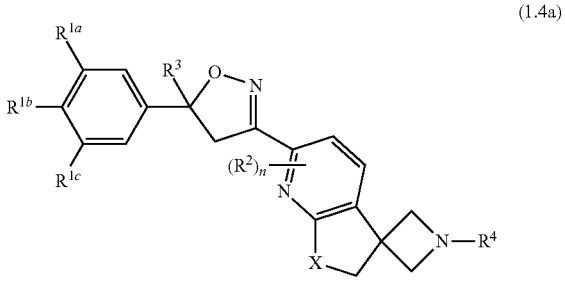
(1.4a)

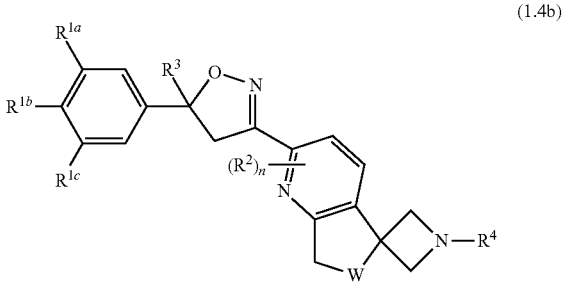
(1.4b)

wherein $R^{1a}$, $R^{1b}$, $R^{1c}$, $R^2$, $R^3$, $R^4$, and n are as defined above, and X and W are each O, stereoisomers thereof, and veterinary or pharmaceutical acceptable salts thereof.

In another aspect of the invention are compounds of Formula (1.4a) or (1.4b) wherein $R^{1a}$, $R^{1b}$, $R^{1c}$, $R^2$, $R^3$, $R^4$, and n are as defined above, and X and W are each —S(O)$_p$, wherein p is as defined above, stereoisomers thereof, and veterinary or pharmaceutical acceptable salts thereof.

In yet another aspect of the invention are compounds of Formula (1) selected from the group consisting of:
3'-[5-(3,5-dichlorophenyl)-5-(trifluoromethyl)-4,5-dihydroisoxazol-3-yl]-1-[(methylsulfonyl)acetyl]-5'H-spiro[azetidin-3,7'-furo[3,4,b]pyridine];
3'-[5-(3,5-dichloro-4-fluorophenyl)-5-(trifluoromethyl)-4,5-dihydroisoxazol-3-yl]-1-[(methylsulfonyl)acetyl]-5'H-spiro[azetidin-3,7'-furo[3,4,b]pyridine];
1-[(methylsulfonyl)acetyl]-3'-[5-(3,4,5-trichlorophenyl)-5-(trifluoromethyl)-4,5-dihydroisoxazol-3-yl]-5'H-spiro[azetidin-3,7'-furo[3,4,b]pyridine];
3'-[5-(3,5-dichloro-4-fluorophenyl)-5-(trifluoromethyl)-4,5-dihydroisoxazol-3-yl]-1-isobutyryl-5'H-spiro[azetidin-3,7'-furo[3,4,b]pyridine];
3'-[5-(3,5-dichlorophenyl)-5-(trifluoromethyl)-4,5-dihydroisoxazol-3-yl]-1-isobutyryl-5'H-spiro[azetidin-3,7'-furo[3,4,b]pyridine];
1-isobutyryl-3'-[5-(3,4,5-trichlorophenyl)-5-(trifluoromethyl)-4,5-dihydroisoxazol-3-yl]-5'H-spiro[azetidin-3,7'-furo[3,4,b]pyridine];
1-(2'-(5-(3,5-dichloro-4-fluorophenyl)-5-(trifluoromethyl)-4,5-dihydroisoxazol-3-yl)-7'H-spiro[azetidine-3,5'-furo[3,4-b]pyridine]-1-yl)-2-(methylsulfonyl) ethanone;
1-(2'-(5-(3,5-dichlorophenyl)-5-(trifluoromethyl)-4,5-dihydroisoxazol-3-yl)-7'H-spiro[azetidine-3,5'-furo[3,4-b]pyridine]-1-yl)-2-(methylsulfonyl)ethanone;
2-(methylsulfonyl)-1-(2'-(5-(3,4,5-trichlorophenyl)-5-(trifluoromethyl)-4,5-dihydroisoxazol-3-yl)-7'H-spiro[azetidine-3,5'-furo[3,4-b]pyridine]-1-yl)ethanone;

1-(2'-(5-(3,5-dichloro-4-fluorophenyl)-5-(trifluoromethyl)-4,5-dihydroisoxazol-3-yl)-7'H-spiro[azetidine-3,5'-furo[3,4-b]pyridine]-1-yl)-2-methylpropan-1-one;

1-(2'-(5-(3,5-dichlorophenyl)-5-(trifluoromethyl)-4,5-dihydroisoxazol-3-yl)-7'H-spiro[azetidine-3,5'-furo[3,4-b]pyridine]-1-yl)-2-methylpropan-1-one;

2-methyl-1-(2'-(5-(3,4,5-trichlorophenyl)-5-(trifluoromethyl)-4,5-dihydroisoxazol-3-yl)-7'H-spiro[azetidine-3,5'-furo[3,4-b]pyridine]-1-yl)propan-1-one;

1-(6'-(5-(3,5-dichloro-4-fluorophenyl)-5-(trifluoromethyl)-4,5-dihydroisoxazol-3-yl)-1'H-spiro[azetidine-3,3'-furo[3,4-c]pyridine]-1-yl)-2-(methylsulfonyl)ethanone;

2-(methylsulfonyl)-1-(6'-(5-(3,4,5-trichlorophenyl)-5-(trifluoromethyl)-4,5-dihydroisoxazol-3-yl)-1'H-spiro[azetidine-3,3'-furo[3,4-c]pyridine]-1-yl)ethanone;

1-(6'-(5-(3,5-dichlorophenyl)-5-(trifluoromethyl)-4,5-dihydroisoxazol-3-yl)-1H-spiro[azetidine-3,3'-furo[3,4-c]pyridine]-1-yl)-2-(methylsulfonyl)ethanone;

1-(6'-(5-(3,5-dichloro-4-fluorophenyl)-5-(trifluoromethyl)-4,5-dihydroisoxazol-3-yl)-1'H-spiro[azetidine-3,3'-furo[3,4-c]pyridine]-1-yl)-2-methylpropan-1-one;

2-methyl-1-(6'-(5-(3,4,5-trichlorophenyl)-5-(trifluoromethyl)-4,5-dihydroisoxazol-3-yl)-1H-spiro[azetidine-3,3'-furo[3,4-c]pyridine]-1-yl)propan-1-one; and 1-(6'-(5-(3,5-dichlorophenyl)-5-(trifluoromethyl)-4,5-dihydroisoxazol-3-yl)-1'H-spiro[azetidine-3,3'-furo[3,4-c]pyridine]-1-yl)-2-methylpropan-1-one, stereoisomers thereof, and veterinary or pharmaceutical acceptable salts thereof.

In yet another aspect of the invention are compounds of Formula (1.2b) selected from the group consisting of:

1-(6'-(5-(3,5-dichloro-4-fluorophenyl)-5-(trifluoromethyl)-4,5-dihydroisoxazol-3-yl)-1'H-spiro[azetidine-3,3'-furo[3,4-c]pyridine]-1-yl)-2-(methylsulfonyl)ethanone;

2-(methylsulfonyl)-1-(6'-(5-(3,4,5-trichlorophenyl)-5-(trifluoromethyl)-4,5-dihydroisoxazol-3-yl)-1'H-spiro[azetidine-3,3'-furo[3,4-c]pyridine]-1-yl)ethanone;

1-(6'-(5-(3,5-dichlorophenyl)-5-(trifluoromethyl)-4,5-dihydroisoxazol-3-yl)-1H-spiro[azetidine-3,3'-furo[3,4-c]pyridine]-1-yl)-2-(methylsulfonyl)ethanone;

1-(6'-(5-(3,5-dichloro-4-fluorophenyl)-5-(trifluoromethyl)-4,5-dihydroisoxazol-3-yl)-1'H-spiro[azetidine-3,3'-furo[3,4-c]pyridine]-1-yl)-2-methylpropan-1-one;

2-methyl-1-(6'-(5-(3,4,5-trichlorophenyl)-5-(trifluoromethyl)-4,5-dihydroisoxazol-3-yl)-1H-spiro[azetidine-3,3'-furo[3,4-c]pyridine]-1-yl)propan-1-one; and 1-(6'-(5-(3,5-dichlorophenyl)-5-(trifluoromethyl)-4,5-dihydroisoxazol-3-yl)-1'H-spiro[azetidine-3,3'-furo[3,4-c]pyridine]-1-yl)-2-methylpropan-1-one, stereoisomers thereof, and veterinary or pharmaceutical acceptable salts thereof.

In yet another aspect of the invention are Formula (1.3b) compounds selected from the group consisting of:

3'-[5-(3,5-dichlorophenyl)-5-(trifluoromethyl)-4,5-dihydroisoxazol-3-yl]-1-[(methylsulfonyl)acetyl]-5'H-spiro[azetidin-3,7'-furo[3,4,b]pyridine];

3'-[5-(3,5-dichloro-4-fluorophenyl)-5-(trifluoromethyl)-4,5-dihydroisoxazol-3-yl]-1-[(methylsulfonyl)acetyl]-5'H-spiro[azetidin-3,7'-furo[3,4,b]pyridine];

1-[(methylsulfonyl)acetyl]-3'-[5-(3,4,5-trichlorophenyl)-5-(trifluoromethyl)-4,5-dihydroisoxazol-3-yl]-5'H-spiro[azetidin-3,7'-furo[3,4,b]pyridine];

3'-[5-(3,5-dichlorophenyl)-5-(trifluoromethyl)-4,5-dihydroisoxazol-3-yl]-1-isobutyryl-5'H-spiro[azetidin-3,7'-furo[3,4,b]pyridine];

3'-[5-(3,5-dichlorophenyl)-5-(trifluoromethyl)-4,5-dihydroisoxazol-3-yl]-1-isobutyryl-5'H-spiro[azetidin-3,7'-furo[3,4,b]pyridine]; and 1-isobutyryl-3'-[5-(3,4,5-trichlorophenyl)-5-(trifluoromethyl)-4,5-dihydroisoxazol-3-yl]-5'H-spiro[azetidin-3,7'-furo[3,4,b]pyridine], stereoisomers thereof, and veterinary or pharmaceutical acceptable salts thereof.

In another aspect of the invention are Formula (1.4b) compounds selected from the group consisting of:

1-(2'-(5-(3,5-dichloro-4-fluorophenyl)-5-(trifluoromethyl)-4,5-dihydroisoxazol-3-yl)-7'H-spiro[azetidine-3,5'-furo[3,4-b]pyridine]-1-yl)-2-(methylsulfonyl)ethanone;

1-(2'-(5-(3,5-dichlorophenyl)-5-(trifluoromethyl)-4,5-dihydroisoxazol-3-yl)-7'H-spiro[azetidine-3,5'-furo[3,4-b]pyridine]-1-yl)-2-(methylsulfonyl)ethanone;

2-(methylsulfonyl)-1-(2'-(5-(3,4,5-trichlorophenyl)-5-(trifluoromethyl)-4,5-dihydroisoxazol-3-yl)-7'H-spiro[azetidine-3,5'-furo[3,4-b]pyridine]-1-yl)ethanone;

1-(2'-(5-(3,5-dichloro-4-fluorophenyl)-5-(trifluoromethyl)-4,5-dihydroisoxazol-3-yl)-7'H-spiro[azetidine-3,5'-furo[3,4-b]pyridine]-1-yl)-2-methylpropan-1-one;

1-(2'-(5-(3,5-dichlorophenyl)-5-(trifluoromethyl)-4,5-dihydroisoxazol-3-yl)-7'H-spiro[azetidine-3,5'-furo[3,4-b]pyridine]-1-yl)-2-methylpropan-1-one; and 2-methyl-1-(2'-(5-(3,4,5-trichlorophenyl)-5-(trifluoromethyl)-4,5-dihydroisoxazol-3-yl)-7'H-spiro[azetidine-3,5'-furo[3,4-b]pyridine]-1-yl)propan-1-one, stereoisomers thereof, and veterinary or pharmaceutical acceptable salts thereof.

In yet another aspect of the invention are the intermediate compounds selected from the group consisting of tert-butyl-3'-bromo-1H,5'H-spiro[azetidine-3,7'-furo[3,4,b]pyridine]-1-carboxylate, tert-butyl 2'-chloro-1H,7'H-spiro[azetidine-3,5'-furo[3,4-b]pyridine]-1-carboxylate, and tert-butyl 6'-chloro-1H,1'H-spiro[azetidine-3,3'-furo[3,4-c]pyridine]-1-carboxylate. Also contemplated are analogs of the three "boc" protected intermediates, wherein the boc group is replaced with another comparable protecting group, where chemically possible, for example, acyl groups (e.g., formyl, acetyl, chloroacetyl, trichloro-acetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acyl-isothiocyanate, aminocaproyl, benzoyl, and the like), acyloxy groups (e.g., methoxycarbonyl, 9-fluorenyl-methoxycarbonyl, 2,2,2-trifluoroethoxy-carbonyl, 2-trimethylsilylethoxycarbonyl, vinyloxycarbonyl, allyloxycarbonyl, 1,1-dimethylpropynyloxycarbonyl, benzyloxy-carbonyl, p-nitrobenzyloxycarbonyl, 2,4-dichlorobenzyloxycarbonyl, and the like), diphenylmethane, and benzylcarbamates.

In yet another aspect of the invention are Formula (1.1b) compounds described in Table 1, stereoisomers thereof, and veterinary or pharmaceutical acceptable salts thereof.

In yet another aspect of the invention are Formula (1.2b) compounds described in Table 2, stereoisomers thereof, and veterinary or pharmaceutical acceptable salts thereof.

In yet another aspect of the invention are Formula (1.3b) compounds described in Table 3, stereoisomers thereof, and veterinary or pharmaceutical acceptable salts thereof.

In yet another aspect of the invention are Formula (1.4b) compounds described in Table 4, stereoisomers thereof, and veterinary or pharmaceutical acceptable salts thereof.

In yet another aspect of the invention, each of $R^{1a}$, $R^{1b}$, and $R^{1c}$ are independently selected from hydrogen, halo, cyano, $C_1$-$C_6$ haloalkyl, and $C_0$-$C_3$alkyl$C_3$-$C_6$ cycloalkyl. In yet another aspect of the invention, each of $R^{1a}$, $R^{1b}$, and $R^{1c}$ are independently selected from hydrogen, halo, cyano, and $C_1$-$C_6$, haloalkyl. In yet another aspect of the invention, each of $R^{1a}$, $R^{1b}$, and $R^{1c}$ are independently selected from hydrogen, fluoro, chloro, bromo, cyano, and $C_1$-$C_6$haloalkyl. In yet another aspect of the invention, each of $R^{1a}$, $R^{1b}$, and $R^{1c}$ are independently selected from hydrogen, fluoro, chloro, bromo, and $C_1$-$C_6$ haloalkyl. In yet another aspect of the invention, each of $R^{1a}$, $R^{1b}$, and $R^{1c}$ are independently selected from hydrogen, fluoro, chloro, bromo, and —$CF_3$. In another aspect of the invention, each of $R^{1a}$, $R^{1b}$, and $R^{1c}$ are independently selected from chloro, fluoro, and hydrogen. In another aspect of the invention, each of $R^{1a}$, $R^{1b}$, and $R^{1c}$ are chloro. In another aspect of the invention, each of $R^{1a}$ and $R^{1c}$ are chloro and $R1^b$ is fluoro. In another aspect of the invention, each of $R^{1a}$ and $R^{1c}$ are chloro and $R1^b$ is hydrogen.

In yet another aspect of the invention, $R^2$ is halo, cyano, $C_1$-$C_6$alkyl, $C_1$-$C_6$haloalkyl, hydroxyl, —$C(O)NR^aR^b$, —$S(O)_pR$, or —OR. In yet another aspect of the invention, $R^2$ is halo, cyano, $C_1$-$C_6$haloalkyl, or hydroxyl. In yet another aspect of the invention, $R^2$ is fluoro, chloro, bromo, cyano, methyl, ethyl, $CF_3$, or hydroxyl. In yet another aspect of the invention, $R^2$ is fluoro, chloro, cyano, methyl, ethyl, or $CF_3$.

In yet another aspect of the invention, $R^3$ is cyano, $C_1$-$C_6$alkyl, $C_1$-$C_6$haloalkyl, or —$C(O)NH_2$. In yet another aspect of the invention, $R^3$ is cyano, $C_1$-$C_6$alkyl, or $C_1$-$C_6$haloalkyl. In yet another aspect of the invention, $R^3$ is cyano, methyl, ethyl, or $C_1$-$C_6$haloalkyl. In yet another aspect of the invention, $R^3$ is cyano, methyl, or $C_1$-$C_6$haloalkyl. In yet another aspect of the invention, $R^3$ is cyano or $C_1$-$C_6$haloalkyl. In yet another aspect of the invention, $R^3$ is $C_1$-$C_6$haloalkyl. In yet another aspect of the invention, $R^3$ is —$CF_3$, —$CHF_2$, —$CH_2F$, and —$CF_2Cl$. In yet another aspect of the invention, $R^3$ is —$CF_3$, —$CHF_2$, and —$CH_2F$. In yet another aspect of the invention, $R^3$ is —$CF_3$.

In yet another aspect of the invention, $R^4$ is hydrogen, $C_1$-$C_6$alkyl, $C_0$-$C_6$alkyl$C_3$-$C_6$cycloalkyl, —$C(O)R^5$, —$C(S)R^5$, —$C(O)NR^aR^5$, —$S(O)_pR^c$, —$S(O)_2NR^aR^5$, —$C(NR^6)R^5$, $C_0$-$C_6$alkylphenyl, $C_0$-$C_6$alkylheteroaryl, or $C_0$-$C_6$alkylheterocycle. In yet another aspect of the invention, $R^4$ is hydrogen, $C_1$-$C_6$alkyl, $C_0$-$C_6$alkyl$C_3$-$C_6$cycloalkyl, —$C(O)R^5$, —$C(S)R^5$, —$C(O)NR^aR^5$, —$S(O)_pR^c$, —$S(O)_2NR^aR^5$, or —$C(NR^6)R^5$. In yet another aspect of the invention, $R^4$ is hydrogen, $C_1$-$C_6$alkyl, $C_0$-$C_6$alkyl$C_3$-$C_6$cycloalkyl, or —$C(O)R^5$. In yet another aspect of the invention, $R^4$ is hydrogen, $C_1$-$C_6$alkyl, or —$C(O)R^5$. In yet another aspect of the invention, $R^4$ is hydrogen or —$C(O)R^5$. In yet another aspect of the invention, $R^4$ is hydrogen. In yet another aspect of the invention, $R^4$ is —$C(O)R^5$. $R^4$ can be optionally substituted as defined herein.

In yet another aspect of the invention, $R^5$ is $C_1$-$C_6$alkyl, $C_0$-$C_6$alkylphenyl, $C_0$-$C_6$alkyl$C_3$-$C_6$cycloalkyl, $C_0$-$C_6$alkylheteroaryl, or $C_0$-$C_6$alkylheterocycle. In yet another aspect of the invention, $R^5$ is $C_1$-$C_6$alkyl. In yet another aspect of the invention, $R^5$ is methyl, ethyl, propyl, isopropyl, t-butyl, isobutyl, and the like. Each of the $R^5$ $C_1$-$C_6$alkyls can be optionally substituted as defined herein, for example, with at least one substituent selected from hydroxyl, halo, trifluoromethyl, $S(O)_pR^c$, and —NHCHO. In yet another aspect of the invention, $R^5$ is $C_0$-$C_6$alkyl$C_3$-$C_6$cycloalkyl. In yet another aspect of the invention, $R^5$ is cyclopropyl, cyclobutyl, cyclopentyl, —$CH_2$cyclopropyl, —$CH_2$cyclobutyl, —$CH_2$cyclopentyl, thiatane, oxetane, azetidine, —$(CH_2)_2$cyclopropyl, —$(CH_2)_2$cyclobutyl, —$(CH_2)_2$cyclopentyl, —$CH_2$thiatane, —$CH_2$oxetane, —$CH_2$azetidine, tetrahydrofuran, tetrahydrothiophene, pyrrolidine, and the like. Each of the $R^5$ $C_0$-$C_6$alkyl$C_3$-$C_6$cycloalkyls can be optionally substituted as defined herein, for example, with at least one substituent selected from cyano, oxo, —$S(O)_pR^c$, hydroxyl, —$CH_2OH$, halo, methyl, ethyl, and trifluoromethyl. In yet another aspect of the invention, $R^5$ is $C_0$-$C_6$alkylphenyl. In yet another aspect of the invention, $R^5$ is phenyl, —$CH_2$phenyl, —$(CH_2)_2$phenyl, and the like. In yet another aspect of the invention, The $C_0$-$C_6$alkylphenyl moieties can be optionally substituted as defined herein, for example, cyano, hydroxyl, —$S(O)_pR^c$, methyl, halo, and trifluoromethyl. In yet another aspect of the invention, $R^5$ is $C_0$-$C_6$alkylheteroaryl. In yet another aspect of the invention, $R^5$ is pyrazole, imidazole, pyridine, —$CH_2$pyrazole, —$CH_2$pyridine, —$CH_2$imidazole, —$(CH_2)_2$pyrazole, —$(CH_2)_2$pyridine, and —$(CH_2)_2$imidazole. Each of the $R^5$ $C_0$-$C_6$alkylheteroaryl moieties can be optionally substituted as defined herein, for example, with at least one substituent selected from cyano, hydroxyl, —$S(O)_pR^c$, methyl, halo, and trifluoromethyl. In yet another aspect of the invention, $R^5$ is $C_0$-$C_6$alkylheterocycle. In yet another aspect of the invention, $R^5$ is oxirane, thiarane, aziridine, oxetane, azetidine, thiatane, tetrahydrofuran, tetrahydrothiophene, pyrrolidine, tetrahydropyrane, piperidine, piperazine, —$CH_2$oxirane, —$CH_2$thiarane, —$CH_2$aziridine, —$CH_2$oxetane, —$CH_2$azetidine, —$CH_2$thiatane, —$CH_2$tetrahydrofuran, —$CH_2$tetrahydrothiophene, —$CH_2$pyrrolidine, —$CH_2$tetrahydropyrane, —$CH_2$piperidine, —$CH_2$piperazine, and the like. Each of the $R^5$ $C_0$-$C_6$alkylheterocyclic moieties can be optionally substituted as defined herein, for example, with at least one substituent selected from cyano, hydroxyl, —$S(O)_pR^c$, methyl, halo, and trifluoromethyl.

In another aspect of the invention, the integer n of $(R^2)_n$ is 0. In another aspect of the invention, the integer n of $(R^2)_n$ is 1. When the integer n is 1, then $R^2$ is as defined herein. In yet another aspect of the invention, the integer n of $(R^2)_n$ is 2. When the integer n is 2, then each $R^2$ is independent of each other and are as described herein.

In yet another aspect of the invention, p is the integer 0. In yet another aspect of the invention, p is the integer 1. In yet another aspect of the invention, p is the integer 2.

In another aspect of the invention, is a veterinary composition that comprises a Formula (1) compound, stereoisomers thereof, or a veterinary or pharmaceutical acceptable salt thereof. Preferably, the composition comprises a therapeutically effective amount of a Formula (1) compound, stereoisomer thereof, or veterinary or pharmaceutical acceptable salt thereof. In another aspect of the invention, the composition comprising a Formula (1) compound, stereoisomer thereof, an pharmaceutically or veterinary or pharmaceutical acceptable salt thereof, further comprises at least one veterinary or pharmaceutical acceptable carrier.

The composition may comprise at least one additional veterinary agent. Preferred additional veterinary agents include endoparasiticides, endectocides, ectoparasiticides, insecticides, and anthelmintics, and are described herein. In one aspect of the invention, the additional veterinary agent is selected from amitraz, amino acetonitriles (e.g., monepantel, those disclosed in WO2008/096231 and WO2008/102232), anthelmintics (e.g., albendazole, cambendazole, fenbendazole, flubendazole, mebendazole, octadepsipeptides, oxfendazole, oxibendazole, paraherquamides (e.g., derquantel), parbendazole, piperazines, praziquantel, thiabendazole, tetramisole, triclabendazole, levamisole, pyrantel pamoate, oxantel, morantel, and the like), avermectins (e.g., abamectin, doramectin, emamectin, eprinomectin, ivermectin, moxidectin, selamectin, and the like), milbemycin, milbemycin oxime, demiditraz, diethylcarbamazine, fipronil, hydroprene, kinoprene, methoprene, metaflumizone, niclosamide, permethrin, pyrethrins, pyriproxyfen, and spinosad. In another aspect of the invention, the additional agent is selected from an amino acetonitrile, albendazole, cambendazole, fenbendazole, flubendazole, mebendazole, oxfendazole, oxibendazole, paraherquamide, parbendazole, praziquantel, thiabendazole, tetramisole, triclabendazole, levamisole, pyrantel pamoate, oxantel, morantel, abamectin, doramectin, emamectin, eprinomectin, ivermectin, moxidectin, selamectin, milbemycin, milbemycin oxime, demiditraz, diethylcarbamazine, fipronil, hydroprene, kinoprene, methoprene, metaflumizone, niclosamide, pyriproxyfen, and spinosad. In yet another aspect of the invention, the additional agent is selected from an amino acetonitrile (e.g., monepantel), paraherquamide, praziquantel, abamectin, doramectin, emamectin, eprinomectin, ivermectin, moxidectin, selamectin, milbemycin, and milbemycin oxime. In yet another aspect of the invention, the additional agent is selected from abamectin, doramectin, emamectin, eprinomectin, ivermectin, moxidectin, selamectin, milbemycin, and milbemycin oxime. In yet another aspect of the invention, the additional agent is selected from abamectin, doramectin, eprinomectin, ivermectin, moxidectin, selamectin, milbemycin, and milbemycin oxime. In yet another aspect of the invention, the additional agent is selected from moxidectin, selamectin, and milbemycin oxime. In yet another aspect of the invention, the additional agent is selected from moxidectin and milbemycin oxime.

In yet another aspect of the invention is the use of a Formula (1) compound for the manufacture of a medicament.

In yet another aspect of the invention is a method for treating a parasitic infection or infestation in an animal that includes the step of administering to said animal, in need of such treatment, a therapeutically effective amount of a compound of the present invention, stereoisomer thereof, or veterinary or pharmaceutical acceptable salt thereof, in combination with at least one additional veterinary agent. In one aspect, the animal is a mammal, specifically a companion animal (for example, dog, cat, or horse) or livestock (for example, sheep, goat, cattle, and pig). In another aspect, the animal is a bird, specifically fowl (for example, chicken, turkey, duck, and geese). In another aspect, the animal is a fish. The compounds of the present invention, and compositions thereof, can be administered to the animal orally or topically. The compounds of the present invention, and compositions thereof, can also be administered to the animal by intramuscular-, intraperitoneal-, or subcutaneous-injection. Preferrably, the compounds of the present invention, and compositions thereof, can be administered to the animal orally or topically. Equally preferred, the compounds of the present invention can be administered by injection.

Compounds of the present invention alone, or in combination with an additional veterinary agent(s) may be administered as (a) a single veterinary composition which comprises a compound of the present invention, stereoisomer thereof, veterinary or pharmaceutical acceptable salt thereof, and optionally, at least one additional veterinary agent as described herein and at least one veterinary or pharmaceutical acceptable carrier; or (b) two separate veterinary compositions comprising (i) a first composition comprising a compound of the present invention, stereoisomer thereof, veterinary or pharmaceutical acceptable salt thereof, and at least one veterinary or pharmaceutical acceptable carrier, and (ii) a second composition comprising at least one additional veterinary agent, as described herein and at least one veterinary or pharmaceutical acceptable carrier. The veterinary compositions may be administered simultaneously or sequentially and in any order.

All of the recited patent applications and patent application publications herein are incorporated in their entirety by reference.

DEFINITIONS

For purposes of the present invention, as described and claimed herein, the following terms and phrases are defined as follows:

"Additional veterinary agent(s)" as used herein, unless otherwise indicated, refers to other veterinary or pharmaceutical compounds or products that provide a therapeutically effective amount of said agents that are useful for the treatment of a parasitic infection in an animal, as described herein.

"Alkoxy", as used herein, unless otherwise indicated, refers to an oxygen moiety having a further alkyl substituent. The alkyl portion (i.e., alkyl moiety) of an alkoxy group has the same definition as below. Non-limiting examples include: —OCH$_3$, —OCH$_2$CH$_3$, and the like.

"Alkyl", as used herein, unless otherwise indicated, refers to saturated monovalent hydrocarbon alkane radicals of the general formula $C_nH_{2n+1}$. The alkane radical may be straight or branched and may be unsubstituted or substituted. For example, the term "(C$_1$-C$_6$)alkyl" refers to a monovalent, straight or branched aliphatic group containing 1 to 6 carbon atoms. Non-exclusive examples of (C$_1$-C$_6$) alkyl groups include, but are not limited to methyl, ethyl, propyl, isopropyl, sec-butyl, t-butyl, n-propyl, n-butyl, i-butyl, s-butyl, n-pentyl, 1-methylbutyl, 2-methylbutyl, 3-methylbutyl, neopentyl, 3,3-dimethylpropyl, 2-methylpentyl, hexyl, and the like. The alkyl moiety may be attached to the chemical moiety by any one of the carbon atoms of the aliphatic chain. Alkyl groups are optionally substituted as described herein. Further when used in compound words such as alkylphenyl, said alkyl moiety has the same meaning as herein defined and may be attached to the chemical moiety by any one of the carbon atoms of the aliphatic chain. Non-limiting examples of the compound word, alkylphenyl include: C$_1$alkylphenyl is —CH$_2$phenyl, C$_2$alkylphenyl is —CH$_2$CH$_2$phenyl, C$_0$phenyl is phenyl, and the like.

"Alkenyl" as used herein, unless otherwise indicated, refers to a straight or branched aliphatic hydrocarbon chain having 2- to 6-carbon atoms and containing at least one carbon-carbon double bond (for example —C═C—, or —C═CH$_2$). Non-exclusive examples of alkenyl include: ethenyl, 1-propenyl, 2-propenyl, isopropenyl, 1-butenyl, 2-butenyl, 3-butenyl, 2-pentenyl, and the like.

"Alkynyl" as used herein, unless otherwise indicated, refers to straight or branched aliphatic hydrocarbon chain having 2- to 6-carbon atoms and containing at least one carbon-carbon triple bond (for example, —C≡C— or —C≡CH). Non-exclusive examples of alkynyl include: ethynyl, 2-propynyl, 1-methyl-2-propynyl, 2-butynyl, 3-butynyl, 2-methyl-3-butynyl, and the like.

"Animal(s)", as used herein, unless otherwise indicated, refers to an individual animal that is a mammal, bird, or fish. Specifically, mammal refers to a vertebrate animal that is human and non-human, which are members of the taxonomic class Mammalia. Non-exclusive examples of non-human mammals include companion animals and livestock. Non-exclusive examples of a companion animal include: dog, cat, llama, and horse. Preferred companion animals are dog, cat, and horse. More preferred is dog. Non-exclusive examples of livestock include: swine, camel, rabbits, goat, sheep, deer, elk, bovine (cattle), and bison. Preferred livestock is cattle and swine. Specifically, bird refers to a vertebrate animal of the taxonomic class Aves. Birds are feathered, winged, bipedal, endothermic, and egg-laying. Non-exclusive examples of bird include, poultry (e.g., chicken, turkey, duck, and geese), all of which are also referred to herein as fowl. Specifically, fish refers to the taxonomic class Chondrichthyes (cartilaginous fishes, e.g., sharks and rays) and Osteichthyes (bony fishes) which live in water, have gills or mucus-covered skin for respiration, fins, and may have scales. Non-exclusive examples of fish include shark, salmon, trout, whitefish, catfish, tilapia, sea bass, tuna, halibut, turbot, flounder, sole, striped bass, eel, yellowtail, grouper, and the like.

"Carbocyclic", as used herein, unless otherwise indicated, refers to a partially saturated or saturated 5- to 7-membered ring containing only carbon atoms and can be monocyclic or part of a fused ring or spiro ring moiety. Examples of carbocyclic rings include cyclopentane, cyclohexane, and cycloheptane.

"Chiral", as used herein, unless otherwise indicated, refers to the structural characteristic of a molecule that makes it impossible to superimpose it on its mirror image, (e.g., "R" and "S" enantiomers). The term is also depicted as an asterisk (i.e., *) in the Examples and preparations and refers to a chiral center which includes both the S and R enantiomers.

"Compounds of the present invention", as used herein, unless otherwise indicated, refers to Formula (1) compounds, and stereoisomers thereof, and veterinary or pharmaceutical acceptable salts thereof.

"Cycloalkyl", as used herein, unless otherwise indicated, includes fully saturated or partially saturated carbocyclic alkyl moieties. Non-limiting examples of partially saturated cycloalkyls include: cyclopropene, cyclobutene, cycloheptene, cyclooctene, cyclohepta-1,3-diene, and the like. Preferred cycloalkyls are 3- to 6-membered saturated monocyclic rings including cyclopropyl, cyclobutyl, cyclopentyl, and cyclohexyl. The cycloalkyl group may be attached to the chemical moiety by any one of the carbon atoms within the ring. Cycloalkyl groups are optionally substituted with at least one substituent. Further when used in compound words such as alkylcycloalkyl, said alkyl and cycloalkyl moiety has the same meaning as herein defined and may be attached to the chemical moiety by any one of the carbon atoms of the aliphatic chain. Examples of $C_0$-$C_6$alkyl$C_3$-$C_6$cycloalkyl include, methylcyclopropane ($C_1$alkyl$C_3$cycloalkyl or —$CH_2$cyclopropane), ethylcyclopropane ($C_2$alkyl$C_3$cycloalkyl or —$CH_2CH_2$cyclopropane), methylcyclobutane ($C_1$alkyl$C_4$cycloalkyl or —$CH_2$cyclobutane), ethylcyclobutane ($C_2$alkyl$C_4$cycloalkyl or —$CH_2CH_2$cyclobutane), methylcyclohexane ($C_1$alkyl$C_6$cycloalkyl or —$CH_2$cyclohexane), and the like. $C_0$alkyl$C_3$-$C_6$cycloalkyl is $C_3$-$C_6$cycloalkyl. Cycloalkyl moieties are optionally substituted as described herein "Halogen" or "halo", as used herein, unless otherwise indicated, refers to fluorine, chlorine, bromine and iodine. Further, when used in compound words such as "haloalkyl", "haloalkoxy", "haloalkenyl", or "haloalkynyl", said alkyl, alkoxy, alkenyl, and alkynyl may be partially or fully substituted with halogen atoms which may be the same or different and said alkyl, alkoxy, alkenyl, and alkynyl moiety has the same meaning as above and may be attached to the chemical moiety by any one of the carbon atoms of the aliphatic chain. Examples of "haloalkyl" include $F_3C$—, $ClCH_2$—, $CF_3CH_2$— and $CF_3CCl_2$—, and the like. The term "haloalkoxy" is defined analogously to the term "haloalkyl". Examples of "haloalkoxy" include $CF_3O$—, $CCl_3CH_2O$—, $HCF_2CH_2CH_2O$— and $CF_3CH_2O$—, and the like. The term "haloalkenyl" is defined analogously to the term "haloalkyl" except that the aliphatic chain contains at least one carbon-carbon double bond. Examples of "haloalkenyl" include $CF_3C$=C—, $CCl_3C$=C—, $HCF_2C$=C— and $CF_3C$=CC—, and the like. The term "haloalkynyl" is defined analogously to the term "haloalkyl" except that the aliphatic chain contains at least one carbon-carbon triple bond. Examples of "haloalkynyl" include $F_3CC$≡C—, $Cl_3CC$≡C—, $HF_2CC$≡C—, and the like.

"Heteroaryl" or "Het", as used herein, unless otherwise indicated, refers to a 5- to 6-membered aromatic monocyclic ring or an 8- to 10-membered fused aromatic ring where said monocyclic- and fused-ring moiety contains one or more heteroatoms each independently selected from N, O, or S, preferably from one to four heteroatoms. Non-exclusive examples of monocyclic heteroaryls include pyrrolyl, furanyl, thiophenyl, pyrazolyl, imidazolyl, triazolyl, tetrazolyl, thiazolyl, isoxazolyl, oxazolyl, oxadiazolyl, thiadiazolyl, pyridinyl, pyridazinyl, pyrimidinyl, pyrazinyl, and the like. Non-exclusive examples of fused heteroaryls include: benzofuranyl, benzothiophenyl, indolyl, benzimidazolyl, indazolyl, benzotriazolyl, thieno[2,3-c]pyridine, thieno[3,2-b]pyridine, benzo[1,2,5]thiadiazole, and the like. The heteroaryl group may be attached to the chemical moiety by any one of the carbon atoms or nitrogen heteroatoms within the monocyclic or fused ring. Further when used in compound words such as alkylheteroaryl, said alkyl and heteroaryl moiety have the same meaning as herein defined and may be attached to the chemical moiety by any one of the carbon atoms of the aliphatic chain. For example, $C_0$alkylheteroaryl is heteroaryl, $C_1$alkylheteroaryl is —$CH_2$heteroaryl, $C_2$alkylheteroaryl is —$CH_2CH_2$heteroaryl, and the like. Heteroaryls are optionally substituted as described herein.

"Heterocycle", as used herein, unless otherwise indicated, refers to a partially saturated or saturated 3- to 7-membered monocyclic ring containing one or more heteroatoms each independently selected from N, O, or S, preferably from one to four heteroatoms. The heterocyclic ring can be part of a fused ring or spiro-ring moiety. Non-exclusive examples of heterocycle include oxirane, thiarane, aziridine, oxetane, azetidine, thiatane, tetrahydrofuran, tetrahydrothiophene, pyrrolidine, tetrahydropyrane, piperidine, piperazine, tetrahydropyridine, 2H-azirine, 2,3-dihydro-azete, 3,4-dihydro-2H-pyrrole, and the like. The heterocycle group may be attached to the chemical moiety by any one of the carbon atoms or nitrogen heteroatoms within the ring. Further when used in compound words such as alkylheterocycle, said alkyl and heterocycle moiety have the same meaning as herein defined and may be attached to the chemical moiety by any one of the carbon atoms of the aliphatic chain. For example, $C_0$alkylheterocycle is heterocycle, $C_1$alkylheterocycle is —$CH_2$heterocycle, $C_2$alkylheterocycle is —$CH_2CH_2$heterocycle, and the like. Heterocycles are optionally substituted as described herein.

"Optionally substituted", is used herein interchangeably with the phrase substituted or unsubstituted. Unless otherwise indicated, an optionally substituted group may have a substituent at each substitutable position of the group, and each substitution is independent of the other. An optionally substituted group also may have no substituents. Therefore, the phrase "optionally substituted with at least one substituent" means that the number of substituents may vary from zero up to a number of available positions for substitution.

"Parasite(s)", as used herein, unless otherwise indicated, refers to endoparasites and ectoparasites. Endoparasites are parasites that live within the body of its host and include helminths (e.g., trematodes, cestodes, and nematodes) and protozoa. Ectoparasites are organisms of the Arthropoda phylum (e.g., arachnids, insects, and crustaceans (e.g., copepodssea lice) which feed through or upon the skin of its host. Preferred arachnids are of the order Acarina, e.g., ticks and mites. Preferred insects are midges, fleas, mosquitos, biting flies (stable fly, horn fly, blow fly, horse fly, and the like), bed bugs, and lice. Preferred compounds of the present invention can be used for the treatment of parasites, i.e., treatment of a parasitic infection or infestation.

"Protecting group" or "Pg", as used herein, unless otherwise indicated, refers to a substituent that is commonly employed to block or protect an amine on the compound thereby protecting its functionality while allowing for the reaction of other functional groups on the compound. Non-exclusive examples of an amine-protecting group include: acyl groups (e.g., formyl, acetyl, chloroacetyl, trichloro-acetyl, o-nitrophenylacetyl, o-nitrophenoxyacetyl, trifluoro-acetyl, acetoacetyl, 4-chlorobutyryl, isobutyryl, o-nitrocin-namoyl, picolinoyl, acylisothiocyanate, aminocaproyl, benzoyl, and the like), acyloxy groups (e.g., 1-tert-butyloxy-carbonyl (Boc), methoxycarbonyl, 9-fluorenyl-methoxycar-bonyl, 2,2,2-trifluoroethoxy-carbonyl, 2-trimethylsi-lylethoxycarbonyl, vinyloxycarbonyl, allyloxycarbonyl, 1,1-dimethyl-propynyloxycarbonyl, benzyloxy-carbonyl, p-nitrobenzyloxycarbonyl, 2,4-dichlorobenzyloxycarbonyl, and the like), diphenylmethane, and benzylcarbamates.

"Sulfonate leaving group", as used herein, unless otherwise indicated, refers to anions with the general formula $RSO_2O^-$. Non limiting examples of a sulfonate leaving group include: mesylate (R=$CH_3$), triflate (R=$CF_3$), tosylate (R=$CH_3C_6H_4$), besylate (R=$C_6H_5$), tresylate (R=$CH_2CF_3$), and the like.

"Therapeutically effective amount", as used herein, unless otherwise indicated, refers to an amount of the compounds of the present invention that (i) treat the particular parasitic infection or infestation, (ii) attenuates, ameliorates, or eliminates one or more symptoms of the particular parasitic infection or infestation, or (iii) prevents or delays the onset of one or more symptoms of the particular parasitic infection or infestation described herein.

"Treatment", "treating", and the like, as used herein, unless otherwise indicated, refers to reversing, alleviating, or inhibiting the parasitic infection, infestation, or condition. As used herein, these terms also encompass, depending on the condition of the animal, preventing the onset of a disorder or condition, or of symptoms associated with a disorder or condition, including reducing the severity of a disorder or condition or symptoms associated therewith prior to affliction with said infection or infestation. Thus, treatment can refer to administration of the compounds of the present invention to an animal that is not at the time of administration afflicted with the infection or infestation. Treating also encompasses preventing the recurrence of an infection or infestation or of symptoms associated therewith as well as references to "control" (e.g., kill, repel, expel, incapacitate, deter, eliminate, alleviate, minimize, and eradicate).

"Veterinary or pharmaceutical acceptable" as used herein, unless otherwise indicated, indicates that the substance or composition must be compatible chemically and/or toxicologically, with the other ingredients comprising a formulation, composition, and/or the animal being treated therewith. The term "pharmaceutically" acceptable has the same meaning as that recited for "veterinary" acceptable.

DETAILED DESCRIPTION

The present invention provides Formula (1) compounds, stereoisomers thereof, as well as veterinary compositions that are useful as antiparasitic agents for animals, in particular, compounds that act as ectoparasiticides.

Compounds of the present invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, "Reagents for Organic Synthesis", 1; 19, Wiley, New York (1967, 1999 ed.), or *Beilsteins Handbuch der organischen Chemie*, 4, Aufl. ed. Springer-Verlag, Berlin, including supplements (also available via the Beilstein online database)). For illustrative purposes, the reaction schemes depicted below demonstrate potential routes for synthesizing compounds of the present invention, and key intermediates. For a more detailed description of the individual reaction steps, see the Examples section below. A skilled artisan will appreciate that other suitable starting materials, reagents, and synthetic routes may be used to synthesize the compounds of the present invention and a variety of derivatives thereof. Further, many of the compounds prepared by the methods described below can be further modified in light of this disclosure using conventional chemistry well known to the skilled artisan.

Compounds of the present invention described herein contain at least one asymmetric or chiral center; and, therefore, exist in different stereoisomeric forms. The R and S configurations are based upon knowledge of known chiral inversion/retention chemistry. Unless specified otherwise, it is intended that all stereoisomeric forms of the compounds of the present invention as well as mixtures thereof, including racemic mixtures and diastereomeric mixtures, form part of the present invention.

Enantiomeric mixtures can be separated into their individual enantiomers on the basis of their physical chemical differences by methods well known to those skilled in the art, such as chromatography and/or fractional crystallization. A more detailed description of techniques that can be used to resolve stereoisomers of compounds from their racemic mixture can be found in Jean Jacques Andre Collet, Samuel H. Wilen, Enantiomers, Racemates and Resolutions, John Wiley and Sons, Inc. (1981).

Compounds of this invention can exist as one or more stereoisomers. The various stereoisomers include enantiomers, diastereomers and atropisomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereo isomers or as an optically active form. For example, two possible enantiomers of Formula 1 are depicted as Formula 1a and Formula 1b involving the spirocyclic isoxazoline chiral center identified with an asterisk (*). Molecular depictions drawn herein follow standard conventions for depicting stereochemistry.

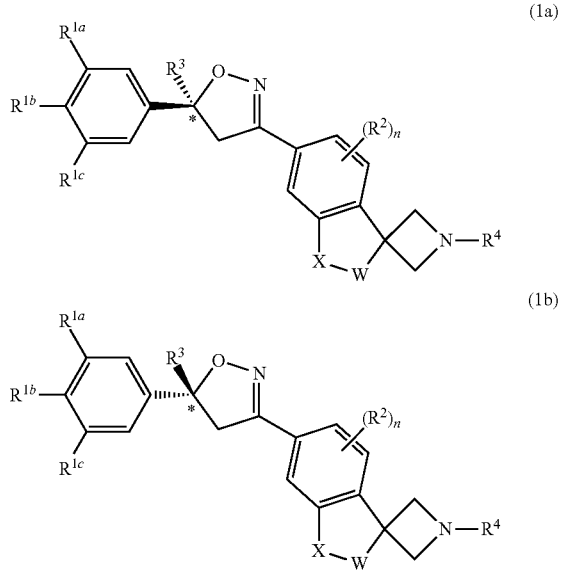

For illustrative purposes, the reaction schemes depicted below demonstrate potential routes for synthesizing key intermediates and compounds of the present invention. For a more detailed description of the individual reaction steps, see the Examples section below. Those skilled in the art will appreciate that other suitable starting materials, reagents, and synthetic routes may be used to synthesize the intermediates and compounds of the present invention and a variety of derivatives thereof. Further, many of the compounds prepared by the methods described below can be further modified in light of this disclosure using conventional chemistry. Schemes 1-7 outline the general procedures useful for the preparation and isolation of compounds of the present invention. It is to be understood, however, that the invention, as fully described herein and as recited in the claims, is not intended to be limited by the details of the following schemes or modes of preparation.

In the preparation of compounds of the present invention, protection of remote functionality of intermediates from undesired reactions can be accomplished with a protecting group. The term "protecting group" or "Pg" refers to a substituent that is commonly employed to block or protect a particular functionality while reacting other functional groups on the compound. For example, an amine-protecting group is a substituent attached to an amine that blocks or protects the amine-functionality of the compound or intermediate. Suitable amine protecting groups include: 1-tert-butyloxycarbonyl (Boc), acyl groups including: formyl, acetyl, chloroacetyl, trichloro-acetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl, and the like; and acyloxy groups including: methoxycarbonyl, 9-fluorenyl-methoxycarbonyl, 2,2,2-trifluoroethoxycarbonyl, 2-trimethylsilylethoxycarbonyl, vinyloxycarbonyl, allyloxycarbonyl, 1,1-dimethyl-propynyloxycarbonyl, benzyloxy-carbonyl, p-nitrobenzyloxycarbonyl, 2,4-dichlorobenzyloxycarbonyl, and the like. Similarly, diphenylmethane and benzylcarbamates can be used as amine protecting groups. Suitable protecting groups and their respective uses are readily determined by one skilled in the art. For a general description of protecting groups and their use, see T. W. Greene, *Protective Groups in Organic Synthesis*, John Wiley & Sons, New York, 1991.

In the Schemes below, the following catalysts/reactants and miscellaneous abbreviations include: mobile phase (MP); N,N-dimethyl formamide (DMF); dimethyl acetamide (DMA); acetonitrile (ACN or Acn); formic acid (FA); dichloromethane (DCM); N-chloro-succinimide (NCS); ethanol (EtOH); methyl tert-butyl ether (MTBE); triethylamine (TEA or Et$_3$N); methanol (MeOH), tetrahydrofuran (THF); ethyl acetate (EtOAc); trifluoroacetic acid (TFA); triphenylphosphine palladium (Pd(PPh$_3$)$_4$); (2,2,6,6-tetramethylpiperidin-1-yl)oxyl (TEMPO); and diisobutylaluminium hydride (DIBAL-H); 4-dimethylaminopyridine (DMAP); potassium bis(trimethylsilyl) (KHMDS); N-chlorosuccinimide (NCS); 1,3-bis(diphenylphosphino)propane (DPPP); amidecarbonyldiimidazole (CDI); 1-hydroxybenzotriazole hydrate (HOBt); and N, N,N',N'-Tetramethyl-O-(7-azabenzotriazol-1-yl)uronium hexafluorophosphate (HATU), methanesulfonyl chloride (mesyl chloride, MsCl); isopropylmagnesium chloride (iPrMgCl); t-butyloxycarbonyl (BOC); palladium (II) acetate (Pd(OAc)$_2$); lithium borohydride (LiBH$_4$), palladium catalyst ("Pd"); dichloroethane (DCE); propylphosphonic anhydride (T$_3$P); isopropylmagnesium chloride (iPrMgCl); N-bromosuccinimide (NBS); azobisisobutyronitrile (AIBN); and n-butyllithium (n-BULI).

SCHEMES

Scheme 1: Spiropyridine Intermediates

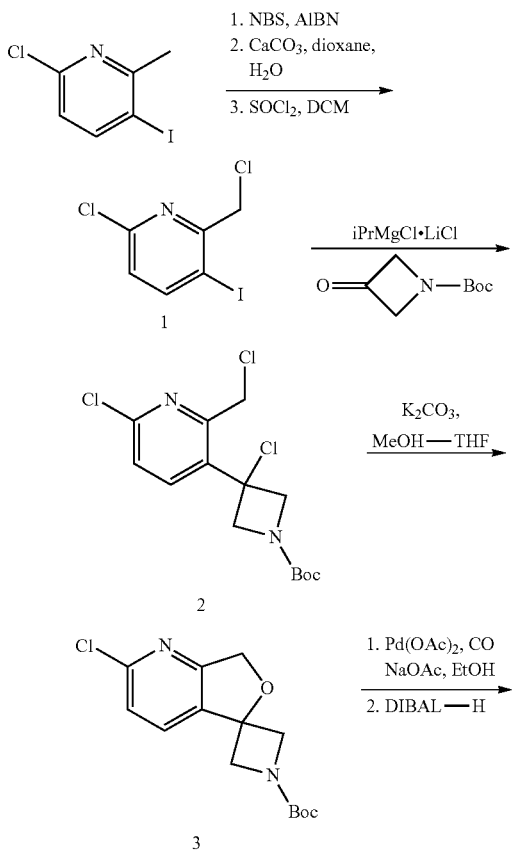

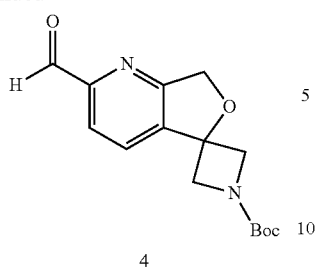

4

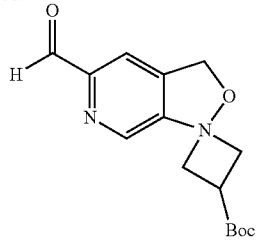

9

($R^8$=$C_1$—C alkyl)

Starting from commercially available 6-chloro-3-iodo-2-methylpyridine, a sequence of benzylic bromination, hydrolysis and conversion to the chloride provides the halide 1. Treatment of 1 with BuLi as described in *Tetrahedron Letters*, 2003, 44(14), 2971-2974 or with an organomagnesium reagent such as iPrMgCl, and addition of N-Boc azetidinone provides the alcohol 2 which under basic conditions forms the oxaspirocycle 3. Palladium mediated carbonylation in the presence of ethanol and subsequent reduction of the resulting ester affords the aldehyde intermediate 4.

Starting with the aminopyridine 5, chlorination via diazotization and subsequent benzylic bromination and hydrolysis provides alcohol 6. Metallation by halogen-metal exchange with BuLi or by treatment with an organomagnesium reagent such as iPrMgCl as described in Scheme 1, and addition of N-boc azetidinone provides diol 7. Exposure of diol 7 to tosyl anhydride in the presence of base affords the oxaspirocycle 8. Palladium mediated carbonylation and subsequent reduction affords the aldehyde intermediate 9.

Scheme 2: Spiropyridine Intermediates

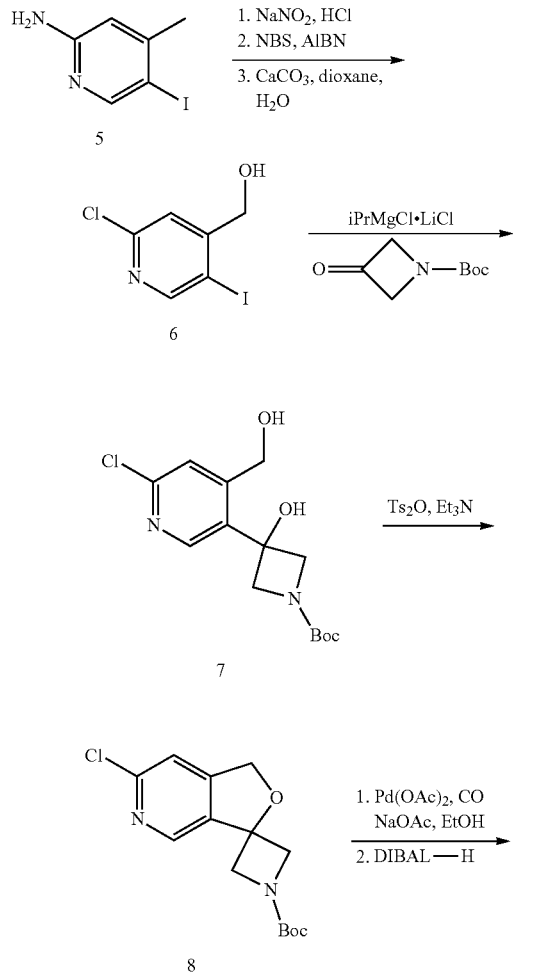

Scheme 3: Spiropyridine Intermediates

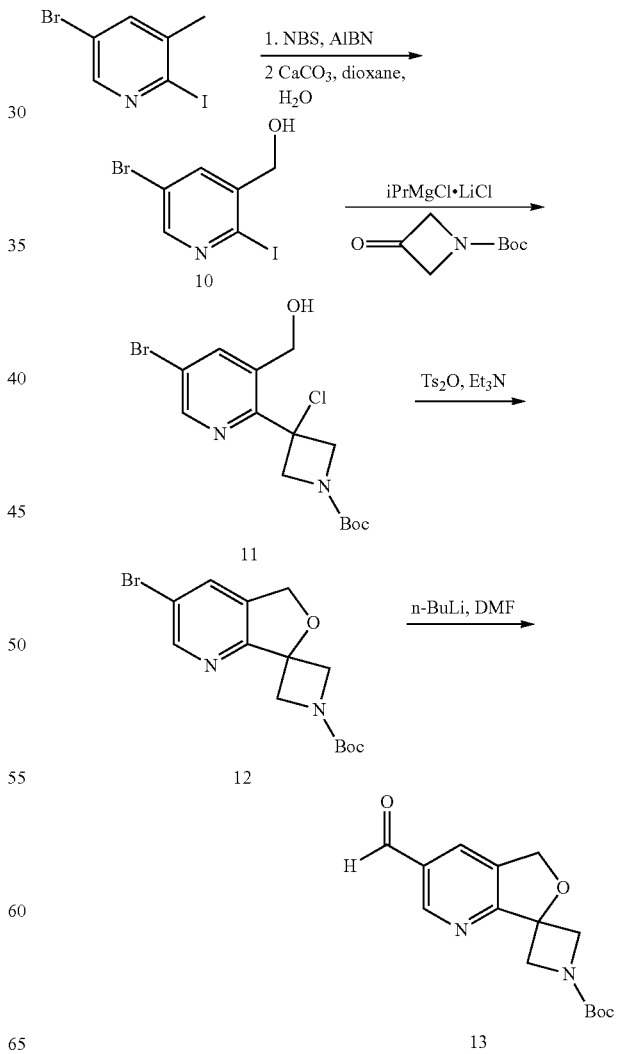

Benzylic bromination of the starting substituted alkylpyridine followed by hydrolysis provides the alcohol 10. Metallation of 10 by halogen-metal exchange with BuLi or iPrMgCl.LiCl followed by addition of N-Boc azetidinone provides diol 11. Exposure of diol 11 to tosyl anhydride in presence of base affords the oxaspirocycle 12. Aryl formylation of 12 yields the aldehyde intermediate 13.

Scheme 4: Spirocyclic Intermediates

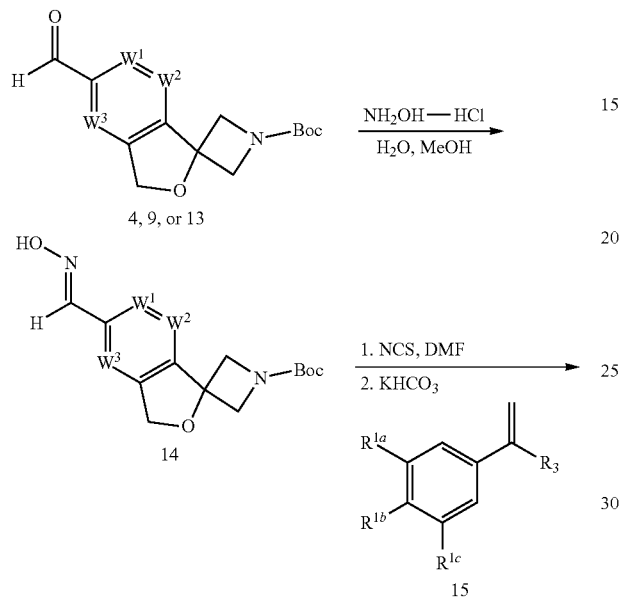

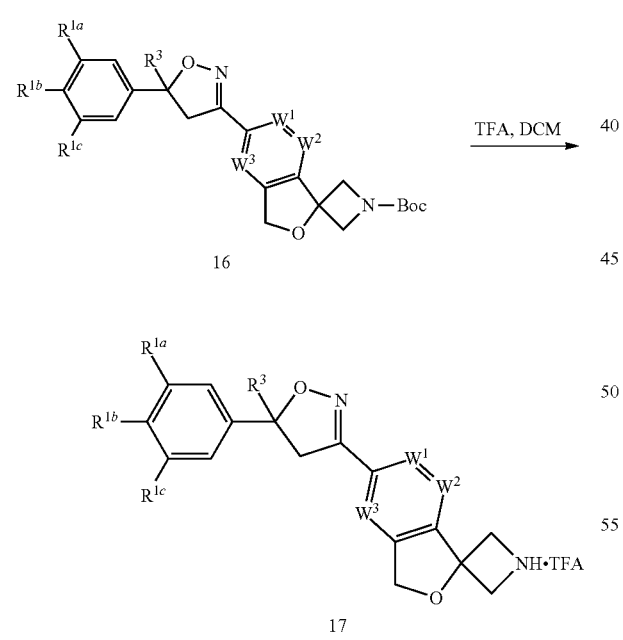

Condensation of the aldehyde intermediate 4, 9, or 13 with hydroxylamine to oxime 14 and subsequent chlorination and reaction with the aryl olefin 15 provides the isoxazoline 16. Deprotection under acidic conditions, such as methanolic HCl or trifluoroacetic acid, provides the intermediate amine salt 17.

Scheme 5: Amide Formation

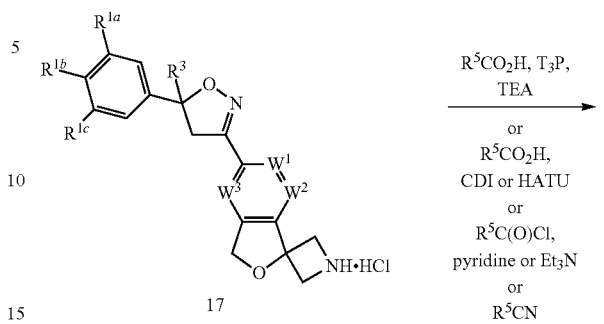

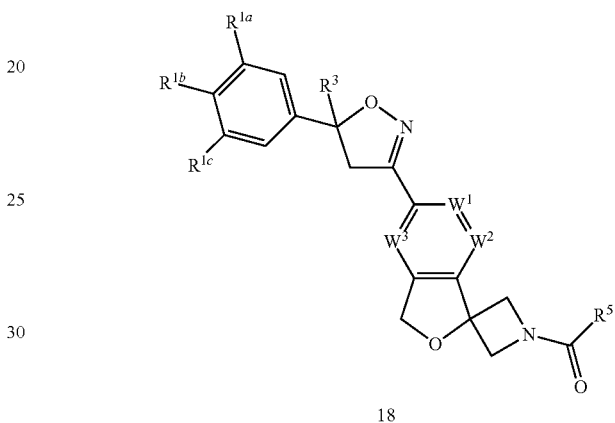

Coupling the spiroazetidine compounds of Formula 17 with an acid or acid chloride under standard amide formation conditions provides amides of Formula 18.

Scheme 6: Chiral Synthesis of spiropyridines

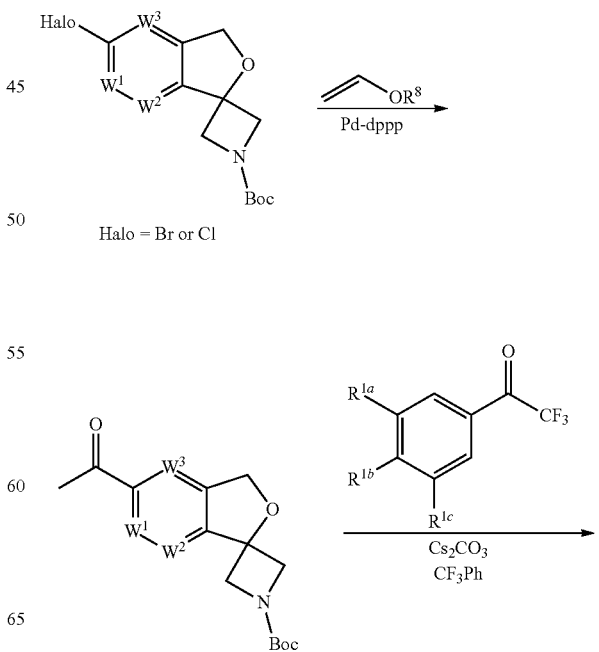

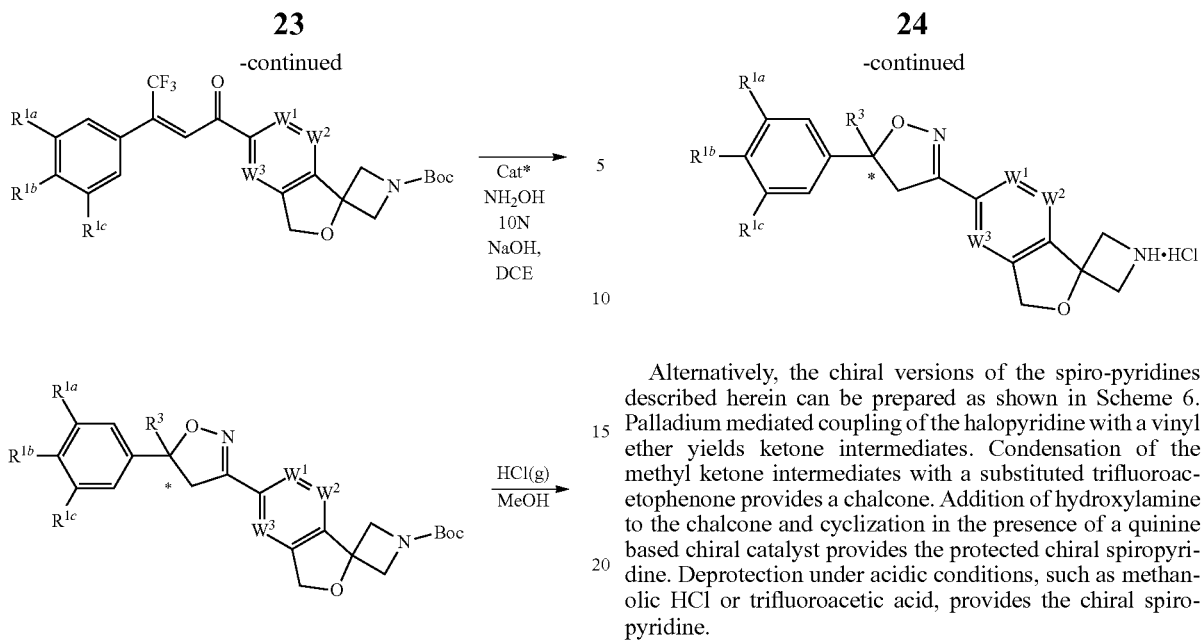

Alternatively, the chiral versions of the spiro-pyridines described herein can be prepared as shown in Scheme 6. Palladium mediated coupling of the halopyridine with a vinyl ether yields ketone intermediates. Condensation of the methyl ketone intermediates with a substituted trifluoroacetophenone provides a chalcone. Addition of hydroxylamine to the chalcone and cyclization in the presence of a quinine based chiral catalyst provides the protected chiral spiropyridine. Deprotection under acidic conditions, such as methanolic HCl or trifluoroacetic acid, provides the chiral spiro-pyridine.

Scheme 7: Spirothioether

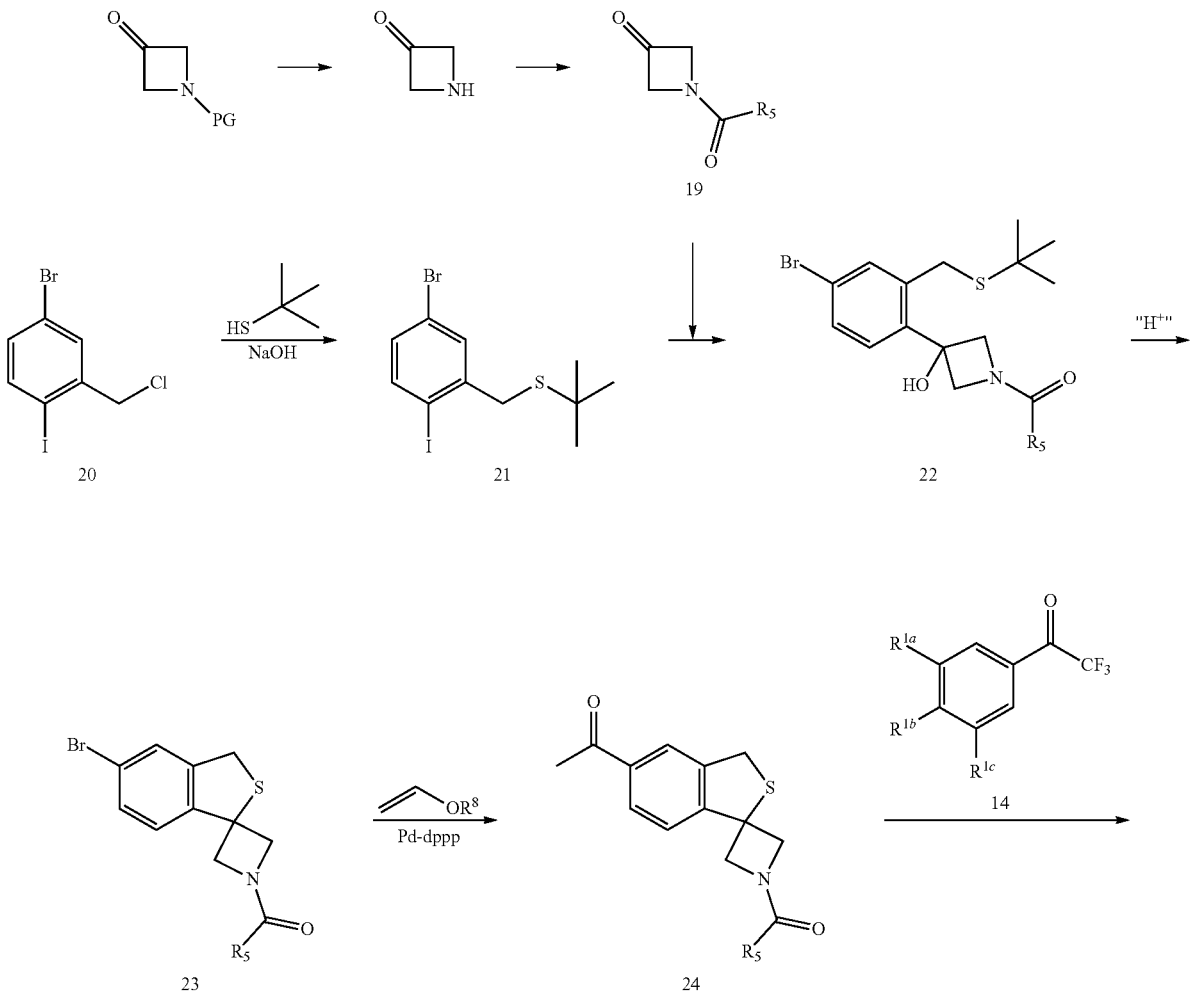

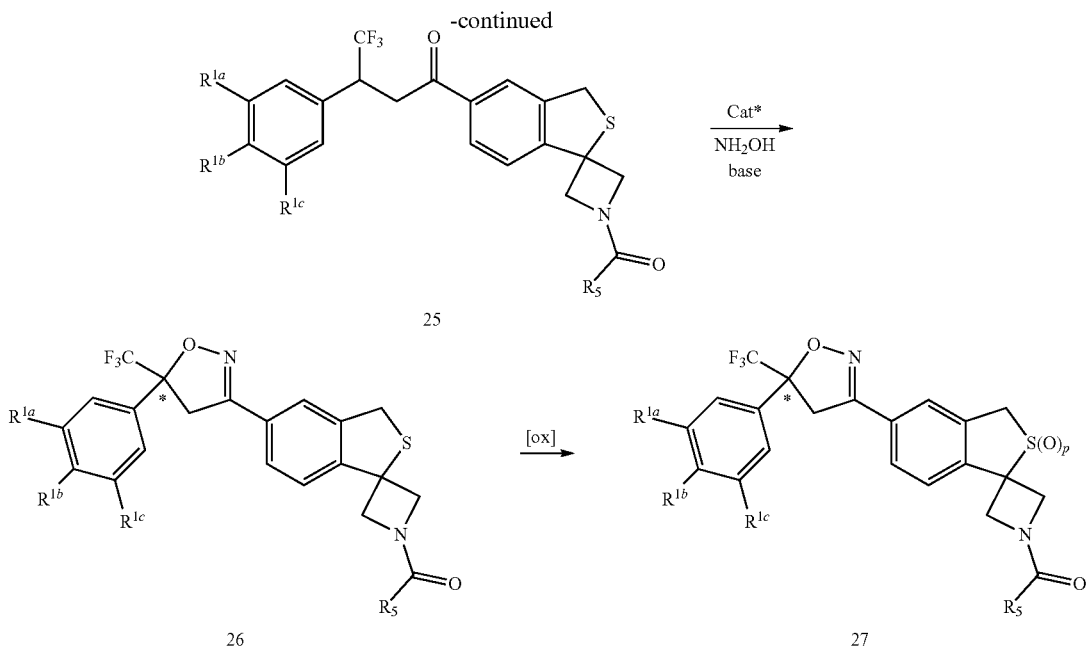

($R^8$=$C_1$-$C_6$ alkyl)

Reaction of the benzylic chloride 20 with t-BuSH using a suitable base provides sulfide intermediate 21. Metal-halogen exchange of the iodine with BuLi oriPrMgCl.LiCl followed by addition of 19 (formed by deprotection of commercially available azetidinone and amide formation under standard conditions) yields alcohol intermediate 22. Acid mediated cyclization provides thiospiroethers 23. Palladium mediated coupling with a vinyl ether provides ketone intermediates 24. Condensation of 24 with trifluoroacetophenone of Formula 14 provides compounds of Formula 25. Addition of hydroxylamine to compounds of Formula 25 and cyclization in the presence of a quinine based chiral catalyst provides compounds of Formula 26. Selective oxidation of 26 utilizing oxidizing agents such as sodium periodate or meta-chloroperbenzoic acid provides the desired sulfoxides or sulfones.

One skilled in the art will recognize that, in some cases, after the introduction of a given reagent as it is depicted in the schemes, it may be necessary to perform additional routine synthetic steps not described in detail to complete the synthesis of Formula (1) compounds.

The present invention includes all veterinary or pharmaceutical acceptable isotopically-labelled Formula (1) compounds wherein one or more atoms are replaced by atoms having the same atomic number, but an atomic mass or mass number different from the atomic mass or mass number usually found in nature.

Examples of isotopes suitable for inclusion in the compounds of the present invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, and sulphur, such as $^{35}S$.

The skilled person will appreciate that the compounds of the present invention could be made by methods other than those herein described as incorporated herein by reference, by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions).

The Formula (1) compounds are useful as antiparasitic agents, therefore, another embodiment of the present invention is a veterinary composition comprising a therapeutically effective amount of a Formula (1) compound, stereoisomer thereof, and at least one veterinary or pharmaceutical acceptable carrier. The compounds of the present invention (including the compositions and processes used therein) may also be used in the manufacture of a medicament for the therapeutic applications described herein.

The compound of the present invention can be administered alone or in a formulation appropriate to the specific use envisaged, the particular species of host animal being treated and the parasite involved. Generally, it will be administered as a formulation in association with at least one veterinary or pharmaceutical acceptable carrier. The term "carrier" is used herein to describe any ingredient (e.g., excipient, diluents, and the like) other than the compound of the present invention or any additional veterinary (e.g., antiparasitic) agent. The choice of carrier will to a large extent depend on factors such as the particular mode of administration, the effect of the carrier on solubility and stability, and the nature of the dosage form. In addition to the excipients, the amount of the compound of the present invention that is administered and the dosage regimen for treating a condition or disorder with the compound depends on a variety of factors, including the age, weight, sex and medical condition of the animal, the severity of the disease, the route and frequency of administration, and thus may vary widely.

In one embodiment, the pharmaceutical composition comprises a Formula (1) compound with at least one veterinary or pharmaceutical acceptable carrier. The concentration range will vary depending on the composition (e.g., oral, topical, or injectable). For an oral dose, the range of active (i.e., compound of the present invention) is about 0.1 to 50 mg/kg, preferably from about 0.5 to 25 mg/kg, and even more preferably from about 0.5 to 10 mg/kg, and most preferably from about 1 to 5 mg/kg. For a topical solution, the range of active is about 0.1 to 1000 mg/mL, and preferably from about 0.5 to 500 mg/mL, and more preferably from about 1 to 250 mg/mL, and even more preferably from about 2 to 200 mg/mL. Depending upon the final volumes of the topical solution(s), the concentration of the active can change from that described above. Generally, injectable doses tend to be, but not always, lower in concentration.

The formulations can be prepared using conventional dissolution and mixing procedures. Such compositions and methods for their preparation may be found, for example, in 'Remington's Veterinary Sciences', 19th Edition (Mack Publishing Company, 1995; and "Veterinary Dosage Forms: Tablets, Vol. 1", by H. Lieberman and L. Lachman, Marcel Dekker, N.Y., 1980 (ISBN 0-8247-6918-X).

A typical formulation is prepared by mixing a Formula (1) compound with at least one veterinary or pharmaceutical acceptable carrier. Suitable carriers are well known to those skilled in the art and include materials such as carbohydrates, waxes, water soluble and/or swellable polymers, hydrophilic or hydrophobic materials, gelatin, oils, solvents, water, and the like. The particular carrier(s) will depend upon the means and purpose for which the compound of the present invention is being applied. Solvents are generally selected based on solvents recognized by persons skilled in the art as safe to be administered to an animal. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or veterinary composition thereof) or aid in the manufacturing of the veterinary product (i.e., medicament). The compound of the present invention will typically be formulated into veterinary dosage forms to provide an easily controllable dosage form for administration.

The methods by which the compound of the present invention may be administered include oral, topical, and injectable (e.g., parenteral and subcutaneous) administration.

The compound of the present invention can be administered orally by capsule, bolus, tablet, powders, lozenges, chews, multi and nanoparticulates, gels, solid solution, films, sprays, or liquid form. This is a preferred method of administration and as such it is desirable to develop the compound for oral administration. Such formulations may be employed as fillers in soft or hard capsules, soft or hard palatable chews, which typically comprise at least one veterinary or pharmaceutical acceptable carrier, for example, water, ethanol, polyethylene glycol, N-methylpyrrolidone, propylene glycol, methylcellulose, or a suitable oil, and one or more emulsifying agents, flavorants, and/or suspending agents. Liquid forms include suspensions, solutions, syrups, drenches and elixirs. Liquid formulations may also be prepared by the reconstitution of a solid, for example, from a sachet. Oral drenches are commonly prepared by dissolving or suspending the compound of the present invention in a suitable medium (e.g. triethylene glycol, benzyl alcohol, and the like). The compound of the present invention can also be formulated with a food substance, e.g., a dietary admixture (food pellets or powder for birds).

The compound of the present invention can be administered topically to the skin or mucosa, that is dermally or transdermally. This is another preferred method of administration and as such it is desirable to develop the compound of the present invention to be suited to such formulations, for example liquid forms. Typical formulations for this purpose include pour-on, spot-on, multi-spot-on, stripe-on, comb-on, roll-on, dip, spray, mousse, shampoo, powder formulation, gels, hydrogels, lotions, solutions, creams, ointments, dusting powders, dressings, foams, films, skin patches, wafers, implants, sponges, fibers, bandages and micro emulsions. Liposomes may also be used. Typical carriers include alcohol, water, mineral oil, liquid petrolatum, white petrolatum, glycerin, N-methyl formamide, glycol monomethyl ethers, polyethylene glycol, propylene glycol, and the like. Penetration enhancers may be incorporated—see, for example, J Pharm Sci, 88 (10), 955-958 by Finnin and Morgan (October 1999). Pour-on or spot-on formulations may be prepared by dissolving the active ingredients in an acceptable liquid carrier such as butyl digol, liquid paraffin or a non-volatile ester, optionally with the addition of a volatile component such as propan-2-ol or a glycol ether. Alternatively, pour-on, spot-on or spray formulations can be prepared by encapsulation, to leave a residue of active agent on the surface of the animal, this effect may ensure that the compound of the present invention has increased persistence of action and is more durable, for example it may be more water-fast. Topical formulations contemplated herein can comprise from about 0.1 mg/kg to 50 mg/kg of a compound of the present invention, and more preferably from about 1 mg/kg to 10 mg/kg of a compound of the present invention, and even more preferably, from 1 mg/kg to 5 mg/kg.

The compounds of the present invention can also be administered topically via a support matrix for example, a synthetic or natural resin, plastic, cloth, leather, or other such polymeric system in the shape of a collar or ear tag. Said collar or ear tag may be coated, impregnated, layered, by any means so as to provide a veterinary or pharmaceutical acceptable amount of a compound of the present invention alone, or with at least one veterinary or pharmaceutical acceptable carrier, and optionally an additional veterinary agent, or veterinary or pharmaceutical acceptable salt thereof. Such formulations are prepared in a conventional manner in accordance with standard medicinal or veterinary practice. Further, these formulations will vary with regard to the weight of active compound contained therein, depending on the species of host animal to be treated, the severity and type of infection or infestation, and the body weight of the animal. The volume of the applied composition can be from about 0.2 mL/kg to 5 mL/kg and preferably from about 1 mL/kg to 3 mL/kg.

Agents may be added to the formulations of the present invention to improve the persistence of such formulations on the surface of the animal to which they are applied, for example to improve their persistence on the coat of the animal. It is particularly preferred to include such agents in a formulation which is to be applied as a pour-on or spot-on formulation. Examples of such agents include acrylic copolymers and in particular fluorinated acrylic copolymers. A particular suitable reagent is the trademark reagent "Foraperle" (Redline Products Inc, Texas, USA). Certain topical formulations may include unpalatable additives to minimize oral exposure.

Injectable (e.g., subcutaneous and parenteral) formulations may be prepared in the form of a sterile solution, which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending compounds of the present invention alone or with at least one additional veterinary agent in the liquid carrier such that the final formulation contains from about 0.01 to 30% by weight of the active ingredients.

Suitable devices for injectable administration include needle (including micro needle) injectors, needle-free injectors and infusion techniques. Injectable formulations are typically aqueous solutions which may contain excipients such as salts, carbohydrates and buffering agents (preferably to a pH of from 3 to 9), but, for some applications, they may be more suitably formulated as a sterile non-aqueous solution or as a dry powder form to be used in conjunction with a suitable vehicle such as sterile, pyrogen-free water. The preparation of injectable formulations under sterile conditions, for example, by lyophilisation, may readily be accomplished using standard veterinary techniques well known to those skilled in the art. The solubility of a compound of the present invention used in the preparation of an injectable solution may be increased by the use of appropriate formulation techniques, such as the incorporation of solubility-enhancing agents.

Administration of the compound of the instant invention is contemplated to be once a month. However, an extended duration formulation may allow for dosing once every 2, 3, 4, 5, or 6 months. A once a year dose is also contemplated.

Such formulations are prepared in a conventional manner in accordance with standard medicinal or veterinary practice. Further, these formulations will vary with regard to the weight of active compound contained therein, depending on the species of host animal to be treated, the severity and type of infection or infestation, and the body weight of the animal.

The composition of the present invention may be administered alone, as described above, or in combination with at least one other additional antiparasitic agent to form a multicomponent parasiticide giving an even broader spectrum of pharmaceutical and/or veterinary utility. Thus, the present invention also envisions a combination veterinary composition comprising an effective amount of the compound of the present invention in combination with at least one other additional antiparasitic agent and can further comprise at least one veterinary or pharmaceutical acceptable carrier.

The following list of additional veterinary agents together with which the compound of the present invention can be used is intended to illustrate the possible combinations, but not to impose any limitation. Non-limiting examples of additional veterinary agents include: amitraz, arylpyrazoles, amino acetonitriles, anthelmintics (e.g., albendazole, cambendazole, dichlorvos, fenbendazole, flubendazole, levamisole, mebendazole, monepantel, morantel, octadepsipeptides, oxantel, oxfendazole, oxibendazole, paraherquamide, parbendazole, piperazines, praziquantel, pyrantel, thiabendazole, tetramisole, triclabendazole, and the like), avermectins and derivatives thereof (e.g., abamectin, doramectin, emamectin, eprinomectin, ivermectin, moxidectin, selamectin, milbemycin, milbemycin oxime, and the like), DEET, demiditraz, diethylcarbamazine, fipronil, insect growth regulators (e.g., lufenuron, novaluron, hydroprene, kinoprene, methoprene, and the like), metaflumizone, niclosamide, nitenpyram, permethrin, pyrethrins, pyriproxyfen, spinosad, and the like. In certain instances, combinations of a compound of the present invention with at least one additional veterinary agent can result in a greater-than-additive effect. Non-limiting examples of combinations include, but are not limited to: compound of the present invention with pyrantel, compound of the present invention with macrocyclic lactone, combination of the present invention with macrocyclic lactone and levamisole, compound of the present invention with macrocyclic lactone and pyrantel.

The veterinary composition for application to an animal may be packaged in a variety of ways depending upon the method used for administering the compound of the present invention or combination, thereof. Generally, an article for distribution includes a container having deposited therein the veterinary composition in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The compounds of the present invention (including the compositions and processes used therein) may also be used in the manufacture of a medicament for the therapeutic applications described herein.

The compounds of the present invention, stereoisomers thereof, and compositions comprising a therapeutically effective amount of a Formula (1) compound and at least one veterinary or pharmaceutical acceptable carrier are useful as ectoparasiticides for the control and treatment of infections or infestations manifested by said ectoparasite in an animal. The compounds of the present invention have utility as an ectoparasiticide, in particular, as an acaricide and insecticide. They may, in particular, be used in the fields of veterinary medicine, livestock husbandry and the maintenance of public health: against acarids, insects, and copepods which are parasitic upon vertebrates, particularly warm-blooded vertebrates, including companion animals, livestock, and fowl and cold-blooded vertebrates like fish. Some non-limiting examples of ectoparasites include: ticks (e.g., *Ixodes* spp., (e.g., *I. ricinus, I. hexagonus*), *Rhipicephalus* spp., (e.g., *R. sanguineus*), *Boophilus* spp., *Amblyomma* spp. (e.g., *A. maculatum, A. triste, A. parvum, A. cajennense, A. ovale, A. oblongoguttatum, A. aureolatum, A. cajennense*), *Hyalomma* spp., *Haemaphysalis* spp., *Dermacentor* spp. (e.g., *D. variabilis, D. andersoni, D. marginatus*), *Ornithodorus* spp., and the like); mites (e.g., *Dermanyssus* spp., *Sarcoptes* spp., (e.g., *S. scabiei*), *Psoroptes* spp., (e.g., *P. bovis*), *Otodectes* spp., *Chorioptes* spp., *Demodex* spp., (e.g., *D. folliculorum, D. canis*, and *D. brevis*) and the like); chewing and sucking lice (e.g., *Damalinia* spp., *Linognathus* spp., *Cheyletiella* spp., *Haematopinus* spp., *Solenoptes* spp., *Trichodectes* spp., *Felicola* spp., and the like); fleas (e.g., *Siphonaptera* spp., *Ctenocephalides* spp., and the like); biting flies, midges, and mosquitos (e.g., *Tabanidae* spp., *Haematobia* spp., *Musca* spp., *Stomoxys* spp., *Dematobia* spp., *Cochliomyia* spp., *Simuliidae* spp., *Ceratopogonidae* spp., *Psychodidae* spp., *Aedes* spp., *Culex* spp., *Anopheles* spp., and the like); bed bugs (e.g., insects within the genus *Cimex* and family Cimicidae); and grubs (e.g., *Hypoderma bovis, H. lineatum*); and copepods (e.g., sea lice within the Order Siphonostomatoida, including genera *Lepeophtheirus* and *Caligus*).

The compound of the present invention can also be used for the treatment of endoparasites, for example, heartworms, roundworms, hookworms, whipworms, and tapeworms. The gastrointestinal roundworms include, for example, *Ostertagia ostertagi* (including inhibited larvae), *O. lyrata, Haemonchus placei, H. similis, H. contortus, Toxocara canis, T. leonina, T. cati, Trichostrongylus axei, T. colubriformis, T. longispicularis, Cooperia oncophora, C. pectinate, C. punctata, C. surnabada* (syn. *mcmasteri*), *C. spatula, Ascaris suum, Hyostrongylus rubidus, Bunostomum phlebotomum, Capillaria bovis, B. trigonocephalum, Strongyloides papillosus, S. ransomi, Oesophagostomum radiatum, O. dentatum, O. columbianum, O. quadrispinulatum, Trichuris* spp., and the like. Other parasites include: hookworms (e.g., *Ancylos-* toma caninum, A. tubaeforme, A. braziliense, Uncinaria stenocephala); lungworms (e.g., Dictyocaulus viviparus and Metastrongylus spp); eyeworms (e.g., Thelazia spp.); parasitic stage grubs (e.g., Hypoderma bovis, H. lineatum, Dermatobia hominis); kidneyworms (e.g., Stephanurus dentatus); screw worm (e.g., Cochliomyia hominivorax (larvae); filarial nematodes of the super-family Filarioidea and the Onchocercidae Family. Non-limiting examples of filarial nematodes within the Onchocercidae Family include the genus *Brugia* spp. (i.e., *B. malayi*, *B. pahangi*, *B. timori*, and the like), *Wuchereria* spp. (i.e., *W. bancrofti*, and the like), *Dirofilaria* spp. (*D. immitis*, *D. repens*, *D. ursi*, *D. tenuis*, *D. spectans*, *D. lutrae*, and the like), *Dipetalonema* spp. (i.e., *D. reconditum*, *D. repens*, and the like), *Onchocerca* spp. (i.e., *O. gibsoni*, *O. gutturosa*, *O. volvulus*, and the like), *Elaeophora* spp. (*E. bohmi*, *E. elaphi*, *E. poeli*, *E. sagitta*, *E. schneideri*, and the like), *Mansonella* spp. (i.e., *M. ozzardi*, *M. perstans*, and the like), and *Loa* spp. (i.e., *L. loa*). In another aspect of the invention, the compound of the present invention is useful for treating endoparasiticidal infection from filarial nematodes within the genus *Dirofilaria* (i.e., *D. immitis*, *D. repens*, *D. ursi*, *D. tenuis*, and the like).

The compounds of the present invention and compositions comprising compounds of the present invention in conjunction with at least one other veterinary agent are of particular value in the control of ectoparasites, endoparasites, and insects which are injurious to, or spread or act as vectors of diseases in companion animals, livestock, birds, and fish. The ectoparasites, insects, and endoparasites which can be treated with a combination of a Formula (1) compound and an additional veterinary agent include those as herein before described and including helminthes of the phylum platyhelminthes (e.g., trematodes, eucestoda, and cestoda), and nemathelminthes (e.g., nematodes).

Any of the compounds of the present invention, or a suitable combination of a compound of the present invention and optionally, with at least one additional veterinary agent may be administered directly to the animal and/or indirectly by applying it to the local environment in which the animal dwells (such as bedding, enclosures, and the like). Direct administration includes contacting the skin, fur, or feathers of a subject animal with the compound(s), or by feeding or injecting the compounds into the animal.

The Formula (1) compound, stereoisomers thereof, and combinations with at least one additional veterinary agent, as described herein, are of value for the treatment and control of the various lifecycle stages of insects and parasites including egg, nymph, larvae, juvenile and adult stages.

The present invention also relates to a method of administering a compound of the present invention alone or in combination with at least one additional veterinary agent, and optionally at least one veterinary or pharmaceutical acceptable carrier, to animals in good health comprising the application to said animal to reduce or eliminate the potential for human parasitic infection or infestation from parasites carried by the animal and to improve the environment in which the animals inhabit.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed using glass-backed silica gel 60 F 254 precoated plates and eluted with appropriate solvent ratios (v/v). Reactions were assayed by TLC or LCMS and terminated as judged by the consumption of starting material. Visualization of the TLC plates was done with UV light (254 nM wavelength) or with an appropriate TLC visualizing solvent and activated with heat. Flash column chromatography (Still et al., *J. Org. Chem.* 43, 2923, (1978) was performed using silica gel (RediSep Rf) or various MPLC systems, such as Biotage or ISCO purification system.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography (TLC), recrystallization, and differential (i.e., liquid-liquid) extraction techniques.

The compound structures in the examples below were confirmed by one or more of the following methods: proton magnetic resonance spectroscopy, and mass spectroscopy. Proton magnetic resonance ($^1$H NMR) spectra were determined using a Bruker spectrometer operating at a field strength of 400 megahertz (MHz). Chemical shifts are reported in parts per million (PPM, δ) downfield from an internal tetramethylsilane standard. Mass spectra (MS) data were obtained using Agilent mass spectrometer with atmospheric pressure chemical ionization. Method: Acquity UPLC with chromatography performed on a Waters BEH C18 column (2.1×50 mm, 1.7 μm) at 50° C. The mobile phase was a binary gradient of acetonitrile (containing 0.1% trifluoroacetic acid) and water (5-100%).

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

The following examples can be prepared according to the schemes and preparations as presented herein.

Intermediate 1. tert-butyl-3'-bromo-1H,5'H-spiro [azetidine-3,7'-furo[3,4,b]pyridine]-1-carboxylate

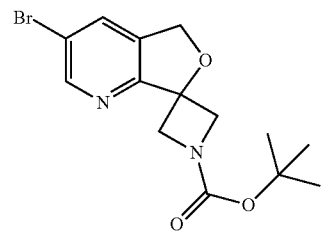 [SMILES: CC(C)(C)OC(=O)N1CC2(C1)OCc1cc(Br)cnc12]

Step 1. 5-bromo-2-iodo-3-methyl-pyridine

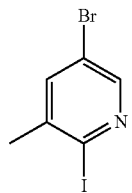

To a stirred solution of 2,5-dibromo-3-methyl-pyridine (20.0 g, 79.7 mmol, 1 eq) in acetonitrile (120 mL) was added acetyl chloride (8.5 mL, 119.5 mmol, 1.5 eq) followed by addition of NaI (47.8 gm, 319 mmol, 4 eq) at room temperature. Resulting reaction mixture was refluxed for 16 hours. After complete consumption of starting material, reaction mixture was quenched with water (200 mL) and extracted with ethyl acetate (3×200 mL). Organic layer was washed with aqueous sodium bicarbonate (2×300 mL), brine (300 mL) and dried over sodium sulfate. Organic layer was concentrated under reduced pressure to afford brown oil (35.5 g, crude). Crude was purified by column chromatography using silica gel (100-200 mesh). Desired compound was eluted at 5% EtOAc in hexane to get title compound as brown oil (22.5 g, 94.78%). $^1$H NMR (400 MHz, CDCl3) δ: 2.36 (s, 3H), 7.56 (d, J=2.4 Hz, 1H), 8.24 (d, J=2.28 Hz, 1H). LC-MS (m/z): 297.9 (M+H).

Step 2. 5-bromo-3-bromomethyl-2-iodo-pyridine

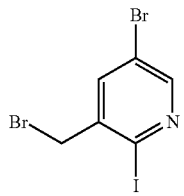

To a stirred solution of 5-bromo-2-iodo-3-methyl-pyridine (22.5 g, 75.5 mmol, 1 eq) in 1,2-dichloroethane (200 mL) was added NBS (20.16 g, 113.255 mmol, 1.5 eq) followed by addition of AIBN (4.96 g, 30.2 mmol, 0.4 eq) at room temperature in dark. Resulting reaction mixture was heated at 80° C. for 16 hours. After maximum consumption of starting material, reaction mixture was cooled to room temperature and quenched with water (150 mL), extracted with DCM (2×150 mL). Combined organic phase was washed with brine (200 mL), dried over anhydrous Na$_2$SO$_4$ and concentrated under reduced pressure to get dark brownish semi solid (25 g, crude). Crude of title compound was used as such for next reaction. $^1$H NMR (400 MHz, CDCl3) δ: (Mixture of starting with product): 4.45 (s, 2H), 7.81 (d, J=2.36 Hz, 1H), 8.31 (d, J=2.36 Hz, 1H). LC-MS (m/z): No ionization.

Step 3. (5-bromo-2-iodo-pyridin-3-yl)-methanol

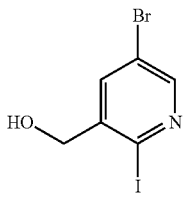

To a stirred solution of 5-bromo-3-bromomethyl-2-iodo-pyridine (25.0 g, crude, 66.313 mmol, 1 eq) in 1,4-dioxane (200 mL) was added suspension of CaCO$_3$ (34.5 mL, 345 mmol, 5.2 eq) in water (200 mL) at room temperature. Resulting reaction mixture was refluxed for 10 hours. After complete consumption of starting material, reaction mixture was cooled to room temperature and filtered through celite bed over Buchner funnel, celite bed was washed with DCM (2×300 mL). Combined filtrate was washed with water (300 mL) and aqueous sodium bicarbonate (120 mL), dried over sodium sulfate and concentrated under reduced pressure to afford off white solid (15.3 g, crude). Crude compound was purified by washing with n-pentane (2×150 mL) to get desired compound as white solid (9.5 g, impure). Impure title compound was used as such for the next reaction. $^1$H NMR (400 MHz, CDCl3) δ: 2.14 (t, J=5.8 Hz, 1H), 4.62 (d, J=5.8, 2H), 7.86 (d, J=1.32 Hz, 1H), 8.33 (d, J=3.32, 1H). LC-MS (m/z): 313.9 (M+H).

Step 4. 3-(5-bromo-3-hydroxymethyl-pyridin-2-yl)-3-hydroxy-azetidine-1-carboxylic acid tert-butyl ester

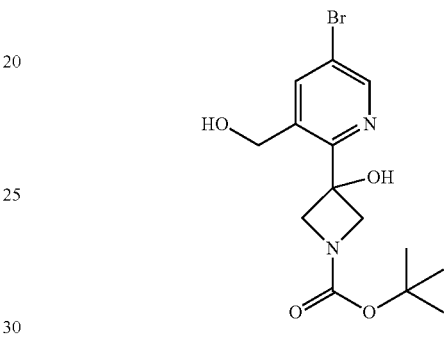

To a stirred solution of (5-bromo-2-iodo-pyridin-3-yl)-methanol (9.5 g, 30.2 mmol, 1 eq) in dry THF (100 mL) was added i-PrMgCl.LiCl complex (1.3M in THF, 55.9 mL, 72.6 mmol, 2.4 eq) at −20° C. in drop wise manner over period of 20 minutes. Predissolved solution of N-boc-3-azetidinone (6.22 g, 36.3 mmol, 1.2 eq) in dry THF (80 mL) was added at −20° C. to above reaction mixture. Resulting reaction mixture was stirred at room temperature for 16 hours under nitrogen atmosphere. After maximum consumption of starting material, reaction mixture was cooled to 0° C. and quenched with 10% citric acid solution (20 mL), diluted with water (150 mL) and extracted with ethyl acetate (3×100 mL). Combined organic phase was washed with brine solution (100 mL), dried over anhydrous Na$_2$SO$_4$ and concentrated under reduced pressure to get yellowish sticky mass (18.2 g, crude). Crude compound was purified by column chromatography by using silica gel (100-200 mesh). Desired compound was eluted by 35% ethyl acetate in hexane to afford title compound as pale yellow thick oil (4.9 g, 45%). $^1$H NMR (400 MHz, CDCl3) δ: 1.43 (s, 9H), 3.12 (s, 1H), 4.13 (d, J=9.92 Hz, 2H), 4.54 (bs, 2H), 4.71-4.73 (m, 3H), 7.93 (d, J=2.12 Hz, 1H), 8.53 (d, J=3.00 Hz, 1H). LC-MS (m/z): 358.9 (M+H).

Step 5. tert-butyl-3'-bromo-1H,5'H-spiro[azetidine-3, 7'-furo[3,4,b]pyridine]-1-carboxylate (Intermediate 1)

To a stirred solution of 3-(5-bromo-3-hydroxymethyl-pyridin-2-yl)-3-hydroxy-azetidine-1-carboxylic acid tert-butyl ester (9.0 g, 25.1 mmol, 1 eq) in dry toluene (80 mL) was added triethyl amine (11.62 mL, 82.7 mmol, 3.3 eq) at 0° C. followed by addition of tosyl anhydride (9.81 g, 30.1 mmol, 1.2 eq). Resulting reaction mixture was stirred at room temperature for 16 hours under nitrogen atmosphere. After complete consumption of starting material, reaction mixture was quenched with saturated Na$_2$CO$_3$ solution (20 mL), diluted with water (20 mL) and extracted with ethyl acetate (2×100 mL). Combined organic phase was washed with brine solution (100 mL), dried over anhydrous $Na_2SO_4$ and concentrated under reduced pressure to get brown sticky mass (13.4 g, crude). Crude compound was purified by column chromatography by using silica gel (100-200 mesh). Desired compound was eluted at 10% ethyl acetate in hexane to afford title compound as white solid (4.5 g, 53%). $^1H$ NMR (400 MHz, CDCl3) δ: 1.44 (s, 9H), 4.21-4.28 (m, 4H), 5.09 (s, 2H), 7.68 (s, 1H), 8.63 (s, 1H). LC-MS (m/z): 340.9 (M+H).

Example 1

3'-[5-(3,5-dichlorophenyl)-5-(trifluoromethyl)-4,5-dihydroisoxazol-3-yl]-1-[(methylsulfonyl)acetyl]-5'H-spiro[azetidin-3,7'-furo[3,4,b]pyridine]

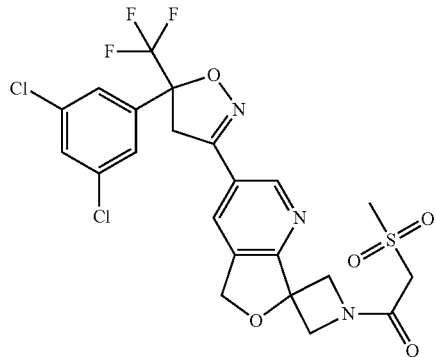 [SMILES: CS(=O)(=O)CC(=O)N1CC2(C1)OCc1cc(C3=NOC(c4cc(Cl)cc(Cl)c4)(C(F)(F)F)C3)cnc12]

Step 1. tert-butyl-3'-formyl-1H,5'H-spiro[azetidine-3,7'-furo[3,4,b]pyridine]-1-carboxylate

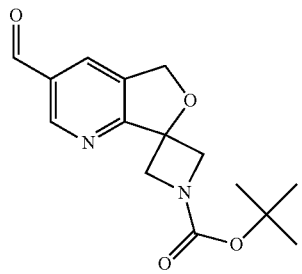 [SMILES: CC(C)(C)OC(=O)N1CC2(C1)OCc1cc(C=O)cnc12]

To a stirred solution of tert-butyl-3'-bromo-1H,5'H-spiro[azetidine-3,7'-furo[3,4,b]pyridine]-1-carboxylate (Intermediate 1, 2 g, 5.7 mmol, 1 eq) in dry THF (30 mL) was added n-BuLi (1.0M in hexane, 6.4 mL, 7.0 mmol, 1.2 eq) at −78° C. and stirred for 10 minutes at −78° C. under nitrogen atmosphere. After 10 minutes, dry DMF (0.68 mL, 8.79 mmol, 1.5 eq) was added at −78° C. Resulting reaction mixture was stirred at −20° C. for 3 hours under nitrogen atmosphere. After complete consumption of starting material, reaction mixture was quenched with 10% $NH_4Cl$ solution (10 mL), diluted with water (50 mL) and extracted with ethyl acetate (2×50 mL). Combined organic phase was washed with brine (40 mL), dried over anhydrous $Na_2SO_4$ and concentrated under reduced pressure to get title compound of brown thick oil (1.7 g, crude). Crude compound was used as such for next reaction. LC-MS (m/z): 291.2 (M+H).

Step 2. tert-butyl-3'-(hydroxyimino)methyl]-1H,5'H-spiro[azetidine-3,7'-furo[3,4,b]pyridine]-1-carboxylate

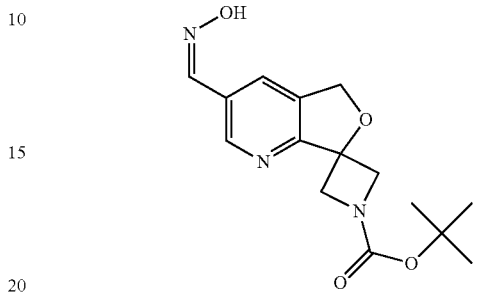

To a stirred solution of tert-butyl-3'-formyl-1H,5'H-spiro[azetidine-3,7'-furo[3,4,b]pyridine]-1-carboxylate (1.7 g, 5.8 mmol, 1 eq) in EtOH (15 mL) was added pyridine (1.0 mL, 12.9 mmol, 2.2 eq) followed by addition of hydroxyl amine hydrochloride (0.60 g, 8.78 mmol, 1.5 eq) at room temperature. Resulting reaction mixture was stirred at room temperature for 16 hours under nitrogen atmosphere. After complete consumption of starting material, reaction mixture was evaporated in vacuo to afford brown colored thick oil, which was diluted by water (70 mL). Aqueous was extracted with ethyl acetate (3×50 mL). Combined organic phase was washed with brine (50 mL), dried over anhydrous $Na_2SO_4$ and concentrated under reduced pressure to get title compound as brown thick oil (1.6 g, crude). Crude compound was used as such for next reaction. LC-MS (m/z): 304.1 (M−H).

Step 3. tert-butyl 3'-[5-(3,5-dichlorophenyl)-5-(trifluoromethyl)-4,5-dihydroisoxazol-3-yl]-5'H-spiro[azetidin-3,7'-furo[3,4,b]pyridine]-1-carboxylate

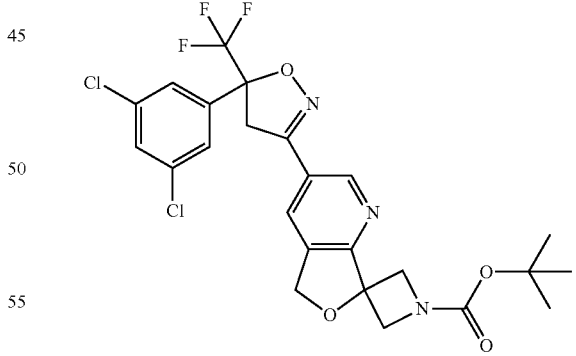

To a stirred solution of tert-butyl-3'-(hydroxyimino)methyl]-1H,5'H-spiro[azetidine-3,7'-furo[3,4,b]pyridine]-1-carboxylate (1.6 g, 5.24 mmol, 1 eq) in dry DMF (23 mL) was added NCS (0.77 g, 5.76 mmol, 1.1 eq) at room temperature and stirred at room temperature for 1 hour in dark. After complete conversion of starting material to chloro intermediate potassium hydrogen carbonate (0.79 g, 7.9 mmol, 1.5 eq) was added followed by addition of 1,3-dichloro-5-(1-trifluoromethyl-vinyl)-benzene (1.52 g, 6.29 mmol, 1.2 eq) in DMF (2 mL) at room temperature. Resulting reaction mixture was stirred at room temperature for 16 hours under nitrogen atmosphere. After complete consumption of starting material, reaction mixture was diluted by water (50 mL). Aqueous was extracted with ethyl acetate (3×50 mL). Combined organic phase was washed with brine (30 mL), dried over anhydrous Na$_2$SO$_4$ and concentrated under reduced pressure to get brown thick oil (1.65 g, crude). Crude compound was purified by column chromatography using silica gel (100-200 mesh). Desired compound was eluted at 12% ethyl acetate:Hexane to get title compound as yellowish sticky mass (1.45 g, impure). Impure compound was used as such for next reaction. $^1$H NMR (400 MHz, CDCl3) δ: 1.45 (s, 9H), 3.72 (d, J=17.12 Hz, 1H), 3.98-4.01 (m, 2H), 4.07 (d, J=17.12 Hz, 1H), 4.26-4.28 (m, 2H), 5.14 (s, 2H), 7.20 (d, J=1.52 Hz, 2H), 7.49 (d, J=1.4 Hz, 1H), 7.97 (d, J=0.92 Hz, 1H), 8.72 (d, J=1.68 Hz, 1H). LC-MS (m/z): 542.1 (M−H).

Step 4. trifluoro acetic acid salt of -1-3'-[5-(3,5-dichlorophenyl)-5-(trifluoromethyl)-4,5-dihydroisoxazol-3-yl]-5'H-spiro[azetidin-3,7'-furo[3,4,b]pyridine]

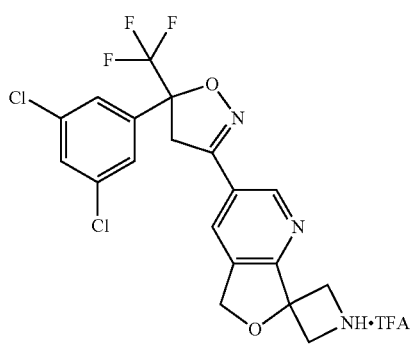

To a stirred solution of tert-butyl 3'-[5-(3,5-dichlorophenyl)-5-(trifluoromethyl)-4,5-dihydroisoxazol-3-yl]-5'H-spiro[azetidin-3,7'-furo[3,4,b]pyridine]-1-carboxylate (1.45 g, 2.6 mmol, 1 eq) in DCM (20 mL) was added TFA (4 mL, 20% v/v) at 0° C. Resulting reaction mixture was stirred at room temperature for 2 hours. After complete consumption of starting material, reaction mixture was evaporated in vacuo to afford brown thick oil, which was striped with chloroform (2×50 mL) and triturated with chloroform:hexane (1:10) to get title compound is off white solid as TFA salt (1.4 g, crude). Crude was used as such for next reaction. LC-MS (m/z): 443.8 (M+H).

Step 5. 3'-[5-(3,5-dichlorophenyl)-5-(trifluoromethyl)-4,5-dihydroisoxazol-3-yl]-1-[(methylsulfonyl)acetyl]-5'H-spiro[azetidin-3,7'-furo[3,4,b]pyridine]

Example 1

To a stirred solution of trifluoro acetic acid salt of 3'-[5-(3,5-dichlorophenyl)-5-(trifluoromethyl)-4,5-dihydroisoxazol-3-yl]-5'H-spiro[azetidin-3,7'-furo[3,4,b]pyridine] (0.7 g, 1.577 mmol, 1 eq) in dry DMF (10 mL) was added EDC.HCl (0.45 g, 2.36 mmol, 1.5 eq) followed by addition of HOBt (0.21 g, 1.58 mmol, 1.0 eq), triethyl amine (1.10 mL, 7.9 mmol, 5.0 eq) and methane sulfonyl-acetic acid (0.44 g, 3.15 mmol, 2 eq) at room temperature. Resulting brown colored reaction mixture was stirred at room temperature for 16 hours under nitrogen atmosphere. After complete consumption of starting material, reaction mixture was quenched by water (30 mL), extracted with ethyl acetate (3×30 mL). Combined organic phase was washed with saturated LiCl solution (30 mL), brine (30 mL), dried over anhydrous Na$_2$SO$_4$ and concentrated under reduced pressure to get brown sticky mass (0.5 g, crude). Crude compound was purified by column chromatography using silica gel (100-200 mesh). Desired compound was eluted at 1% methanol:DCM to get faint brown colored thick oil, which was triturated with pentane (20 mL), diethyl ether (20 mL) to get faint brown colored solid. Brown colored solid was recrystallised with chloroform:hexane (1:10) to get title compound as off white solid (195 mg, 21%). $^1$H NMR (400 MHz, CDCl3) δ: 3.17 (s, 3H), 3.70 (d, J=17.24 Hz, 1H), 3.85 (s, 2H), 4.09 (d, J=17.2 Hz, 1H), 4.39-4.48 (m, 2H), 4.65-4.70 (m, 2H), 5.18 (s, 2H), 7.43-7.44 (m, 1H), 7.49 (s, 2H), 8.0 (s, 1H), 8.73 (s, 1H). LC-MS (m/z): 563.8 (M+H).

Example 2

3'-[5-(3,5-dichloro-4-fluorophenyl)-5-(trifluoromethyl)-4,5-dihydroisoxazol-3-yl]-1-[(methylsulfonyl)acetyl]-5'H-spiro[azetidin-3,7-furo[3,4,b]pyridine]

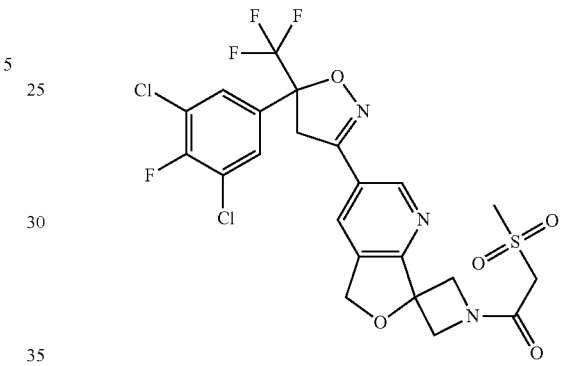

This compound was prepared similarly to Example 1, except that 1,3-dichloro-2-fluoro-5-(1-trifluoromethyl-vinyl)-benzene was used in place of 1,3-dichloro-5-(1-trifluoromethyl-vinyl)-benzene. Yield 82 mg (26%). $^1$H NMR (400 MHz, CDCl3) δ: 3.17 (s, 3H), 3.71 (d, J=17.28 Hz, 1H), 3.85 (s, 2H), 4.10 (d, J=17.16 Hz, 1H), 4.42-4.45 (m, 2H), 4.67-4.68 (m, 2H), 5.18 (s, 2H), 7.57 (d, J=5.96 Hz, 2H), 8.0 (s, 1H), 8.73 (s, 1H). LC-MS (m/z): 581.9 (M+H).

Example 3

1-[(methylsulfonyl)acetyl]-3'-[5-(3,4,5-trichlorophenyl)-5-(trifluoromethyl)-4,5-dihydroisoxazol-3-yl]-5'H-spiro[azetidin-3,7'-furo[3,4,b]pyridine]

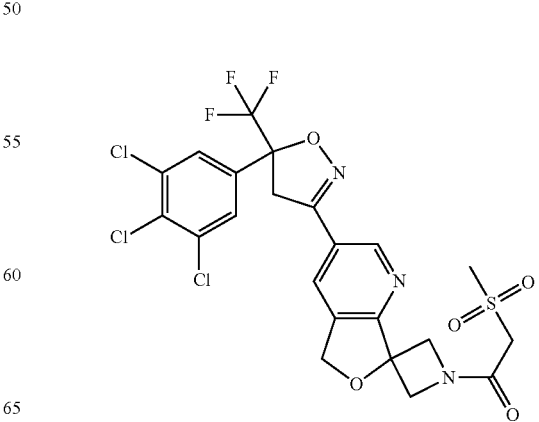

This compound was prepared similarly to Example 1 except that 1,2,3-trichloro-5-(1-trifluoromethyl-vinyl)-benzene was used in place of 1,3-dichloro-5-(1-trifluoromethyl-vinyl)-benzene. Yield 88 mg (16%). ¹H NMR (400 MHz, CDCl3) δ: 3.17 (s, 3H), 3.71 (d, J=17.24 Hz, 1H), 3.85 (s, 2H), 4.10 (d, J=17.28 Hz, 1H), 4.39-4.48 (m, 2H), 4.67-4.68 (m, 2H), 5.18 (s, 2H), 7.62 (s, 2H), 8.0 (s, 1H), 8.73 (s, 1H). LC-MS (m/z): 598.7 (M+H).

Example 4

3'-[5-(3,5-dichloro-4-fluorophenyl)-5-(trifluoromethyl)-4,5-dihydroisoxazol-3-yl]-1-isobutyryl-5'H-spiro[azetidin-3,7'-furo[3,4,b]pyridine]

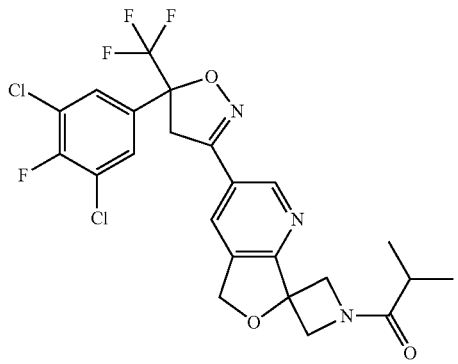 [SMILES: CC(C)C(=O)N1CC2(C1)OCc1cc(C3=NOC(c4cc(Cl)c(F)c(Cl)c4)(C(F)(F)F)C3)cnc12]

This compound was prepared similarly to Example 2 except that isobutyric acid was in place of methane sulfonyl acetic acid. Yield 67 mg (10%). ¹H NMR (400 MHz, CDCl3) δ: 1.13-1.16 (m, 6H), 2.47-2.54 (m, 1H), 3.71 (d, J=17.28 Hz, 1H), 4.09 (d, J=17.24 Hz, 1H), 4.30 (d, J=10.32 Hz, 1H), 4.36 (d, J=11.68 Hz, 1H), 4.44 (d, J=9.04 Hz, 1H), 4.52 (d, J=9.20 Hz, 1H), 5.17 (d, J=2.88 Hz, 2H), 7.57 (d, J=5.96 Hz, 2H), 7.99 (s, 1H), 8.71 (d, J=2.04 Hz, 1H). LC-MS (m/z): 529.8 (M−H).

Example 5

3'-[5-(3,5-dichlorophenyl)-5-(trifluoromethyl)-4,5-dihydroisoxazol-3-yl]-1-isobutyryl-5'H-spiro[azetidin-3,7'-furo[3,4,b]pyridine]

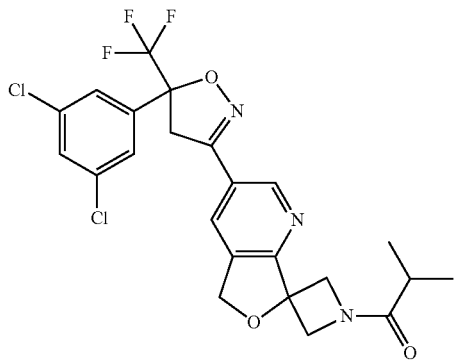 [SMILES: CC(C)C(=O)N1CC2(C1)OCc1cc(C3=NOC(c4cc(Cl)cc(Cl)c4)(C(F)(F)F)C3)cnc12]

This compound was prepared similarly to Example 1 except that isobutyric acid was used in place of methane sulfonyl acetic acid. Yield 118 mg (14%). ¹H NMR (400 MHz, CDCl3) δ: 1.13-1.15 (m, 6H), 2.47-2.52 (m, 1H), 3.72 (dd, J₁=17.28 Hz, J₂=2.32 Hz, 1H), 4.09 (dd, J₁=17.24 Hz, J₂=1.56 Hz, 1H), 4.29 (d, J=10.48 Hz, 1H), 4.36 (d, J=10.40 Hz, 1H), 4.44 (d, J=8.96 Hz, 1H), 4.53 (d, J=8.88 Hz, 1H), 5.13-5.17 (m, 2H), 7.43 (s, 1H), 7.49 (s, 2H), 7.99 (d, J=2.64 Hz, 1H), 8.72 (d, J=2.64 Hz, 1H). LC-MS (m/z): 514.1 (M+H).

Example 6

1-isobutyryl-3'-[5-(3,4,5-trichlorophenyl)-5-(trifluoromethyl)-4,5-dihydroisoxazol-3-yl]-5'H-spiro[azetidin-3,7'-furo[3,4,b]pyridine]

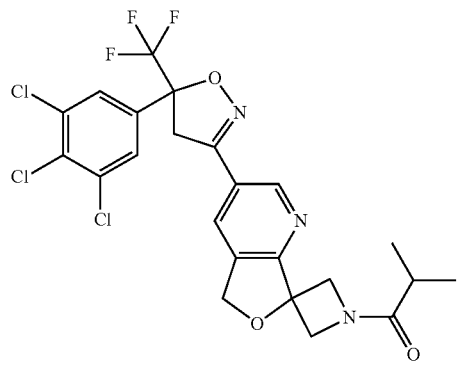 [SMILES: CC(C)C(=O)N1CC2(C1)OCc1cc(C3=NOC(c4cc(Cl)c(Cl)c(Cl)c4)(C(F)(F)F)C3)cnc12]

This compound was prepared similarly to Example 3 except that isobutyric acid was used in place of methane sulfonyl acetic acid. Yield 90 mg (17%). ¹H NMR (400 MHz, CDCl3) δ: 1.13-1.16 (m, 6H), 2.47-2.54 (m, 1H), 3.71 (dd, J₁=17.04 Hz, J₂=2.52 Hz, 1H), 4.10 (dd, J₁=17.32 Hz, J₂=2.0 Hz, 1H), 4.29 (d, J=10.52 Hz, 1H), 4.36 (d, J=10.52 Hz, 1H), 4.44 (d, J=9.16 Hz, 1H), 4.52 (d, J=8.84 Hz, 1H), 5.14-5.21 (m, 2H), 7.63 (s, 2H), 7.98 (s, 1H), 8.71 (s, 1H). LC-MS (m/z): 547.9 (M−H).

Intermediate 2. tert-butyl 2'-chloro-1H,7'H-spiro[azetidine-3,5'-furo[3,4-b]pyridine]-1-carboxylate

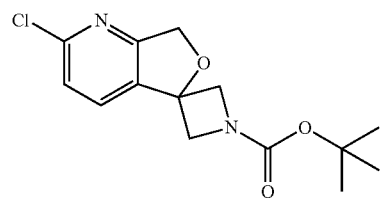 [SMILES: CC(C)(C)OC(=O)N1CC2(C1)OCc1nc(Cl)ccc12]

Step 1. 5-iodo-6-methyl-pyridin-2-ylamine

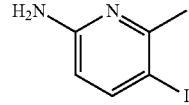

To a stirred solution of 6-methyl-pyridin-2-ylamine (30 g, 278 mmol, 1 eq) in acetic acid (167 mL) was added periodic acid (12.7 g, 55.6 mmol, 0.2 eq) followed by addition of sulphuric acid (4.8 mL, 90.8 mmol, 0.34 eq), water (33 mL) and iodine (28.7 g, 111 mmol, 0.4 eq) at room temperature. Resulting reaction mixture was heated at 80° C. for 6 hours. After complete consumption of starting material, reaction mixture was cooled and poured into sodium thiosulfate solution (200 mL), reddish oil was settled down at the bottom. Reaction mixture was decanted from reddish oil, and filtrate was basified with 50% sodium hydroxide solution (100 mL), yellow colored solid was formed. Resulting solid was extracted with diethyl ether (2×200 mL) and dried over sodium sulfate. Organic layer was concentrated under reduced pressure to afford brown semi solid (60 g, crude). Crude was purified by column chromatography using silica gel (100-200 mesh). Desired compound was eluted at 15% EtOAc in hexane to get title compound as faint brown solid (50 g, 77%). $^1$H NMR (400 MHz, CDCl3) δ: 2.52 (s, 3H), 4.43 (bs, 2H), 6.09 (d, J=8.4 Hz, 1H), 7.65 (d, J=8.44 Hz, 1H). LC-MS (m/z): 235.3 (M+H).

Step 2. 6-chloro-3-iodo-2-methyl-pyridine

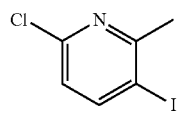

To a stirred solution of concentrated hydrochloride acid (233 mL) at 0° C. was added 5-iodo-6-methyl-pyridin-2-ylamine (25 g, 107 mmol, 1 eq) followed by addition of pre-dissolved sodium nitrite (29.5 g, 427 mmol, 4 eq) in water (150 mL) in drop wise manner over period of 30 minutes. Resulting reaction mixture was stirred at room temperature for 16 hours. After complete consumption of starting material, reaction mixture was cooled to 0° C., and pH was adjusted to 12 by saturated aqueous sodium hydroxide solution, extracted with DCM (3×200 mL). Combined organic layer was dried over anhydrous Na$_2$SO$_4$ and concentrated under reduced pressure to get brown oil (20 g, crude). Crude was purified by column chromatography using silica gel (100-200 mesh). Desired compound was eluted at 4% ethyl acetate in hexane to get title compound as brown oil (8 g, 30%). $^1$H NMR (400 MHz, CDCl3) δ: 2.69 (s, 3H), 6.88 (d, J=8.04 Hz, 1H), 7.95 (d, J=8.24 Hz, 1H). LC-MS (m/z): 254.0 (M+H).

Step 3. 2-bromomethyl-6-chloro-3-iodo-pyridine

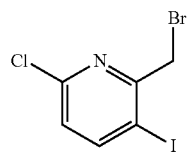

To a stirred solution of 6-chloro-3-iodo-2-methyl-pyridine (20 g, 79 mmol, 1 eq) in 1,2-dichloroethane (200 mL) was added NBS (21.1 g, 118.6 mmol, 1.5 eq) followed by addition of AIBN (5.2 g, 31.6 mmol, 0.4 eq) at room temperature in dark. Resulting reaction mixture was heated at 80° C. for 16 hours. After maximum consumption of starting material, reaction mixture was cooled to room temperature and quenched with water (50 mL), extracted with DCM (3×50 mL). Combined organic phase was washed with brine (50 mL), dried over anhydrous Na$_2$SO$_4$ and concentrated under reduced pressure to get dark brown semi solid (20 g, crude). Crude of title compound was used as such for next reaction. $^1$H NMR not clean. LC-MS: No ionization.

Step 4. (6-chloro-3-iodo-pyridin-2-yl)-methanol

To a stirred solution of 2-bromomethyl-6-chloro-3-iodo-pyridine (20 g, crude, 60 mmol, 1 eq) in 1,4-dioxane (200 mL) was added suspension of CaCO$_3$ (31.4 g, 313 mmol, 5.2 eq) in water (200 mL) at room temperature. Resulting reaction mixture was refluxed for 10 hours. After complete consumption of starting material, reaction mixture was cooled to room temperature and filtered through celite bed over Buchner funnel. Celite bed was washed with EtOAc (2×100 mL). Combined filtrate was washed with water (100 mL) and aqueous sodium bicarbonate (50 mL), dried over sodium sulfate and concentrated under reduced pressure to afford brown solid (21 g, crude). Crude was purified by column chromatography using silica gel (100-200 mesh). Desired compound was eluted at 20% EtOAc in hexane to get title compound as faint yellow solid (2.9 g, 18%) and also 9 g of 6-chloro-3-iodo-2-methyl-pyridine was recovered. $^1$H NMR (400 MHz, CDCl3) δ: 3.87 (t, J=4.9 Hz, 1H), 4.63 (d, J=4.96 Hz, 2H), 7.04 (d, J=4 Hz, 1H), 8.0 (d, J=8.2 Hz, 1H). LC-MS (m/z): 270.1 (M+H).

Step 5. 6-Chloro-2-chloromethyl-3-iodo-pyridine

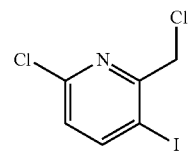

To a stirred solution of (6-chloro-3-iodo-pyridin-2-yl)-methanol (2.5 g, 9.3 mmol, 1 eq) in DCM (25 mL) was added thionyl chloride (0.68 mL, 9.3 mmol, 1 eq) in drop wise manner at 0° C. under nitrogen atmosphere. Resulting reaction mixture was stirred at room temperature for 16 hours. After complete consumption of starting material, reaction mixture was cooled to 0° C. and quenched by aqueous sodium bicarbonate (25 mL), extracted with DCM (3×70 mL). Combined organic phase was dried over anhydrous Na$_2$SO$_4$ and concentrated under reduced pressure to get brown semisolid (2.5 g, crude). Crude title compound was used as such for the next reaction. $^1$H NMR not clean. LC-MS: No ionization.

Step 6. 3-(6-chloro-2-chloromethyl-pyridin-3-yl)-3-hydroxy-azetidine-1-carboxylic acid tert-butyl ester

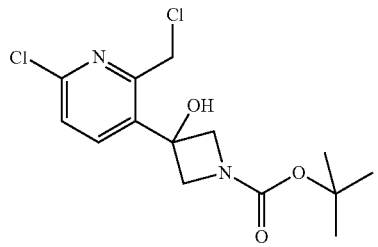 [SMILES: CC(C)(C)OC(=O)N1CC(O)(c2ccc(Cl)nc2CCl)C1]

To a stirred solution of 6-chloro-2-chloromethyl-3-iodopyridine (2.5 g, 8.7 mmol, 1 eq) in dry THF (25 mL) was added i-PrMgCl.LiCl complex (1.3M in THF, 7.37 mL, 9.6 mmol, 1.1 eq) at −20° C. in drop wise manner over period of 10 minutes. Pre-dissolved solution of N-boc-3-azetidinone (1.78 g, 10.4 mmol, 1.2 eq) in dry THF (10 mL) was added at −20° C. to above reaction mixture. Resulting reaction mixture was stirred at room temperature for 16 hours under nitrogen atmosphere. After maximum consumption of starting material, reaction mixture was cooled to 0° C., quenched with 10% citric acid solution (20 mL) and extracted with ethyl acetate (3×100 mL). Combined organic phase was dried over anhydrous $Na_2SO_4$ and concentrated under reduced pressure to get brown oil (4.5 g, crude). Crude of title compound was used as such for next reaction. LC-MS (m/z): 332.9 (M+H).

Step 7. tert-butyl 2'-chloro-1H,7'H-spiro[azetidine-3, 5'-furo[3,4-b]pyridine]-1-carboxylate (Intermediate 2)

To a stirred solution of 3-(6-chloro-2-chloromethyl-pyridin-3-yl)-3-hydroxy-azetidine-1-carboxylic acid tert-butyl ester (4.5 g, 13.5 mmol, 1 eq) in methanol (20 mL) and THF (20 mL) at room temperature was added $K_2CO_3$ (9.35 g, 67.8 mmol, 5 eq). Resulting reaction mixture was stirred at room temperature for 16 hours under nitrogen atmosphere. After complete consumption of starting material, reaction mixture was filtered through celite bed over Buchner funnel, celite bed was washed with THF:methanol (100 mL each). Combined filtrate was concentrated under reduced pressure to get brown oil (crude). Crude compound was purified by column chromatography by using silica gel (100-200 mesh). Desired compound was eluted at 18% ethyl acetate in hexane to afford title compound as off white solid (0.9 g, 22%). $^1$H NMR (400 MHz, CDCl3) δ: 1.46 (s, 9H), 4.08 (d, J=10.0 Hz, 2H), 4.32 (d, J=10.04 Hz, 2H), 5.04 (s, 2H), 7.31 (d, J=8.08 Hz, 1H), 7.73 (d, J=8.08 Hz, 1H). LC-MS (m/z): 297.4 (M+H).

Example 7

1-(2'-(5-(3,5-dichloro-4-fluorophenyl)-5-(trifluoromethyl)-4,5-dihydroisoxazol-3-yl)-7'H-spiro[azetidine-3,5'-furo[3,4-b]pyridine]-1-yl)-2-(methylsulfonyl)ethanone

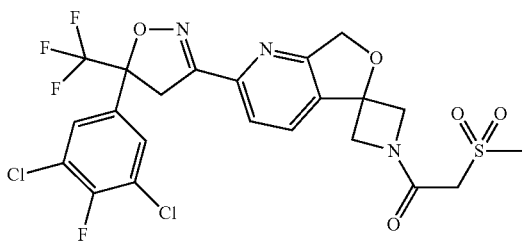 [SMILES: CS(=O)(=O)CC(=O)N1CC2(C1)OCc1nc(C3=NOC(c4cc(Cl)c(F)c(Cl)c4)(C(F)(F)F)C3)ccc12]

Step 1. 1-tert-butyl 2'-ethyl-7'H-spiro[azetidine-3,5'-furo[3,4-b]pyridine]-1,2'-dicarboxylate

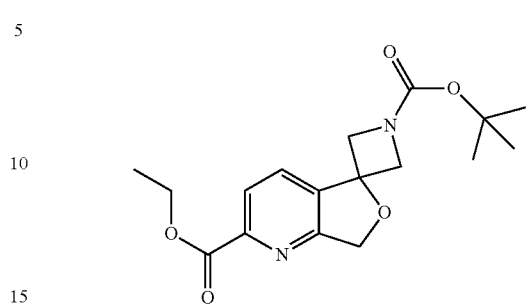

To a stirred solution of tert-butyl 2'-chloro-7'H-spiro[azetidine-3,5'-furo[3,4-b]pyridine]-1-carboxylate (Intermediate 2, 2 g, 6.8 mmol, 1 eq.) in ethanol (30 mL) was added NaOAc (1.11 g, 13.5 mmol, 2 eq.) and reaction mixture was degassed by nitrogen for 30 minutes in 100 mL autoclave vessel. After degassing, palladium acetate (15 mg, 0.068 mmol, 0.01 eq.), dppf (0.112 g, 0.20 mmol, 0.03 eq) was added. Resulting reaction mixture was heated at 80° C. under 225 psi pressure of CO gas for 12 hours. After complete consumption of starting material, reaction mixture was filtered through celite bed; celite bed was washed with ethanol (3×50 mL). Combined filtrate was concentrated under reduced pressure to afford brown oil (2.5 g, crude). Crude compound was purified by column chromatography in 100-200 mesh silica gel, title compound was eluted in 35% ethyl acetate in hexanes to afford title compound as yellow semisolid (1.8 g, 80%). $^1$H NMR (400 MHz, CDCl3) δ: 1.40 (t, J=7.12 Hz, 3H), 1.46 (s, 9H), 4.12 (d, J=9.72 Hz, 2H), 4.34 (d, J=9.72 Hz, 2H), 4.50 (q, J=7.12 Hz, 2H), 5.14 (s, 2H), 7.9 (d, J=7.92 Hz, 1H), 8.14 (d, J=7.88 Hz, 1H). LC-MS (m/z): 335.0 (M+H).

Step 2. tert-butyl 2'-formyl-7'H-spiro[azetidine-3,5'-furo[3,4-b]pyridine]-1-carboxylate

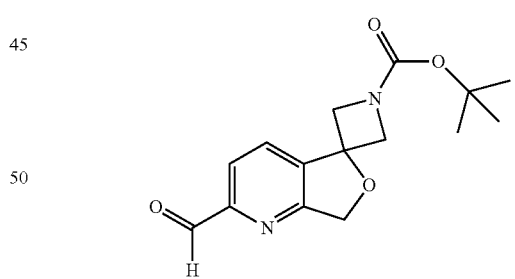

To the stirred solution of 1-tert-butyl 2'-ethyl-7'H-spiro[azetidine-3,5'-furo[3,4-b]pyridine]-1,2'-dicarboxylate (0.5 g, 1.5 mmol, 1 eq.) in DCM (18 mL) at −78° C. under nitrogen atmosphere was added 25% DIBAL-H in toluene (0.64 g, 2.6 mL, 4.5 mmol, 3 eq.). Resulting reaction mixture was stirred at −78° C. for 1 hour under nitrogen atmosphere. After complete consumption of starting material, reaction mixture was quenched by methanol (1.5 mL) followed by addition of saturated solution of sodium potassium tartarate salt (10 mL) at −78° C. and extracted with DCM (3×75 mL). Combined organic layer was dried over sodium sulphate, concentrated under reduced pressure to afford the title compound as brown solid (0.25 g, crude). Crude compound was used as such for the next reaction. LC-MS (m/z): 291.0 (M+H).

Step 3. tert-butyl 2'-((hydroxyimino)methyl)-7'H-spiro[azetidine-3,5'-furo[3,4-b]pyridine]-1-carboxylate

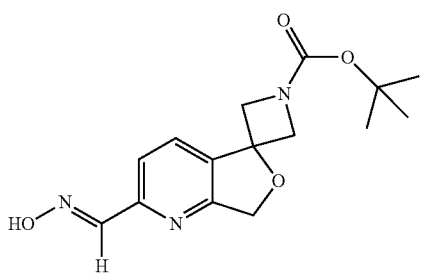 [SMILES: CC(C)(C)OC(=O)N1CC2(C1)OCc1nc(/C=N/O)ccc12]

To a stirred solution of tert-butyl 2'-formyl-7'H-spiro[azetidine-3,5'-furo[3,4-b]pyridine]-1-carboxylate (0.5 g, 1.7 mmol, 1 eq.) in mixture of methanol (12 mL):water (12 mL) was added NaOAc (0.28 g, 3.45 mmol, 2 eq.) followed by addition of NH$_2$OH.HCl (0.24 g, 3.45 mmol, 2 eq.) at room temperature. Resulting reaction mixture was stirred at room temperature for 18 hours under nitrogen atmosphere. After complete consumption starting material, reaction mixture was concentrated under reduced pressure; resulting residue was diluted with water (50 mL) and extracted by ethyl acetate (3×100 mL). Combined organic layer was dried over sodium sulphate and concentrated under reduced pressure to afford title compound as brown solid (0.520 g, 99%). $^1$H NMR (400 MHz, CDCl3) δ: 1.47 (s, 9H), 4.12 (d, J=9.88 Hz, 2H), 4.34 (d, J=10.12 Hz, 2H), 5.08 (s, 2H), 7.73 (d, J=7.92 Hz, 1H), 7.79 (d, J=7.96 Hz, 1H), 8.21 (s, 1H). LC-MS (m/z): 306.3 (M+H).

Step 4. tert-butyl 2'-(5-(3,5-dichloro-4-fluorophenyl)-5-(trifluoromethyl)-4,5-dihydroisoxazol-3-yl)-7'H-spiro[azetidine-3,5'-furo[3,4-b]pyridine]-1-carboxylate

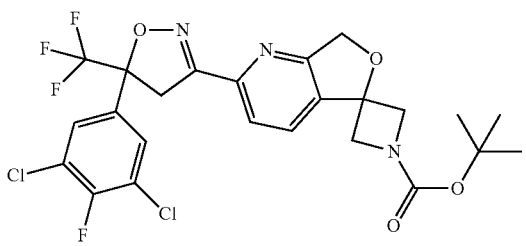 [SMILES: CC(C)(C)OC(=O)N1CC2(C1)OCc1nc(C3=NOC(c4cc(Cl)c(F)c(Cl)c4)(C(F)(F)F)C3)ccc12]

To a stirred solution of tert-butyl 2'-((hydroxyimino)methyl)-7'H-spiro[azetidine-3,5'-furo[3,4-b]pyridine]-1-carboxylate (0.520 g, 1.705 mmol, 1 eq) in DMF (12 mL) was added NCS (0.272 g, 2.046 mmol, 1.2 eq) at room temperature in dark under nitrogen atmosphere. Resulting reaction mixture was stirred at 45° C. for 1 hour. After chloro intermediate formation, 1,3-dichloro-2-fluoro-5-(1-trifluoromethyl-vinyl)-benzene (0.530 g, 2.046 mmol, 1.2 eq) was added followed by addition of KHCO$_3$ (0.255 g, 2.557 mmol, 1.5 eq). Resulting reaction mixture was stirred at room temperature for 16 hours in dark under nitrogen atmosphere. After complete consumption of chloro intermediate, reaction mixture was quenched with water (100 mL) and extracted with ethyl acetate (3×100 mL). Combined organic layer was dried over anhydrous Na$_2$SO$_4$ and concentrated under reduced pressure to get brown thick oil (1.2 g, Crude). Crude compound was purified by column chromatography in 100-200 mesh size silica gel. Desired compound was eluted in 10% ethylacetate in hexanes to afford title compound as white semisolid (0.800 g, impure). Impure compound was used as such for next reaction. $^1$H NMR (400 MHz, CDCl3) δ: 1.46 (s, 9H), 3.84 (d, J=18.2 Hz, 1H), 4.10 (dd, J$_1$=2.54 Hz, J$_2$=9.5 Hz, 2H), 4.22 (d, J=18.16 Hz, 1H), 4.33 (dd, J$_1$=3 Hz, J$_2$=9.44 Hz, 2H), 5.02-5.10 (m, 2H), 7.56 (d, J=6 Hz, 2H), 7.84 (d, J=8.04 Hz, 1H), 8.03 (d, J=8.04 Hz, 1H). LC-MS (m/z): 59.6 (M−H).

Step 5. trifluoro acetic acid salt of 2'-(5-(3,5-dichloro-4-fluorophenyl)-5-(trifluoromethyl)-4,5-dihydroisoxazol-3-yl)-7'H-spiro[azetidine-3,5'-furo[3,4-b]pyridine]

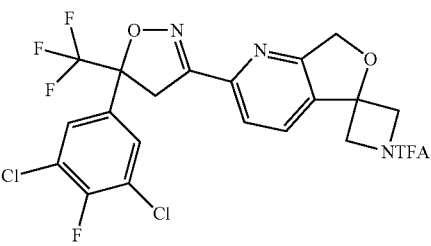

To a stirred solution of tert-butyl 2'-(5-(3,5-dichloro-4-fluorophenyl)-5-(trifluoromethyl)-4,5-dihydroisoxazol-3-yl)-7'H-spiro[azetidine-3,5'-furo[3,4-b]pyridine]-1-carboxylate (0.7 g, 1.248 mmol, 1 eq) in DCM (20 mL) was added TFA (1.911 mL, 24.955 mmol, 20 eq) at 0° C. under nitrogen atmosphere. Resulting reaction mixture was stirred at room temperature for 16 hours. After complete consumption of starting material, reaction mixture was concentrated under reduced pressure, resulting residue was stripped out by chloroform (3×5 mL) to afford title compound as brown semi solid (0.7 g, crude). Crude compound was used as it is for next step reaction. LC-MS (m/z): 461.7 (M+H).

Step 6. 1-(2'-(5-(3,5-dichloro-4-fluorophenyl)-5-(trifluoromethyl)-4,5-dihydroisoxazol-3-yl)-7'H-spiro[azetidine-3,5'-furo[3,4-b]pyridine]-1-yl)-2-(methylsulfonyl)ethanone Example 7

To the stirred solution of trifluoro acetic acid salt of 2'-(5-(3,5-dichloro-4-fluorophenyl)-5-(trifluoromethyl)-4,5-dihydroisoxazol-3-yl)-7'H-spiro[azetidine-3,5'-furo[3,4-b]pyridine] (0.35 g, 0.609 mmol, 1 eq) in DMF (12 mL) was added TEA (0.677 mL, 4.87 mmol, 8 eq) followed by addition of EDC.HCl (0.174 g, 0.913 mmol, 1.5 eq), HOBt (0.082 g, 0.609 mmol, 1 eq) and stirred at room temperature under nitrogen atmosphere for 15 minutes. Methane sulfonyl-acetic acid (0.168 g, 1.217 mmol, 2 eq) was added and resulting reaction mixture was stirred at room temperature for 18 hours. After complete consumption of starting material, reaction mixture was quenched by water (100 mL), extracted with ethyl acetate (3×100 mL). Combined organic layer was washed by saturated LiCl solution (2×30 mL), dried over sodium sulphate and concentrated under reduced pressure to afford brown oil (400 mg, crude). Crude was purified by column chromatography in 100-200 mesh silica gel. Desired compound was eluted in 60% ethyl acetate in hexanes to afford light brown solid (130 mg), which was recrystallised by Chloroform (0.5 mL) in hexanes (5 mL) to afford title compound as off white solid (0.085 g, 23.98%). $^1$H NMR (400 MHz, CDCl3) δ: 3.20 (s, 3H), 3.81-3.85 (m, 3H), 4.22 (d, J=18.16 Hz, 1H), 4.34 (dd, $J_1$=3.24 Hz, $J_2$=11.16 Hz, 1H), 4.45 (dd, $J_1$=2.48 Hz, $J_2$=11.24 Hz, 1H), 4.68 (s, 2H), 5.05-5.14 (m, 2H), 7.57 (d, J=6 Hz, 2H), 7.91 (d, J=8.12 Hz, 1H), 8.05 (d, J=8.08 Hz, 1H). LC-MS (m/z): 580.2 (M−H).

Example 8

1-(2'-(5-(3,5-dichlorophenyl)-5-(trifluoromethyl)-4,5-dihydroisoxazol-3-yl)-7'H-spiro[azetidine-3,5'-furo[3,4-b]pyridine]-1-yl)-2-(methylsulfonyl)ethanone

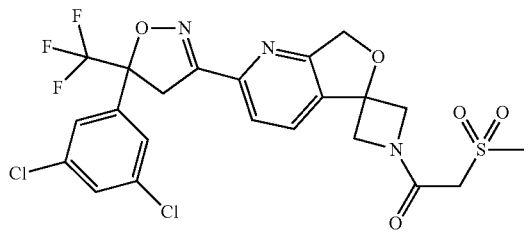 [SMILES: CS(=O)(=O)CC(=O)N1CC2(C1)OCc1nc(C3=NOC(c4cc(Cl)cc(Cl)c4)(C(F)(F)F)C3)ccc12]

This compound was prepared similarly to Example 7 except that 1,3-dichloro-5-(1-trifluoromethyl-vinyl)-benzene was used in place of 1,3-dichloro-2-fluoro-5-(1-trifluoromethyl-vinyl)-benzene to afford title compound as pale yellow solid (42 mg, 12%). $^1$H NMR (400 MHz, CDCl3) δ: 3.18 (s, 3H), 3.81-3.86 (m, 3H), 4.22 (d, J=18.24 Hz, 1H), 4.34 (dd, $J_1$=2.84 Hz, $J_2$=11.24 Hz, 1H), 4.45 (dd, $J_1$=2.44 Hz, $J_2$=11.08 Hz, 1H), 4.68 (s, 2H), 5.05-5.14 (m, 2H), 7.41 (t, J=1.68 Hz, 1H), 7.49-7.5 (m, 2H), 7.91 (d, J=8.08 Hz, 1H), 8.05 (d, J=8.08 Hz, 1H). LC-MS (m/z): 562.0 (M−H).

Example 9

2-(methylsulfonyl)-1-(2'-(5-(3,4,5-trichlorophenyl)-5-(trifluoromethyl)-4,5-dihydroisoxazol-3-yl)-7'H-spiro[azetidine-3,5'-furo[3,4-b]pyridine]-1-yl)ethanone

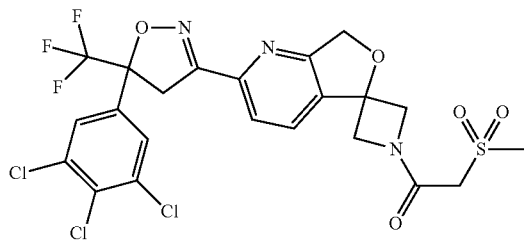 [SMILES: CS(=O)(=O)CC(=O)N1CC2(C1)OCc1nc(C3=NOC(c4cc(Cl)c(Cl)c(Cl)c4)(C(F)(F)F)C3)ccc12]

This compound was prepared similarly to Example 7 except that 1,2,3-trichloro-5-(1-trifluoromethyl-vinyl)-benzene was used in place of 1,3-dichloro-2-fluoro-5-(1-trifluoromethyl-vinyl)-benzene to afford title compound as pale yellow solid (52 mg, 15%). $^1$H NMR (400 MHz, CDCl3) δ: 3.18 (s, 3H), 3.81-3.85 (m, 3H), 4.22 (d, J=18.16 Hz, 1H), 4.34 (dd, $J_1$=2.68 Hz, $J_2$=11.08 Hz, 1H), 4.45 (dd, $J_1$=2.44 Hz, $J_2$=11.16 Hz, 1H), 4.68 (s, 2H), 5.05-5.14 (m, 2H), 7.62 (s, 2H), 7.91 (d, J=8.08 Hz, 1H), 8.05 (d, J=8.08 Hz, 1H). LC-MS (m/z): 597.8 (M+H).

Example 10

1-(2'-(5-(3,5-dichloro-4-fluorophenyl)-5-(trifluoromethyl)-4,5-dihydroisoxazol-3-yl)-7'H-spiro[azetidine-3,5'-furo[3,4-b]pyridine]-1-yl)-2-methylpropan-1-one

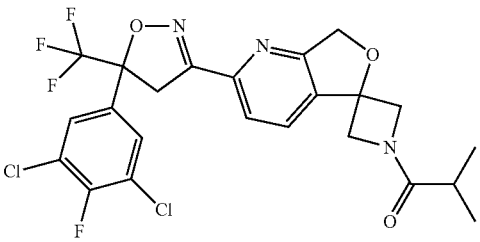 [SMILES: CC(C)C(=O)N1CC2(C1)OCc1nc(C3=NOC(c4cc(Cl)c(F)c(Cl)c4)(C(F)(F)F)C3)ccc12]

This compound was prepared similarly to Example 7 except that isobutyric acid was used in place of methane sulfonyl acetic acid. Yield 115 mg (35%). $^1$H NMR (400 MHz, CDCl3) δ: 1.14 (d, J=6.76 Hz, 6H), 2.46-2.52 (m, 1H), 3.84 (d, J=18.28 Hz, 1H), 4.20-4.22 (m, 2H), 4.33 (d, J=9.16 Hz, 1H), 4.38 (d, J=10.96 Hz, 1H), 4.53 (d, J=9.28 Hz, 1H), 5.07-5.09 (m, 2H), 7.57 (d, J=5.96 Hz, 2H), 7.79 (d, J=8.12 Hz, 1H), 8.04 (d, J=8.12 Hz, 1H). LC-MS (m/z): 530.1 (M−H).

Example 11

1-(2'-(5-(3,5-dichlorophenyl)-5-(trifluoromethyl)-4,5-dihydroisoxazol-3-yl)-7'H-spiro[azetidine-3,5'-furo[3,4-b]pyridine]-1-yl)-2-methylpropan-1-one

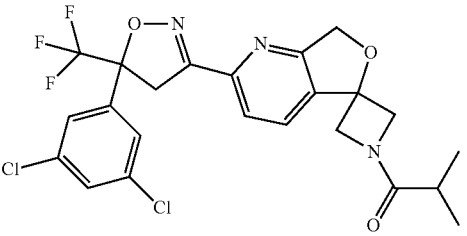 [SMILES: CC(C)C(=O)N1CC2(C1)OCc1nc(C3=NOC(c4cc(Cl)cc(Cl)c4)(C(F)(F)F)C3)ccc12]

This compound was prepared similarly to that of Example 8 except that isobutyric acid was used in place of methane sulfonyl acetic acid. Yield 98 mg (30%). $^1$H NMR (400 MHz, CDCl3) δ: 1.18 (d, J=6.8 Hz, 6H), 2.49-2.55 (m, 1H), 3.87 (d, J=18.44 Hz, 1H), 4.23-4.28 (m, 2H), 4.34-4.42 (m, 2H), 4.56

(d, J=7.28 Hz, 1H), 5.12 (s, 2H), 7.44 (t, J=1.84 Hz, 1H), 7.53 (s, 2H), 7.81 (d, J=8.08 Hz, 1H), 8.07 (d, J=8.08 Hz, 1H). LC-MS (m/z): 513.9 (M+H).

Example 12

2-methyl-1-(2'-(5-(3,4,5-trichlorophenyl)-5-(trifluoromethyl)-4,5-dihydroisoxazol-3-yl)-7'H-spiro[azetidine-3,5'-furo[3,4-b]pyridine]-1-yl)propan-1-one

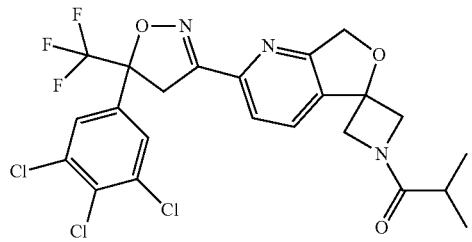 [SMILES: CC(C)C(=O)N1CC2(C1)OCc1nc(C3=NOC(c4cc(Cl)c(Cl)c(Cl)c4)(C(F)(F)F)C3)ccc12]

This compound was prepared similarly to Example 9 except that isobutyric acid was used in place of methane sulfonyl acetic acid. Yield 165 mg (51%). $^1$H NMR (400 MHz, CDCl3) δ: 1.15 (d, J=6.8 Hz, 6H), 2.46-2.53 (m, 1H), 3.84 (d, J=18.08 Hz, 1H), 4.20-4.25 (m, 2H), 4.31-4.36 (m, 2H), 4.53 (d, J=8.44 Hz, 1H), 5.05-5.13 (m, 2H), 7.63 (s, 2H), 7.79 (d, J=8.08 Hz, 1H), 8.04 (d, J=8.08 Hz, 1H). LC-MS (m/z): 547.8 (M+H).

Intermediate 3. tert-butyl 6'-chloro-1H,1'H-spiro[azetidine-3,3'-furo[3,4-c]pyridine]-1-carboxylate

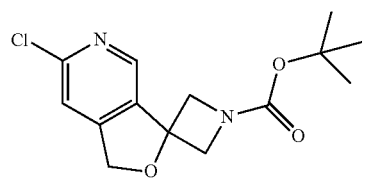 [SMILES: CC(C)(C)OC(=O)N1CC2(C1)OCc1cc(Cl)ncc12]

Step 1. 5-iodo-4-methyl-pyridin-2-ylamine

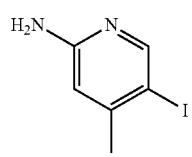

To a stirred solution of 4-methyl-pyridin-2-ylamine (30 g, 278 mmol, 1 eq) in acetic acid (167 mL) was added periodic acid (12.7 g, 55.6 mmol, 0.2 eq) followed by addition of sulphuric acid (4.8 mL, 90.8 mmol, 0.34 eq), water (33.3 mL) and iodine (28.7 g, 111.1 mmol, 0.4 eq) at room temperature. Resulting reaction mixture was heated at 80° C. for 6 hours. After complete consumption of starting material, reaction mixture was cooled and poured into sodium thiosulfate solution (200 mL), reddish oil was settled down at the bottom. Reaction mixture was decanted from reddish oil and filtrate was basified with 50% sodium hydroxide solution (100 mL), yellow colored solid was formed. Resulting solid was extracted with diethyl ether (2×200 mL) and dried over sodium sulfate. Organic layer was concentrated under reduced pressure to afford brown semi solid (60 g, crude). Crude was purified by column chromatography using silica gel (100-200 mesh). Desired compound was eluted at 15% EtOAc in hexane to get title compound as faint brown solid (50.7 g, 78%). $^1$H NMR (400 MHz, CDCl3) δ: 2.27 (s, 3H), 4.46 (bs, 2H), 6.44 (s, 1H), 8.24 (s, 1H).

Step 2. 2-chloro-5-iodo-4-methyl-pyridine

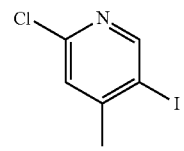

To a stirred solution of concentrated hydrochloride acid (233 mL) at 0° C. was added 5-iodo-4-methyl-pyridin-2-ylamine (25 g, 107 mmol, 1 eq) followed by addition of pre-dissolved sodium nitrite (29.5 g, 427 mmol, 4 eq) in water (100 mL) in drop wise manner over period of 30 minutes. Resulting reaction mixture was stirred at room temperature for 16 hours. After complete consumption of starting material, reaction mixture was cooled to 0° C. and pH was adjusted to 12 by saturated aqueous sodium hydroxide solution, extracted with DCM (3×200 mL). Combined organic layer was dried over anhydrous Na$_2$SO$_4$ and concentrated under reduced pressure to get brown oil (23 g, crude). Crude was purified by column chromatography using silica gel (100-200 mesh). Desired compound was eluted at 4% ethyl acetate in hexane to get title compound as brown oil (8 g, 30%). $^1$H NMR (400 MHz, CDCl3) δ: 2.38 (s, 3H), 7.21 (s, 1H), 8.59 (s, 1H). LC-MS (m/z): 253.7 (M+H).

Step 3. bromomethyl-2-chloro-5-iodo-pyridine

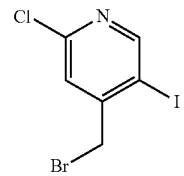

To a stirred solution of 2-chloro-5-iodo-4-methyl-pyridine (23.0 g, 90.909 mmol, 1 eq) in 1,2-dichloroethane (230 mL) was added NBS (24.3 g, 136 mmol, 1.5 eq) followed by addition of AIBN (6.0 g, 36.4 mmol, 0.4 eq) at room temperature in dark. Resulting reaction mixture was heated at 80° C. for 16 hours. After maximum consumption of starting material, reaction mixture was cooled to room temperature and quenched with water (50 mL), extracted with DCM (3×50 mL). Combined organic phase was washed with brine (50 mL), dried over anhydrous Na$_2$SO$_4$ and concentrated under reduced pressure to get dark brown semi solid (20 g, crude). Crude of title compound was used as such for next reaction. LC-MS (m/z): No ionisation.

Step 4. (2-chloro-5-iodo-pyridin-4-yl)-methanol

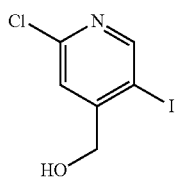

To a stirred solution of crude 4-bromomethyl-2-chloro-5-iodo-pyridine (23 g, 69.3 mmol, 1 eq) in 1,4-dioxane (230 mL) was added suspension of CaCO₃ (36.05 g, 360 mmol, 5.2 eq) in water (230 mL) at room temperature. Resulting reaction mixture was refluxed for 10 hours. After complete consumption of starting material, reaction mixture was cooled to room temperature and filtered through celite bed over Buchner funnel. Celite bed was washed with EtOAc (2×100 mL). Combined filtrate was washed with water (100 mL) and aqueous sodium bicarbonate (50 mL), dried over sodium sulfate and concentrated under reduced pressure to afford brown solid (22 g, crude). Crude was purified by column chromatography using silica gel (100-200 mesh). Desired compound was eluted at 30% EtOAc in hexane to get title compound as faint yellow solid (1.4 g, impure) and also 11.5 g of 2-chloro-5-iodo-4-methyl-pyridine was recovered. Impure was used as such for next reaction. ¹H NMR (400 MHz, CDCl3) δ: 2.1 (t, J=5.64 Hz, 1H), 4.62 (d, J=6.24 Hz, 2H), 7.54 (s, 1H), 8.58 (s, 1H). LC-MS (m/z): 267.7 (M−H).

Step 5. 3-(6-chloro-4-hydroxymethyl-pyridin-3-yl)-3-hydroxy-azetidine-1-carboxylic acid tert-butyl ester

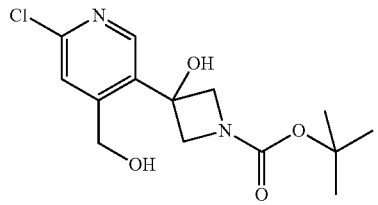 [SMILES: CC(C)(C)OC(=O)N1CC(O)(c2cnc(Cl)cc2CO)C1]

To a stirred solution of (2-chloro-5-iodo-pyridin-4-yl)-methanol (2 g, 7.44 mmol, 1 eq) in dry THF (20 mL) was added i-PrMgCl.LiCl complex (1.3M in THF, 13.7 mL, 17.8 mmol, 2.4 eq) at −20° C. in drop wise manner over period of 10 minutes. Pre-dissolved solution of N-boc-3-azetidinone (1.53 g, 8.9 mmol, 1.2 eq) in dry THF (10 mL) was added at −20° C. to above reaction mixture. Resulting reaction mixture was stirred at room temperature for 16 hours under nitrogen atmosphere. After maximum consumption of starting material, reaction mixture was cooled to 0° C., quenched with 10% citric acid solution (20 mL) and extracted with ethyl acetate (3×50 mL). Combined organic phase was dried over anhydrous Na₂SO₄ and concentrated under reduced pressure to get brown oil (2.2 g, crude). Crude compound was purified by column chromatography by using silica gel (100-200 mesh). Desired compound was eluted at 20% ethyl acetate in hexane to afford title compound as yellow solid (0.45 g, 19%). ¹H NMR (400 MHz, CDCl3) δ: 1.38 (s, 9H), 3.96 (d, J=8.8 Hz, 2H), 4.38 (d, J=9.32 Hz, 2H), 4.53 (d, J=5.64 Hz, 2H), 5.53 (t, J=5.32 Hz, 1H), 6.40 (s, 1H), 7.57 (s, 1H), 8.33 (s, 1H). LC-MS (m/z): 314.9 (M+H).

Step 6. tert-butyl 6'-chloro-1H,1'H-spiro[azetidine-3,3'-furo[3,4-c]pyridine]-1-carboxylate (Intermediate 3)

To a stirred solution of 3-(6-chloro-4-hydroxymethyl-pyridin-3-yl)-3-hydroxy-azetidine-1-carboxylic acid tert-butyl ester (0.45 g, 1.43 mmol, 1 eq) in dry toluene (4.5 mL) was added triethyl amine (0.40 mL, 2.87 mmol, 2 eq) at 0° C. followed by addition of tosyl anhydride (0.42 g, 1.29 mmol, 0.9 eq). Resulting reaction mixture was stirred at room temperature for 16 hours under nitrogen atmosphere. After complete consumption of starting material, reaction mixture was quenched with saturated NaHCO₃ solution (10 mL), diluted with water (20 mL) and extracted with ethyl acetate (2×50 mL). Combined organic phase was dried over anhydrous Na₂SO₄ and concentrated under reduced pressure to get brown sticky mass (0.4 g, crude). Crude compound was purified by preparative TLC in 40% ethyl acetate in hexane to afford title compound as off white solid (0.18 g, 42%). ¹H NMR (400 MHz, CDCl3) δ: 1.47 (s, 9H), 4.13 (d, J=10.16 Hz, 2H), 4.33 (d, J=10.08 Hz, 2H), 5.07 (s, 2H), 7.20 (s, 1H), 8.50 (s, 1H). LC-MS (m/z): 297.1 (M+H).

Example 13

1-(6'-(5-(3,5-dichloro-4-fluorophenyl)-5-(trifluoromethyl)-4,5-di hydroisoxazol-3-yl)-1'H-spiro[azetidine-3,3'-furo[3,4-c]pyridine]-1-yl)-2-(methylsulfonyl)ethanone

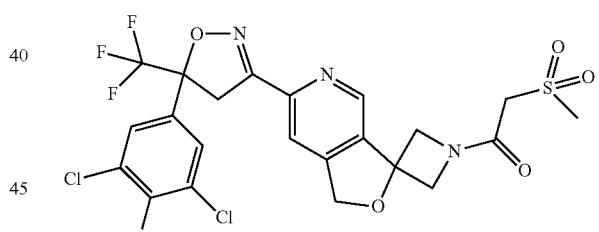

Step 1. 1-tert-butyl 6'-ethyl-1'H-spiro[azetidine-3,3'-furo[3,4-c]pyridine]-1,6'-dicarboxylate

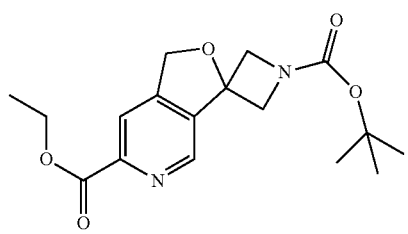 [SMILES: CCOC(=O)c1cc2c(cn1)C1(CN(C(=O)OC(C)(C)C)C1)OC2]

To a stirred solution of tert-butyl 6'-chloro-1'H-spiro[azetidine-3,3'-furo[3,4-c]pyridine]-1-carboxylate (0.7 g, 2.36 mmol, 1 eq) in ethanol (15 mL) was added NaOAc (0.39 g, 4.73 mmol, 2 eq) and reaction mixture was degassed by nitrogen for 30 minutes in 100 mL autoclave vessel. After degassing, palladium acetate (5 mg, 0.024 mmol, 0.01 eq), dppf (39 mg, 0.071 mmol, 0.03 eq) was added. Resulting reaction mixture was heated at 80° C. under 225 psi of CO gas for 12 hours. After complete consumption of starting material, reaction mixture was filtered through celite bed; celite bed was washed with ethanol (3×10 mL). Combined filtrate was concentrated under reduced pressure to afford brown oil (0.750 g, crude). Crude compound was purified by column chromatography in 100-200 mesh silica gel, title compound was eluted in 40% ethyl acetate in hexanes to afford title compound as yellow semisolid (0.4 g, 51%). $^1$H NMR (400 MHz, CDCl3) δ: 1.44 (t, J=7.18 Hz, 3H), 1.47 (s, 9H), 4.17 (d, J=9.92 Hz, 2H), 4.36 (d, J=9.92 Hz, 2H), 4.49 (q, J=7.16 Hz, 2H), 5.15 (s, 2H), 8.03 (s, 1H), 8.84 (s, 1H). LC-MS (m/z): 334.9 (M+H).

Step 2. tert-butyl 6'-formyl-1'H-spiro[azetidine-3,3'-furo[3,4-c]pyridine]-1-carboxylate

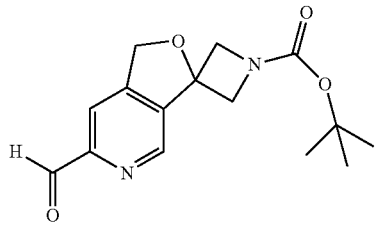 [SMILES: CC(C)(C)OC(=O)N1CC2(C1)OCc1cc(C=O)ncc12]

To the stirred solution of 1-tert-butyl 6'-ethyl 1'H-spiro[azetidine-3,3'-furo[3,4-c]pyridine]-1,6'-dicarboxylate (0.2 g, 0.60 mmol, 1 eq) in DCM (10 mL) at −78° C. under nitrogen atmosphere was added 25% DIBAL in toluene (0.255 g, 2.56 mL, 1.80 mmol, 3 eq). Resulting reaction mixture was stirred at −78° C. for 1 hour under nitrogen atmosphere. After complete consumption of starting material, reaction mixture was quenched by methanol (0.2 mL) followed by addition of saturated solution of sodium potassium tartarate salt (0.5 mL) at −78° C. and extracted with DCM (3×25 mL). Combined organic layer was dried over sodium sulphate, concentrated under reduced pressure to afford the title compound as brown solid (0.15 g, crude). Crude compound was used as such for the next reaction. $^1$H NMR (400 MHz, CDCl3) δ: 1.47 (s, 9H), 4.19 (d, J=10 Hz, 2H), 4.37 (d, J=10.04 Hz, 2H), 5.16 (s, 2H), 7.85 (s, 1H), 8.89 (s, 1H), 10.12 (s, 1H). LC-MS (m/z): 291.0 (M+H).

Step 3. tert-butyl 6'-((hydroxyimino)methyl)-1'H-spiro[azetidine-3,3'-furo[3,4-c]pyridine]-1-carboxylate

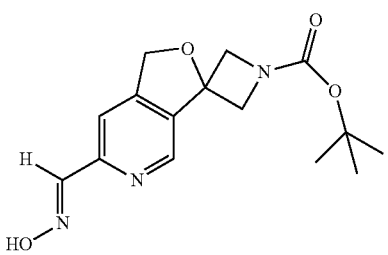 [SMILES: CC(C)(C)OC(=O)N1CC2(C1)OCc1cc(/C=N/O)ncc12]

To a stirred solution of tert-butyl 6'-formyl-1'H-spiro[azetidine-3,3'-furo[3,4-c]pyridine]-1-carboxylate (0.15 g, 0.52 mmol, 1 eq.) in mixture of methanol (4.0 mL):water (4.0 mL) was added NaOAc (85 mg, 1.03 mmol, 2 eq.) followed by addition of NH$_2$OH.HCl (72 mg, 1.03 mmol, 2 eq) at room temperature. Resulting reaction mixture was stirred at room temperature for 18 hours under nitrogen atmosphere. After complete consumption starting material, reaction mixture was concentrated under reduced pressure; resulting residue was diluted with water (5.0 mL) and extracted by ethyl acetate (3×20 mL). Combined organic layer was dried over sodium sulphate and concentrated under reduced pressure to afford title compound as brown solid (0.15 g, 95%). $^1$H NMR (400 MHz, CDCl3) δ: 1.47 (s, 9H), 4.16 (d, J=9.64 Hz, 2H), 4.34 (d, J=9.6 Hz, 2H), 5.10 (s, 2H), 7.67 (s, 1H), 8.27 (s, 1H), 8.72 (s, 1H). LC-MS (m/z): 306.2 (M+H).

Step 4. tert-butyl 6'-(5-(3,5-dichloro-4-fluorophenyl)-5-(trifluoromethyl)-4,5-dihydroisoxazol-3-yl)-1'H-spiro[azetidine-3,3'-furo[3,4-c]pyridine]-1-carboxylate

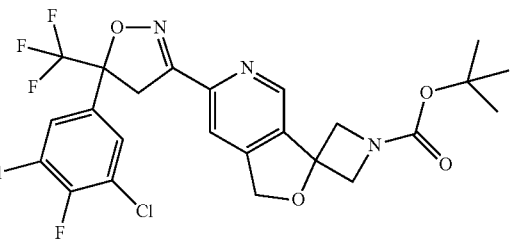

To a stirred solution of tert-butyl 6'-((hydroxyimino)methyl)-1'H-spiro[azetidine-3,3'-furo[3,4-c]pyridine]-1-carboxylate (0.15 g, 0.49 mmol, 1 eq) in DMF (5.0 mL) was added NCS (84 mg, 0.63 mmol, 1.2 eq) at room temperature in dark under nitrogen atmosphere. Resulting reaction mixture was stirred at 45° C. for 1 hour. After chloro intermediate formation, 1,3-dichloro-2-fluoro-5-(1-trifluoromethyl-vinyl)-benzene (0.163 g, 0.63 mmol, 1.2 eq.) was added followed by addition of KHCO$_3$ (79 mg, 0.79 mmol, 1.5 eq). Resulting reaction mixture was stirred at room temperature for 16 hours in dark under nitrogen atmosphere. After complete consumption of chloro intermediate, reaction mixture was quenched with water (20 mL) and extracted with ethyl acetate (3×20 mL). Combined organic layer was dried over anhydrous Na$_2$SO$_4$ and concentrated under reduced pressure to get brown thick oil (0.2 g, crude). Crude compound was purified by column chromatography in 100-200 mesh size silica gel. Desired compound was eluted in 25% ethyl acetate in hexane to afford title compound as off white solid (0.14 g, 51%). $^1$H NMR (400 MHz, CDCl3) δ: 1.47 (s, 9H), 3.88 (d, J=18.4 Hz, 1H), 4.12-4.16 (m, 2H), 4.25 (d, J=18.16 Hz, 1H), 4.35 (dd, J$_1$=3.3 Hz, J$_2$=9.34 Hz, 2H), 5.12 (s, 2H), 7.57 (d, J=6 Hz, 2H), 7.90 (s, 1H), 8.70 (s, 1H). LC-MS (m/z): 562.1 (M+H).

Step 5. trifluoro acetic acid salt of 6'-(5-(3,5-dichloro-4-fluorophenyl)-5-(trifluoromethyl)-4,5-dihydroisoxazol-3-yl)-1'H-spiro[azetidine-3,3'-furo[3,4-c]pyridine]

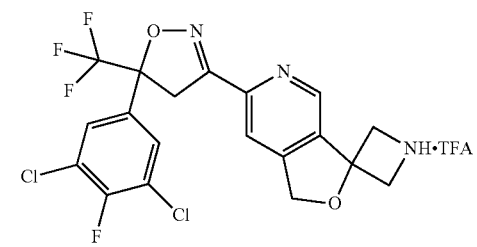

To a stirred solution of tert-butyl 6'-(5-(3,5-dichloro-4-fluorophenyl)-5-(trifluoromethyl)-4,5-dihydroisoxazol-3-yl)-1H-spiro[azetidine-3,3'-furo[3,4-c]pyridine]-1-carboxylate (0.14 g, 0.25 mmol, 1 eq) in DCM (3 mL) was added TFA (0.382 mL, 4.99 mmol, 20 eq.) at 0° C. under nitrogen atmosphere. Resulting reaction mixture was stirred at room temperature for 16 hours. After complete consumption of starting material, reaction mixture was concentrated under reduced pressure to afford brownish semisolid, which was stripped out by chloroform (3×15 mL) to afford title compound as brown solid (0.11 g, crude). Crude TFA salt was used as such for next reaction. LC-MS (m/z): 462.1 (M+H).

Step 6. 1-(6'-(5-(3,5-dichloro-4-fluorophenyl)-5-(trifluoromethyl)-4,5-dihydroisoxazol-3-yl)-1'H-spiro[azetidine-3,3'-furo[3,4-c]pyridine]-1-yl)-2-(methylsulfonyl)ethanone Example 13

To the stirred solution of trifluoro acetic acid salt of 6'-(5-(3,5-dichloro-4-fluorophenyl)-5-(trifluoromethyl)-4,5-dihydroisoxazol-3-yl)-1'H-spiro[azetidine-3,3'-furo[3,4-c]pyridine] (0.110 g, 0.239 mmol, 1 eq) in DMF (2.0 mL) was added TEA (0.166 mL, 1.193 mmol, 5 eq) followed by addition of EDC.HCl (68 mg, 0.358 mmol, 1.5 eq), HOBt (32 mg, 0.239 mmol, 1 eq.) and stirred at room temperature under nitrogen atmosphere for 15 minutes. Methane sulfonyl-acetic acid (69 mg, 0.477 mmol, 2 eq) was added and resulting reaction mixture was stirred at room temperature for 18 hours. After complete consumption of starting material, reaction mixture was quenched by water (20 mL), extracted with ethyl acetate (3×30 mL). Combined organic layer was washed by saturated LiCl solution (2×25 mL), dried over sodium sulphate and concentrated under reduced pressure to afford brown oil (0.15 g, crude). Crude was purified by column chromatography in 100-200 mesh silica gel. Desired compound was eluted in 50% ethyl acetate in hexanes to afford light brown solid (0.07 g), which was recrystallised by chloroform (0.5 mL) in hexanes (3.0 mL) to afford title compound as off white solid (32 mg, 23%). $^1$H NMR (400 MHz, CDCl3) δ: 3.18 (s, 3H), 3.85-3.89 (m, 3H), 4.25 (d, $J_1$=1.78 Hz, $J_2$=18.26 Hz, 1H), 4.36-4.40 (m, 1H), 4.48 (d, $J_1$=2.48 Hz, $J_2$=11.24 Hz, 1H), 4.70 (d, J=4.4 Hz, 2H), 5.16 (s, 2H), 7.57 (d, J=6 Hz, 2H), 7.92 (s, 1H), 8.78 (s, 1H). LC-MS (m/z): 579.9 (M−H).

Example 14

2-(methylsulfonyl)-1-(6'-(5-(3,4,5-trichlorophenyl)-5-(trifluoromethyl)-4,5-dihydroisoxazol-3-yl)-1'H-spiro[azetidine-3,3'-furo[3,4-c]pyridine]-1-yl)ethanone

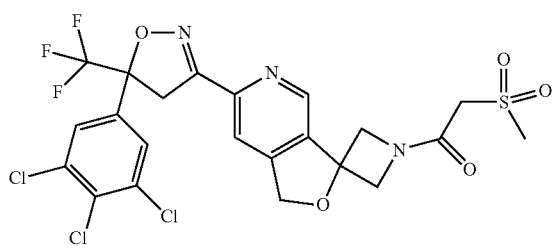 [SMILES: CS(=O)(=O)CC(=O)N1CC2(C1)OCc1cc(C3=NOC(c4cc(Cl)c(Cl)c(Cl)c4)(C(F)(F)F)C3)ncc12]

This compound was prepared similarly to Example 13 except that 1,2,3-trichloro-5-(1-trifluoromethyl-vinyl) was used in place of 1,3-dichloro-2-fluoro-5-(1-trifluoromethyl-vinyl)-benzene to afford title compound as off-white solid (17 mg, 9%). $^1$H NMR (400 MHz, CDCl3) δ: 3.18 (s, 3H), 3.85-3.90 (m, 3H), 4.25 (dd, $J_1$=1.74 Hz, $J_2$=18.26 Hz, 1H), 4.36-4.40 (m, 1H), 4.46-4.49 (m, 1H), 4.71 (d, J=4.28 Hz, 2H), 5.16 (s, 2H), 7.63 (s, 2H), 7.92 (s, 1H), 8.78 (s, 1H). LC-MS (m/z): 596.0 (M−H).

Example 15

1-(6'-(5-(3,5-dichlorophenyl)-5-(trifluoromethyl)-4,5-dihydroisoxazol-3-yl)-1'H-spiro[azetidine-3,3'-furo[3,4-c]pyridine]-1-yl)-2-(methylsulfonyl)ethanone

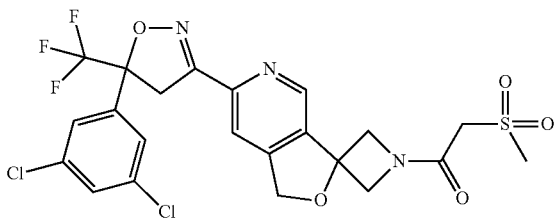 [SMILES: CS(=O)(=O)CC(=O)N1CC2(C1)OCc1cc(C3=NOC(c4cc(Cl)cc(Cl)c4)(C(F)(F)F)C3)ncc12]

This compound was prepared similarly to Example 13 except that 1,3-dichloro-5-(1-trifluoromethyl-vinyl)-benzene was used in place of 1,3-dichloro-2-fluoro-5-(1-trifluoromethyl-vinyl)-benzene to afford title compound as white solid (0.100 g, 52%). $^1$H NMR (400 MHz, CDCl3) δ: 3.18 (s, 3H), 3.86-3.90 (m, 3H), 4.24 (dd, $J_1$=1.96 Hz, $J_2$=18.24 Hz, 1H), 4.36-4.40 (m, 1H), 4.48 (dd, $J_1$=2.72 Hz, $J_2$=11.28 Hz, 1H), 4.71 (d, J=4.56 Hz, 2H), 5.16 (s, 2H), 7.41 (d, J=1.84 Hz, 1H), 7.49 (s, 2H), 7.93 (s, 1H), 8.78 (s, 1H). LC-MS (m/z): 562.1 (M−H).

Example 16

1-(6'-(5-(3,5-dichloro-4-fluorophenyl)-5-(trifluoromethyl)-4,5-dihydroisoxazol-3-yl)-1'H-spiro[azetidine-3,3'-furo[3,4-c]pyridine]-1-yl)-2-methylpropan-1-one

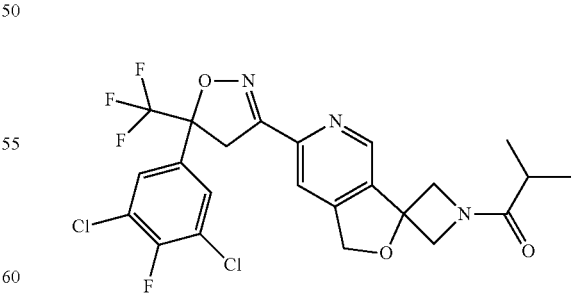

This compound was prepared similarly to Example 13 except that isobutyric acid was used in place of methane sulfonyl acetic acid. Yield 0.035 g (25%). $^1$H NMR (400 MHz, CDCl3) δ: 1.16 (s, 6H), 2.47-2.54 (m, 1H), 3.87 (d, J=18.2 Hz, 1H), 4.25 (d, J=18.2 Hz, 1H), 4.28-4.41 (m, 3H), 4.55 (d, J=6.96 Hz, 1H), 5.15 (s, 2H), 7.57 (d, J=6 Hz, 2H), 7.93 (s, 1H), 8.65 (s, 1H). LC-MS (m/z): 531.7 (M+H).

Example 17

2-methyl-1-(6'-(5-(3,4,5-trichlorophenyl)-5-(trifluoromethyl)-4,5-dihydroisoxazol-3-yl)-1'H-spiro[azetidine-3,3'-furo[3,4-c]pyridine]-1-yl)propan-1-one

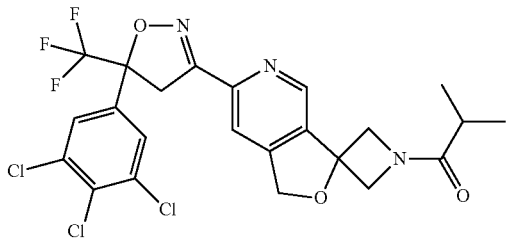 [SMILES: CC(C)C(=O)N1CC2(C1)OCc1cc(C3=NOC(c4cc(Cl)c(Cl)c(Cl)c4)(C(F)(F)F)C3)ncc12]

This compound was prepared similarly to Example 14 except that isobutyric acid was used in place of methane sulfonyl acetic acid. Yield 15 mg (9%). $^1$H NMR (400 MHz, CDCl3) δ: 1.16 (s, 6H), 2.49-2.52 (m, 1H), 3.87 (d, J=18.12 Hz, 1H), 4.25 (d, J=18.2 Hz, 1H), 4.36-4.41 (m, 3H), 4.49-4.51 (m, 1H), 5.15 (s, 2H), 7.63 (s, 2H), 7.92 (s, 1H), 8.65 (s, 1H). LC-MS (m/z): 546.0 (M−H).

Example 18

1-(6'-(5-(3,5-dichlorophenyl)-5-(trifluoromethyl)-4,5-dihydroisoxazol-3-yl)-1'H-spiro[azetidine-3,3'-furo[3,4-c]pyridine]-1-yl)-2-methylpropan-1-one

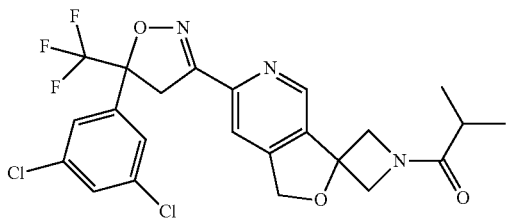 [SMILES: CC(C)C(=O)N1CC2(C1)OCc1cc(C3=NOC(c4cc(Cl)cc(Cl)c4)(C(F)(F)F)C3)ncc12]

This compound was prepared similarly to Example 15 except that isobutyric acid was used in place of methane sulfonyl acetic acid. Yield 0.030 g (17%). $^1$H NMR (400 MHz, CDCl3) δ: 1.15 (d, J=6.64 Hz, 6H), 2.48-2.54 (m, 1H), 3.87 (d, J=17.6 Hz, 1H), 4.25 (d, J=18.2 Hz, 1H,) 4.28-4.30 (m, 1H) 4.34-4.42 (m, 2H), 4.54-4.56 (m, 1H), 5.15 (s, 2H), 7.41 (t, J=1.8 Hz, 1H), 7.50 (s, 2H), 7.93 (s, 1H), 8.65 (s, 1H). LC-MS (m/z): 514 (M+H).

The following spirocyclic isoxazolines of Table 1 can also be prepared from Formula (1.1b).

(1.1b)

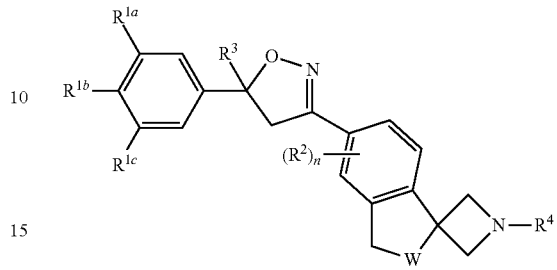

For Table 1: n is the integer 0; W is S(O)$_2$; R$^3$ is CF$_3$; and R$^4$ is C(O)R$^5$

TABLE 1

Spirocyclic Isoxazolines of Formula (1.1b)

| Example No. | R$^{1a}$ | R$^{1b}$ | R$^{1c}$ | R$^5$ |
|---|---|---|---|---|
| 19 | Cl | Cl | Cl | Methyl |
| 20 | Cl | H | Cl | Methyl |
| 21 | Cl | F | Cl | Methyl |
| 22 | Cl | Cl | Cl | Ethyl |
| 23 | Cl | H | Cl | Ethyl |
| 24 | Cl | F | Cl | Ethyl |
| 25 | Cl | Cl | Cl | Propyl |
| 26 | Cl | H | Cl | Propyl |
| 27 | Cl | F | Cl | Propyl |
| 28 | Cl | Cl | Cl | Isopropyl |
| 29 | Cl | H | Cl | Isopropyl |
| 30 | Cl | F | Cl | Isopropyl |
| 31 | Cl | Cl | Cl | Isobutyl |
| 32 | Cl | H | Cl | Isobutyl |
| 33 | Cl | F | Cl | Isobutyl |
| 34 | Cl | Cl | Cl | CH$_2$OH |
| 35 | Cl | H | Cl | CH$_2$OH |
| 36 | Cl | F | Cl | CH$_2$OH |
| 37 | Cl | Cl | Cl | Cyclopropyl |
| 38 | Cl | H | Cl | Cyclopropyl |
| 39 | Cl | F | Cl | Cyclopropyl |
| 40 | Cl | Cl | Cl | Cyclobutyl |
| 41 | Cl | H | Cl | Cyclobutyl |
| 42 | Cl | F | Cl | Cyclobutyl |
| 43 | Cl | Cl | Cl | CH$_2$-cyclopropyl |
| 44 | Cl | H | Cl | CH$_2$-cyclopropyl |
| 45 | Cl | F | Cl | CH$_2$-cyclopropyl |
| 46 | Cl | Cl | Cl | CH$_2$-cyclobutyl |
| 47 | Cl | H | Cl | CH$_2$-cyclobutyl |
| 48 | Cl | F | Cl | CH$_2$-cyclobutyl |
| 49 | Cl | Cl | Cl | CH$_2$CF$_3$ |
| 50 | Cl | H | Cl | CH$_2$CF$_3$ |
| 51 | Cl | F | Cl | CH$_2$CF$_3$ |
| 52 | Cl | Cl | Cl | —CH$_2$SCH$_3$ |
| 53 | Cl | H | Cl | —CH$_2$SCH$_3$ |
| 54 | Cl | F | Cl | —CH$_2$SCH$_3$ |
| 55 | Cl | Cl | Cl | —CH$_2$S(O)CH$_3$ |
| 56 | Cl | H | Cl | —CH$_2$S(O)CH$_3$ |
| 57 | Cl | F | Cl | —CH$_2$S(O)CH$_3$ |
| 58 | Cl | Cl | Cl | —CH$_2$S(O)$_2$CH$_3$ |
| 59 | Cl | H | Cl | —CH$_2$S(O)$_2$CH$_3$ |
| 60 | Cl | F | Cl | —CH$_2$S(O)$_2$CH$_3$ |
| 61 | Cl | Cl | Cl | 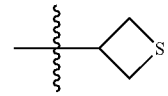 |

TABLE 1-continued

Spirocyclic Isoxazolines of Formula (1.1b)

| Example No. | $R^{1a}$ | $R^{1b}$ | $R^{1c}$ | $R^5$ |
|---|---|---|---|---|
| 62 | Cl | H | Cl | thietane |
| 63 | Cl | F | Cl | thietane |
| 64 | Cl | Cl | Cl | thietane S-oxide |
| 65 | Cl | H | Cl | thietane S-oxide |
| 66 | Cl | F | Cl | thietane S-oxide |
| 67 | Cl | Cl | Cl | thietane S,S-dioxide |
| 68 | Cl | H | Cl | thietane S,S-dioxide |
| 69 | Cl | F | Cl | thietane S,S-dioxide |
| 70 | Cl | Cl | Cl | cyclopropyl-OH |
| 71 | Cl | H | Cl | cyclopropyl-OH |
| 72 | Cl | F | Cl | cyclopropyl-OH |
| 73 | Cl | Cl | Cl | CH2-pyrazol-1-yl |
| 74 | Cl | H | Cl | CH2-pyrazol-1-yl |
| 75 | Cl | F | Cl | CH2-pyrazol-1-yl |
| 76 | Cl | Cl | Cl | 1-($CF_3$)cyclopropyl |
| 77 | Cl | H | Cl | 1-($CF_3$)cyclopropyl |
| 78 | Cl | F | Cl | 1-($CF_3$)cyclopropyl |
| 79 | Cl | Cl | Cl | CH2-(3-methylpyrazol-1-yl) |
| 80 | Cl | H | Cl | CH2-(3-methylpyrazol-1-yl) |
| 81 | Cl | F | Cl | CH2-(3-methylpyrazol-1-yl) |
| 82 | Cl | Cl | Cl | 2,2-difluorocyclopropyl |
| 83 | Cl | H | Cl | 2,2-difluorocyclopropyl |
| 84 | Cl | F | Cl | 2,2-difluorocyclopropyl |
| 85 | Cl | Cl | Cl | CH2-pyridin-2-yl |
| 86 | Cl | H | Cl | CH2-pyridin-2-yl |

TABLE 1-continued

Spirocyclic Isoxazolines of Formula (1.1b)

| Example No. | $R^{1a}$ | $R^{1b}$ | $R^{1c}$ | $R^5$ |
|---|---|---|---|---|
| 87 | Cl | F | Cl | 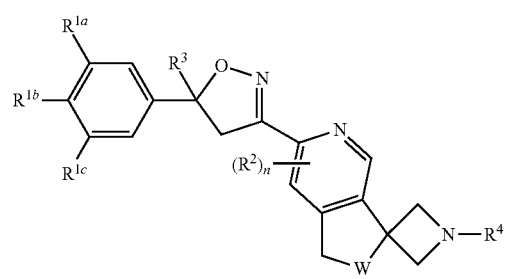 |

By the methods described herein, the following spirocyclic isoxazolines of Table 3 can be prepared from Formula (1.2b).

(1.2b)

For Table 2: n is the integer 0; W is O; $R^3$ is $CF_3$; and $R^4$ is $C(O)R^5$

TABLE 2

Spirocyclic Isoxazolines of Formula (1.2b)

| Example No. | $R^{1a}$ | $R^{1b}$ | $R^{1c}$ | $R^5$ |
|---|---|---|---|---|
| 88 | Cl | Cl | Cl | Methyl |
| 89 | Cl | H | Cl | Methyl |
| 90 | Cl | F | Cl | Methyl |
| 91 | Cl | Cl | Cl | Ethyl |
| 92 | Cl | H | Cl | Ethyl |
| 93 | Cl | F | Cl | Ethyl |
| 94 | Cl | Cl | Cl | Propyl |
| 95 | Cl | H | Cl | Propyl |
| 96 | Cl | F | Cl | Propyl |
| 97 | Cl | Cl | Cl | Isobutyl |
| 98 | Cl | H | Cl | Isobutyl |
| 99 | Cl | F | Cl | Isobutyl |
| 100 | Cl | Cl | Cl | $CH_2OH$ |
| 101 | Cl | H | Cl | $CH_2OH$ |
| 102 | Cl | F | Cl | $CH_2OH$ |
| 103 | Cl | Cl | Cl | Cyclopropyl |
| 104 | Cl | H | Cl | Cyclopropyl |
| 105 | Cl | F | Cl | Cyclopropyl |
| 106 | Cl | Cl | Cl | Cyclobutyl |
| 107 | Cl | H | Cl | Cyclobutyl |
| 108 | Cl | F | Cl | Cyclobutyl |
| 109 | Cl | Cl | Cl | $CH_2$-cyclopropyl |
| 110 | Cl | H | Cl | $CH_2$-cyclopropyl |
| 111 | Cl | F | Cl | $CH_2$-cyclopropyl |
| 112 | Cl | Cl | Cl | $CH_2$-cyclobutyl |
| 113 | Cl | H | Cl | $CH_2$-cyclobutyl |
| 114 | Cl | F | Cl | $CH_2$-cyclobutyl |
| 115 | Cl | Cl | Cl | $CH_2CF_3$ |
| 116 | Cl | H | Cl | $CH_2CF_3$ |
| 117 | Cl | F | Cl | $CH_2CF_3$ |
| 118 | Cl | Cl | Cl | —$CH_2SCH_3$ |
| 119 | Cl | H | Cl | —$CH_2SCH_3$ |
| 120 | Cl | F | Cl | —$CH_2SCH_3$ |
| 121 | Cl | Cl | Cl | —$CH_2S(O)CH_3$ |
| 122 | Cl | H | Cl | —$CH_2S(O)CH_3$ |
| 123 | Cl | F | Cl | —$CH_2S(O)CH_3$ |

TABLE 2-continued

Spirocyclic Isoxazolines of Formula (1.2b)

| Example No. | $R^{1a}$ | $R^{1b}$ | $R^{1c}$ | $R^5$ |
|---|---|---|---|---|
| 124 | Cl | Cl | Cl |  |
| 125 | Cl | H | Cl |  |
| 126 | Cl | F | Cl |  |
| 127 | Cl | Cl | Cl |  |
| 128 | Cl | H | Cl |  |
| 129 | Cl | F | Cl |  |
| 130 | Cl | Cl | Cl |  |
| 131 | Cl | H | Cl |  |
| 132 | Cl | F | Cl |  |
| 133 | Cl | Cl | Cl |  |
| 134 | Cl | H | Cl |  |
| 135 | Cl | F | Cl |  |
| 136 | Cl | Cl | Cl |  |

TABLE 2-continued

Spirocyclic Isoxazolines of Formula (1.2b)

| Example No. | $R^{1a}$ | $R^{1b}$ | $R^{1c}$ | $R^5$ |
|---|---|---|---|---|
| 137 | Cl | H | Cl | pyrazolylmethyl |
| 138 | Cl | F | Cl | pyrazolylmethyl |
| 139 | Cl | Cl | Cl | 1-(trifluoromethyl)cyclopropyl |
| 140 | Cl | H | Cl | 1-(trifluoromethyl)cyclopropyl |
| 141 | Cl | F | Cl | 1-(trifluoromethyl)cyclopropyl |
| 142 | Cl | Cl | Cl | (3-methylpyrazol-1-yl)methyl |
| 143 | Cl | H | Cl | (3-methylpyrazol-1-yl)methyl |
| 144 | Cl | F | Cl | (3-methylpyrazol-1-yl)methyl |
| 145 | Cl | Cl | Cl | 2,2-difluorocyclopropyl |
| 146 | Cl | H | Cl | 2,2-difluorocyclopropyl |
| 147 | Cl | F | Cl | 2,2-difluorocyclopropyl |
| 148 | Cl | Cl | Cl | (pyridin-2-yl)methyl |
| 149 | Cl | H | Cl | (pyridin-2-yl)methyl |
| 150 | Cl | F | Cl | (pyridin-2-yl)methyl |

By the methods described herein, the following pyrrolidinyl spirocyclic isobenzofurans of Table 3 can be prepared from Formula (1.3b).

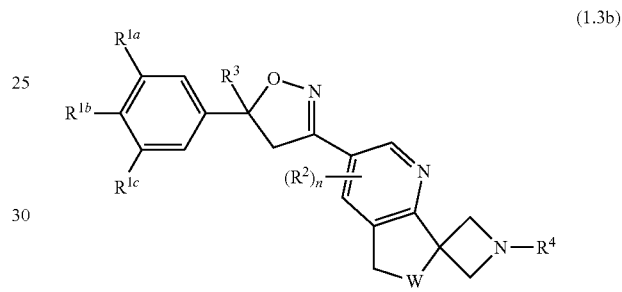

(1.3b)

For Table 3: n is the integer 0; W is O; $R^3$ is $CF_3$; and $R^4$ is $C(O)R^5$

TABLE 3

Spirocyclic Isoxazolines of Formula (1.3b)

| Example No. | $R^{1a}$ | $R^{1b}$ | $R^{1c}$ | $R^5$ |
|---|---|---|---|---|
| 151 | Cl | Cl | Cl | Methyl |
| 152 | Cl | H | Cl | Methyl |
| 153 | Cl | F | Cl | Methyl |
| 154 | Cl | Cl | Cl | Ethyl |
| 155 | Cl | H | Cl | Ethyl |
| 156 | Cl | F | Cl | Ethyl |
| 157 | Cl | Cl | Cl | Propyl |
| 158 | Cl | H | Cl | Propyl |
| 159 | Cl | F | Cl | Propyl |
| 160 | Cl | Cl | Cl | Isobutyl |
| 161 | Cl | H | Cl | Isobutyl |
| 162 | Cl | F | Cl | Isobutyl |
| 163 | Cl | Cl | Cl | $CH_2OH$ |
| 164 | Cl | H | Cl | $CH_2OH$ |
| 165 | Cl | F | Cl | $CH_2OH$ |
| 166 | Cl | Cl | Cl | Cyclopropyl |
| 167 | Cl | H | Cl | Cyclopropyl |
| 168 | Cl | F | Cl | Cyclopropyl |
| 169 | Cl | Cl | Cl | Cyclobutyl |
| 170 | Cl | H | Cl | Cyclobutyl |
| 171 | Cl | F | Cl | Cyclobutyl |
| 172 | Cl | Cl | Cl | $CH_2$-cyclopropyl |
| 173 | Cl | H | Cl | $CH_2$-cyclopropyl |
| 174 | Cl | F | Cl | $CH_2$-cyclopropyl |
| 175 | Cl | Cl | Cl | $CH_2$-cyclobutyl |
| 176 | Cl | H | Cl | $CH_2$-cyclobutyl |
| 177 | Cl | F | Cl | $CH_2$-cyclobutyl |
| 178 | Cl | Cl | Cl | $CH_2CF_3$ |
| 179 | Cl | H | Cl | $CH_2CF_3$ |

TABLE 3-continued

Spirocyclic Isoxazolines of Formula (1.3b)

| Example No. | $R^{1a}$ | $R^{1b}$ | $R^{1c}$ | $R^5$ |
|---|---|---|---|---|
| 180 | Cl | F | Cl | CH$_2$CF$_3$ |
| 181 | Cl | Cl | Cl | —CH$_2$SCH$_3$ |
| 182 | Cl | H | Cl | —CH$_2$SCH$_3$ |
| 183 | Cl | F | Cl | —CH$_2$SCH$_3$ |
| 184 | Cl | Cl | Cl | —CH$_2$S(O)CH$_3$ |
| 185 | Cl | H | Cl | —CH$_2$S(O)CH$_3$ |
| 186 | Cl | F | Cl | —CH$_2$S(O)CH$_3$ |
| 187 | Cl | Cl | Cl | 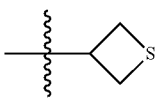 |
| 188 | Cl | H | Cl | 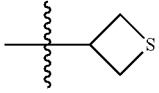 |
| 189 | Cl | F | Cl | 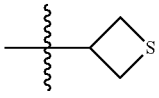 |
| 190 | Cl | Cl | Cl | 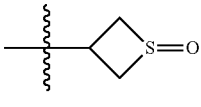 |
| 191 | Cl | H | Cl | 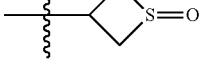 |
| 192 | Cl | F | Cl | 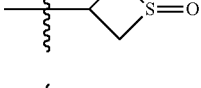 |
| 193 | Cl | Cl | Cl |  |
| 194 | Cl | H | Cl |  |
| 195 | Cl | F | Cl |  |
| 196 | Cl | Cl | Cl | 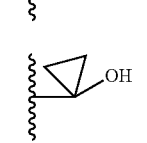 |
| 197 | Cl | H | Cl |  |
| 198 | Cl | F | Cl | 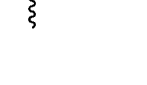 |
| 199 | Cl | Cl | Cl | 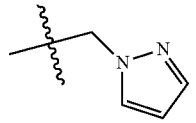 [SMILES: *Cn1cccn1] |
| 200 | Cl | H | Cl | 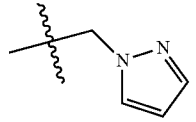 |
| 201 | Cl | F | Cl | 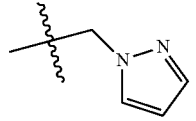 [SMILES: *Cn1cccn1] |
| 202 | Cl | Cl | Cl | 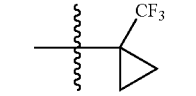 |
| 203 | Cl | H | Cl | 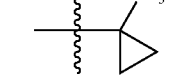 |
| 204 | Cl | F | Cl | 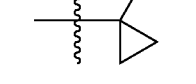 |
| 205 | Cl | Cl | Cl | 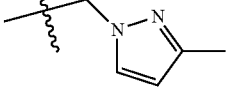 |
| 206 | Cl | H | Cl | 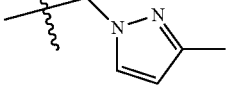 |
| 207 | Cl | F | Cl | 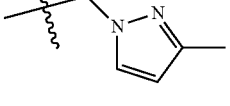 |
| 208 | Cl | Cl | Cl | 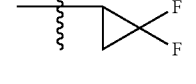 |
| 209 | Cl | H | Cl | 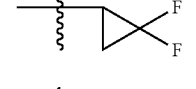 |
| 210 | Cl | F | Cl | 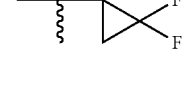 |

TABLE 3-continued

Spirocyclic Isoxazolines of Formula (1.3b)

| Example No. | $R^{1a}$ | $R^{1b}$ | $R^{1c}$ | $R^5$ |
|---|---|---|---|---|
| 211 | Cl | Cl | Cl | 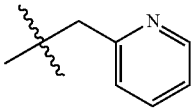 [SMILES: *Cc1ccccn1] |
| 212 | Cl | H | Cl | 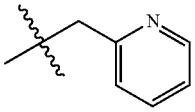 |
| 213 | Cl | F | Cl | 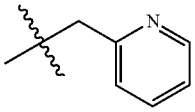 [SMILES: *Cc1ccccn1] |

By the methods described herein, the following dihydropyrazolyl spirocyclic isobenzofurans of Table 4 can be prepared from Formula (1.4b).

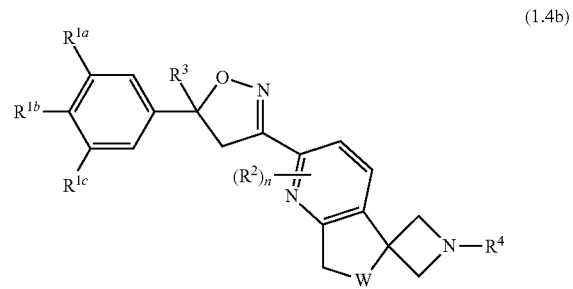

(1.4b)

For Table 4: n is the integer 0; W is O; $R^3$ is $CF_3$; and $R^4$ is $C(O)R^5$

TABLE 4

Spirocyclic Isoxazolines of Formula (1.4b)

| Example No. | $R^{1a}$ | $R^{1b}$ | $R^{1c}$ | $R^5$ |
|---|---|---|---|---|
| 214 | Cl | Cl | Cl | Methyl |
| 215 | Cl | H | Cl | Methyl |
| 216 | Cl | F | Cl | Methyl |
| 217 | Cl | Cl | Cl | Ethyl |
| 218 | Cl | H | Cl | Ethyl |
| 219 | Cl | F | Cl | Ethyl |
| 220 | Cl | Cl | Cl | Propyl |
| 221 | Cl | H | Cl | Propyl |
| 222 | Cl | F | Cl | Propyl |
| 223 | Cl | Cl | Cl | Isobutyl |
| 224 | Cl | H | Cl | Isobutyl |
| 225 | Cl | F | Cl | Isobutyl |
| 226 | Cl | Cl | Cl | $CH_2OH$ |
| 227 | Cl | H | Cl | $CH_2OH$ |
| 228 | Cl | F | Cl | $CH_2OH$ |
| 229 | Cl | Cl | Cl | Cyclopropyl |
| 230 | Cl | H | Cl | Cyclopropyl |
| 231 | Cl | F | Cl | Cyclopropyl |
| 232 | Cl | Cl | Cl | Cyclobutyl |
| 233 | Cl | H | Cl | Cyclobutyl |
| 234 | Cl | F | Cl | Cyclobutyl |
| 235 | Cl | Cl | Cl | $CH_2$-cyclopropyl |
| 236 | Cl | H | Cl | $CH_2$-cyclopropyl |

TABLE 4-continued

Spirocyclic Isoxazolines of Formula (1.4b)

| Example No. | $R^{1a}$ | $R^{1b}$ | $R^{1c}$ | $R^5$ |
|---|---|---|---|---|
| 237 | Cl | F | Cl | $CH_2$-cyclopropyl |
| 238 | Cl | Cl | Cl | $CH_2$-cyclobutyl |
| 239 | Cl | H | Cl | $CH_2$-cyclobutyl |
| 240 | Cl | F | Cl | $CH_2$-cyclobutyl |
| 241 | Cl | Cl | Cl | $CH_2CF_3$ |
| 242 | Cl | H | Cl | $CH_2CF_3$ |
| 243 | Cl | F | Cl | $CH_2CF_3$ |
| 244 | Cl | Cl | Cl | —$CH_2SCH_3$ |
| 245 | Cl | H | Cl | —$CH_2SCH_3$ |
| 246 | Cl | F | Cl | —$CH_2SCH_3$ |
| 247 | Cl | Cl | Cl | —$CH_2S(O)CH_3$ |
| 248 | Cl | H | Cl | —$CH_2S(O)CH_3$ |
| 249 | Cl | F | Cl | —$CH_2S(O)CH_3$ |
| 250 | Cl | Cl | Cl | 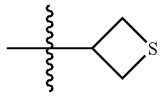 |
| 251 | Cl | H | Cl | 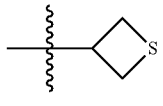 |
| 252 | Cl | F | Cl | 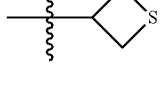 |
| 253 | Cl | Cl | Cl | 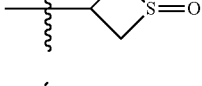 |
| 254 | Cl | H | Cl |  |
| 255 | Cl | F | Cl |  |
| 256 | Cl | Cl | Cl |  |
| 257 | Cl | H | Cl |  |
| 258 | Cl | F | Cl |  |
| 259 | Cl | Cl | Cl | 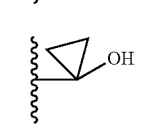 |
| 260 | Cl | H | Cl |  |

TABLE 4-continued

Spirocyclic Isoxazolines of Formula (1.4b)

| Example No. | R1a | R1b | R1c | R5 |
|---|---|---|---|---|
| 261 | Cl | F | Cl | 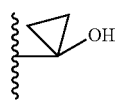 |
| 262 | Cl | Cl | Cl | 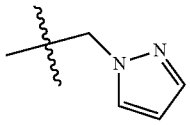 [SMILES: *Cn1cccn1] |
| 263 | Cl | H | Cl | 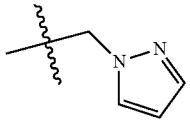 |
| 264 | Cl | F | Cl | 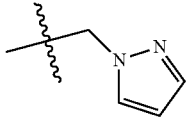 |
| 265 | Cl | Cl | Cl | 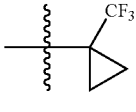 |
| 266 | Cl | H | Cl | 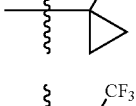 |
| 267 | Cl | F | Cl | 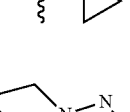 |
| 268 | Cl | Cl | Cl | 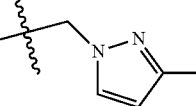 |
| 269 | Cl | H | Cl | 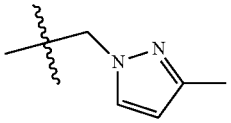 [SMILES: *Cn1ccc(C)n1] |
| 270 | Cl | F | Cl | 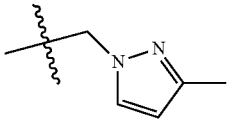 [SMILES: *Cn1ccc(C)n1] |
| 271 | Cl | Cl | Cl | 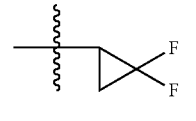 [SMILES: *C1CC1(F)F] |
| 272 | Cl | H | Cl | 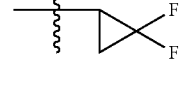 |
| 273 | Cl | F | Cl | 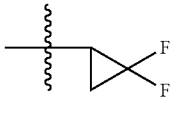 [SMILES: *C1CC1(F)F] |
| 274 | Cl | Cl | Cl | 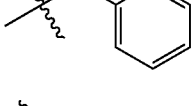 |
| 275 | Cl | H | Cl | 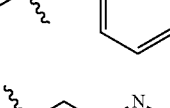 |
| 276 | Cl | F | Cl | 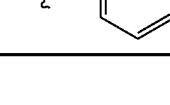 |

Biological Assays

The biological activity of the compounds of the present invention can be tested against hard tick larvae, soft ticks, fleas, and horn flies using the test methods described below.

Flea (*Ctenocephalides felis*) Membrane Feed Assay-Adult

Compounds of the present invention were dissolved in DMSO and aliquots added to citrated bovine blood in membrane covered wells pre-warmed to 37° C. Adult fleas were newly emerged (3-7 days) and unfed. Feeding wells containing approximately 10 adult fleas were placed onto the treated blood wells, and the fleas were allowed to feed on the treated blood for 24 hours. Fleas were observed for knockdown and/or death at 24 hours. Each compound was tested at half-log intervals, and endpoint data was recorded as Minimum Effective Concentration (MEC) in µM. MEC is a subjective visual assessment of organism viability, and is the lowest dose observed to cause mortality≥50%. In this assay, Examples 4, 16, and 17 had an MEC of 0.1 µM; Example 18 had an MEC of 0.3 µM; Examples 2, 3, 5, 6, 13, and 14 had an MEC of 1 µM; Examples 1, 10, and 15 had an MEC of 3 µM; and Examples 7, 8, 9, 11, and 12 had an MEC≥0 µM.

Soft Tick (*Ornithidorus turicata*) Blood Feed Assay

Compounds were dissolved in DMSO and aliquots were added to citrated bovine blood in membrane covered wells warmed to 37° C. 5 nymphs were placed on the membrane, allowed to feed to repletion, and were placed in observation wells. Nymphs were observed for knockdown and/or death at 24 and 72 hours. Endpoint results for subjective visual assessment of organism viability were recorded as $LD_{100}$ (the lowest dose to cause 100% mortality). In this assay, Examples 4, 5, 6, 16, 17, and 18 had an $LD^{100}$ of 0.03 µg/mL; Examples 1, 10, and 13 had an $LD^{100}$ value of 0.1 µg/mL; Examples 2, 3, 11, 12, and 14 had an $LD^{100}$ of 0.3 µg/mL; and Examples 7, 8, 9, and 15 had an $LD^{100}$ of >3 µg/mL.

Mosquito (*Aedes aeqypti*) Larval Assay—1st Instar Larvae

Compounds were dissolved in DMSO and aliquots were spotted to empty wells. First instar larvae and maintenance media were added to the wells to obtain between 8 and 12 larvae per well in the appropriate final assay volume. Larvae were incubated in the treated media at 25° C. for 24 hours. Mosquito larvae motility was measured at 24 hours. Each compound was tested at half-log intervals, and endpoint results were recorded as Minimum Effective Concentration (MEC) in µM. MEC is an objective assessment of organism motility, and is the lowest dose to inhibit motility≥50% of untreated controls. In this assay, Example 16 had an MEC of 0.001 µM; Examples 4, 6, 13, 14, 17, and 18 had an MEC of 0.01 µM; Examples 2, 3, 5, 10, and 15 had an MEC of 0.03 µM; Examples 1 and 12 had an MEC of 0.1 µM; and Examples 7, 8, 9, and 11 had an MEC of 0.3 µM.

We claim:

1. A compound of Formula (1)

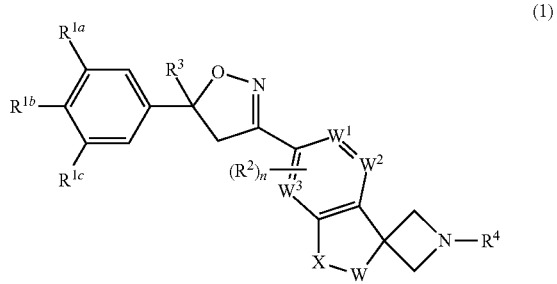

(1)

wherein
- $W^1$, $W^2$, and $W^3$ are each independently C or N;
- X is —S(O)$_p$ or O and W is CH$_2$, or W is —S(O)$_p$ or O and X is CH$_2$; with the proviso that if W or X is O then one of $W^1$, $W^2$, and $W^3$ is N and if $W^1$, $W^2$, and $W^3$ are all C then one of X or W is —S(O)$_p$;
- $R^{1a}$, $R^{1b}$ and $R^{1c}$ are each independently hydrogen, halo, cyano, hydroxyl, nitro, $C_1$-$C_6$alkyl, $C_1$-$C_6$haloalkyl, $C_1$-$C_6$alkoxy, $C_0$-$C_3$alkylC$_3$-$C_6$ cycloalkyl, $C_1$-$C_6$haloalkoxy, —C(O)NH$_2$, —SF$_5$, or
- $R^2$ is halo, cyano, $C_1$-$C_6$alkyl, $C_1$-$C_6$haloalkyl, nitro, hydroxyl, —C(O)NR$^a$R$^b$, $C_2$-$C_6$alkenyl, $C_2$-$C_6$alkynyl, —S(O)R, or —OR;
- $R^3$ is cyano, $C_1$-$C_6$alkyl, $C_1$-$C_6$haloalkyl, —C(O)NR$^a$R$^b$, $C_2$-$C_6$alkenyl, $C_2$-$C_6$alkynyl, $C_2$-$C_6$haloalkenyl, or $C_2$-$C_6$haloalkynyl;
- $R^4$ is hydrogen, $C_1$-$C_6$alkyl, $C_0$-$C_6$alkylC$_3$-$C_6$cycloalkyl, —C(O)R$^5$, —C(S)R$^5$, —C(O)NR$^a$R$^5$, —C(O)C(O)NR$^a$R$^5$, —S(O)$_p$R$^c$, —S(O)$_2$NR$^a$R$^5$, —C(NR$^6$)R$^5$, —C(NR$^6$)NR$^a$R$^5$, $C_0$-$C_6$alkylphenyl, $C_0$-$C_6$alkylheteroaryl, or $C_0$-$C_6$alkylheterocycle;
- $R^5$ is hydrogen, $C_1$-$C_6$alkyl, $C_2$-$C_6$alkenyl, $C_0$-$C_6$alkylC$_3$-$C_6$cycloalkyl, $C_0$-$C_6$alkylphenyl, $C_0$-$C_6$alkylheteroaryl, or $C_0$-$C_6$alkylheterocycle;
- $R^6$ is hydrogen, $C_1$-$C_6$alkyl, hydroxyl, cyano, nitro, —S(O)$_p$R$^c$, or $C_1$-$C_6$alkoxy;
- R is $C_1$-$C_6$alkyl or $C_3$-$C_6$cycloalkyl optionally substituted with at least one halo substituent;
- $R^a$ is hydrogen, $C_1$-$C_6$alkyl, or $C_0$-$C_3$alkylC$_3$-$C_6$cycloalkyl; wherein the alkyl and alkylcycloalkyl is optionally substituted by cyano or at least one halo substituent;
- $R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;
- $R^c$ is $C_1$-$C_6$alkyl, $C_1$-$C_6$haloalkyl, $C_1$-$C_6$haloalkylC$_3$-$C_6$cycloalkyl, $C_0$-$C_3$alkylC$_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R, —SCN, or —C(O)NR$^a$R$^b$;
- each of $R^4$ and $R^5$ $C_1$-$C_6$alkyl or $C_0$-$C_6$alkylC$_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxylC$_1$-$C_6$alkyl-, —S(O)$_p$R$^c$, —SH, —S(O)$_p$NR$^a$R$^b$, —NR$^a$R$^b$, —NR$^a$C(O)R$^b$, —SC(O)R, —SCN, or —C(O)NR$^a$R$^b$; and
- wherein each of $R^4$ and $R^5$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =NR$^6$, hydroxyl, $C_1$-$C_6$alkoxy, $C_1$-$C_6$alkyl, hydroxylC$_1$-$C_6$alkyl-, $C_1$-$C_6$haloalkyl, —SH, —S(O)$_p$R, and $C_1$-$C_6$haloalkoxy;
- n is the integer 0, 1, or 2, and when n is 2, each $R^2$ may be identical or different from each other; and
- p is the integer 0, 1, or 2;

stereoisomers thereof, and veterinary or pharmaceutical acceptable salts thereof.

2. The compound of Formula (1) of claim 1 having Formula (1.1), (1.2), (1.3), or (1.4)

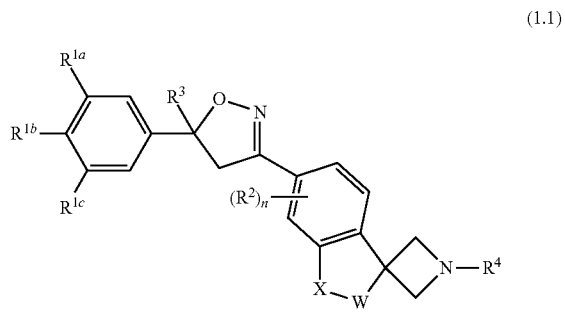

(1.1)

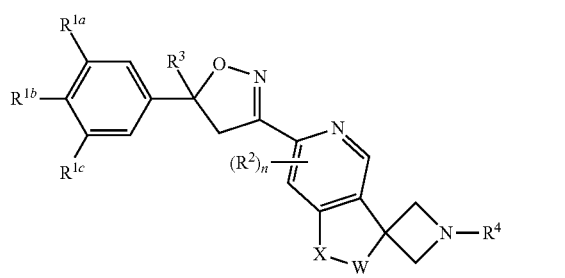

(1.2)

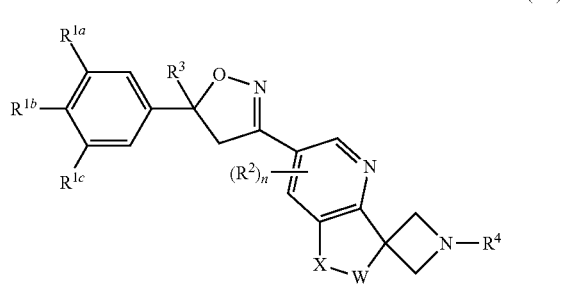

(1.3)

-continued (1.4)

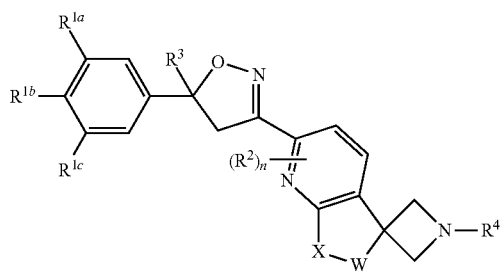

stereoisomers thereof, and veterinary or pharmaceutical acceptable salts thereof.

3. The compound of Formula (1.2) of claim 2 having Formula (1.2b)

(1.2b)

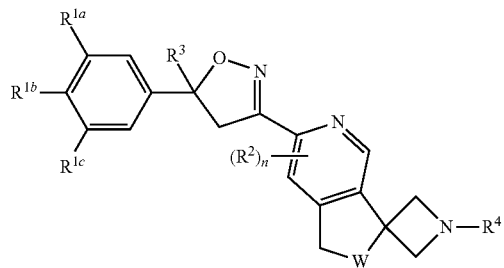

wherein W is O; stereoisomers thereof, and a veterinary or pharmaceutical acceptable salt thereof.

4. The compound of claim 3 wherein
$R^{1a}, R^{1b}$, and $R^{1c}$ are each independently hydrogen, fluoro, chloro, bromo, or $CF_3$;
$R^3$ is $C_1$-$C_6$haloalkyl; and
$R^4$ is —C(O)$R^5$, stereoisomers thereof, and veterinary or pharmaceutical acceptable salts thereof.

5. The compound of Formula (1.3) of claim 2 having Formula (1.3b)

(1.3b)

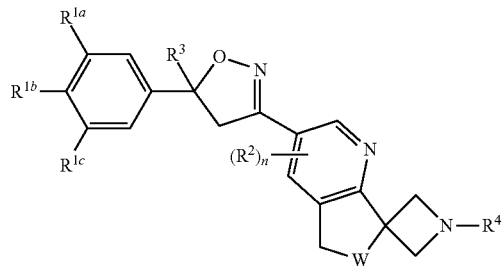

wherein W is O; stereoisomers thereof, and a veterinary or pharmaceutical acceptable salt thereof.

6. The compound of claim 5 wherein
$R^{1a}, R^{1b}$, and $R^{1c}$ are each independently hydrogen, fluoro, chloro, bromo, or $CF_3$;
$R^3$ is $C_1$-$C_6$haloalkyl; and
$R^4$ is —C(O)$R^5$, stereoisomers thereof, and veterinary or pharmaceutical acceptable salts thereof.

7. The compound of Formula (1.4) of claim 2 having Formula (1.4b)

(1.4b)

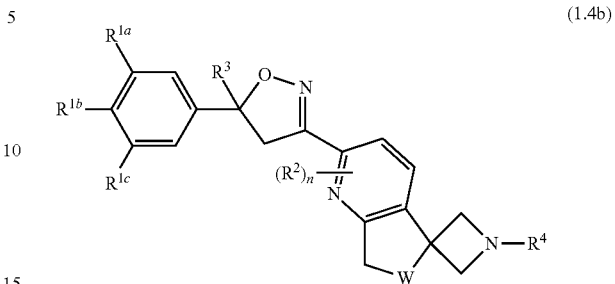

wherein W is O; stereoisomers thereof, and a veterinary or pharmaceutical acceptable salt thereof.

8. A compound of claim 1 selected from the group selected from
3'-[5-(3,5-dichlorophenyl)-5-(trifluoromethyl)-4,5-dihydroisoxazol-3-yl]-1-[(methylsulfonyl)acetyl]-5'H-spiro[azetidin-3,7'-furo[3,4,b]pyridine];
3'-[5-(3,5-dichloro-4-fluorophenyl)-5-(trifluoromethyl)-4,5-dihydroisoxazol-3-yl]-1-[(methylsulfonyl)acetyl]-5'H-spiro[azetidin-3,7'-furo[3,4,b]pyridine];
1-[(methylsulfonyl)acetyl]-3'-[5-(3,4,5-trichlorophenyl)-5-(trifluoromethyl)-4,5-dihydroisoxazol-3-yl]-5'H-spiro[azetidin-3,7'-furo[3,4,b]pyridine];
3'-[5-(3,5-dichloro-4-fluorophenyl)-5-(trifluoromethyl)-4,5-dihydroisoxazol-3-yl]-1-isobutyryl-5'H-spiro[azetidin-3,7'-furo[3,4,b]pyridine];
3'-[5-(3,5-dichlorophenyl)-5-(trifluoromethyl)-4,5-dihydroisoxazol-3-yl]-1-isobutyryl-5'H-spiro[azetidin-3,7'-furo[3,4,b]pyridine];
1-isobutyryl-3'-[5-(3,4,5-trichlorophenyl)-5-(trifluoromethyl)-4,5-dihydroisoxazol-3-yl]-5'H-spiro[azetidin-3,7'-furo[3,4,b]pyridine];
1-(2'-(5-(3,5-dichloro-4-fluorophenyl)-5-(trifluoromethyl)-4,5-dihydroisoxazol-3-yl)-7'H-spiro[azetidine-3,5'-furo[3,4-b]pyridine]-1-yl)-2-(methylsulfonyl)ethanone;
1-(2'-(5-(3,5-dichlorophenyl)-5-(trifluoromethyl)-4,5-dihydroisoxazol-3-yl)-7'H-spiro[azetidine-3,5'-furo[3,4-b]pyridine]-1-yl)-2-(methylsulfonyl)ethanone;
2-(methylsulfonyl)-1-(2'-(5-(3,4,5-trichlorophenyl)-5-(trifluoromethyl)-4,5-dihydroisoxazol-3-yl)-7'H-spiro[azetidine-3,5'-furo[3,4-b]pyridine]-1-yl)ethanone;
1-(2'-(5-(3,5-dichloro-4-fluorophenyl)-5-(trifluoromethyl)-4,5-dihydroisoxazol-3-yl)-7'H-spiro[azetidine-3,5'-furo[3,4-b]pyridine]-1-yl)-2-methylpropan-1-one;
1-(2'-(5-(3,5-dichlorophenyl)-5-(trifluoromethyl)-4,5-dihydroisoxazol-3-yl)-7'H-spiro[azetidine-3,5'-furo[3,4-b]pyridine]-1-yl)-2-methylpropan-1-one;
2-methyl-1-(2'-(5-(3,4,5-trichlorophenyl)-5-(trifluoromethyl)-4,5-dihydroisoxazol-3-yl)-7'H-spiro[azetidine-3,5'-furo[3,4-b]pyridine]-1-yl)propan-1-one;
1-(6'-(5-(3,5-dichloro-4-fluorophenyl)-5-(trifluoromethyl)-4,5-dihydroisoxazol-3-yl)-1'H-spiro[azetidine-3,3'-furo[3,4-c]pyridine]-1-yl)-2-(methylsulfonyl)ethanone;
2-(methylsulfonyl)-1-(6'-(5-(3,4,5-trichlorophenyl)-5-(trifluoromethyl)-4,5-dihydroisoxazol-3-yl)-1'H-spiro[azetidine-3,3'-furo[3,4-c]pyridine]-1-yl)ethanone;
1-(6'-(5-(3,5-dichlorophenyl)-5-(trifluoromethyl)-4,5-dihydroisoxazol-3-yl)-1H-spiro[azetidine-3,3'-furo[3,4-c]pyridine]-1-yl)-2-(methylsulfonyl)ethanone;

1-(6'-(5-(3,5-dichloro-4-fluorophenyl)-5-(trifluorom-ethyl)-4,5-dihydroisoxazol-3-yl)-1'H-spiro[azetidine-3,3'-furo[3,4-c]pyridine]-1-yl)-2-methylpropan-1-one;

2-methyl-1-(6'-(5-(3,4,5-trichlorophenyl)-5-(trifluorom-ethyl)-4,5-dihydroisoxazol-3-yl)-1H-spiro[azetidine-3,3'-furo[3,4-c]pyridine]-1-yl)propan-1-one; and 1-(6'-(5-(3,5-dichlorophenyl)-5-(trifluoromethyl)-4,5-di-hydroisoxazol-3-yl)-1'H-spiro[azetidine-3,3'-furo[3,4-c]pyridine]-1-yl)-2-methylpropan-1-one, stereoisomers thereof, and veterinary or pharmaceutical acceptable salts thereof, or a compound selected from any one of the compounds in Table 1, Table 2, Table 3, or Table 4, stereoisomers thereof, and a veterinary or pharmaceutical acceptable salt thereof.

9. A veterinary composition comprising a compound of Formula 1

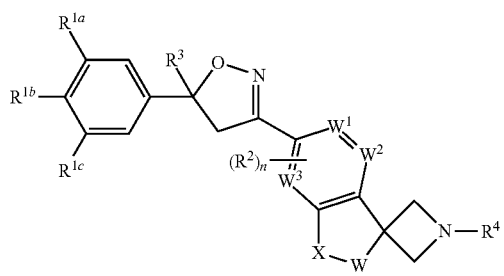

(1)

wherein $W^1$, $W^2$, and $W^3$ are each independently C or N;

X is $-S(O)_p$ or O and W is $CH_2$, or W is $-S(O)_p$ or O and X is $CH_2$; with the proviso that if W or X is O then one of $W^1$, $W^2$, and $W^3$ is N and if $W^1$, $W^2$, and $W^3$ are all C then one of X or W is $-S(O)_p$;

$R^{1a}$, $R^{1b}$, and $R^{1c}$ are each independently hydrogen, halo, cyano, hydroxyl, nitro, $C_1$-$C_6$alkyl, $C_1$-$C_6$haloalkyl, $C_1$-$C_6$alkoxy, $C_0$-$C_3$alkyl$C_3$-$C_6$ cycloalkyl, $C_1$-$C_6$haloalkoxy, $-C(O)NH_2$, $-SF_5$, or $-S(O)_pR$;

$R^2$ is halo, cyano, $C_1$-$C_6$alkyl, $C_1$-$C_6$haloalkyl, nitro, hydroxyl, $-C(O)NR^aR^b$, $C_2$-$C_6$alkenyl, $C_2$-$C_6$alkynyl, $-S(O)_pR$, or $-OR$;

$R^3$ is cyano, $C_1$-$C_6$alkyl, $C_1$-$C_6$haloalkyl, $-C(O)NR^aR^b$, $C_2$-$C_6$alkenyl, $C_2$-$C_6$alkynyl, $C_2$-$C_6$haloalkenyl, or $C_2$-$C_6$haloalkynyl;

$R^4$ is hydrogen, $C_1$-$C_6$alkyl, $C_0$-$C_3$alkyl$C_3$-$C_6$cycloalkyl, $-C(O)R^5$, $-C(S)R^5$, $-C(O)NR^aR^5$, $-C(O)C(O)NR^aR^5$, $-S(O)_pR^c$, $-S(O)_2NR^aR^5$, $-C(NR^6)R^5$, $-C(NR^6)NR^aR^5$, $C_0$-$C_6$alkylphenyl, $C_0$-$C_6$alkylheteroaryl, or $C_0$-$C_6$alkylheterocycle;

$R^5$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;

$R^6$ is hydrogen, $C_1$-$C_6$alkyl, hydroxyl, cyano, nitro, $-S(O)_pR^c$, or $C_1$-$C_6$alkoxy;

R is $C_1$-$C_6$alkyl or $C_3$-$C_6$cycloalkyl optionally substituted with at least one halo substituent;

$R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or $-S(O)_pR$;

$R^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, $-S(O)_pR$, $-SH$, $-S(O)_pNR^aR^b$, $-NR^aR^b$, $-NR^aC(O)R^b$, $-SC(O)R$, $-SCN$, or $-C(O)NR^aR^b$;

each of $R^4$ and $R^5$ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, $-S(O)_pR^c$, $-SH$, $-S(O)_pNR^aR^b$, $-NR^aR^b$, $-NR^aC(O)R^b$, $-SC(O)R$, $-SCN$, or $-C(O)NR^aR^b$; and wherein each of $R^4$ and $R^5$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, $=S$, $=NR^6$, hydroxyl, $C_1$-$C_6$alkoxy, $C_1$-$C_6$alkyl, hydroxyl$C_1$-$C_6$alkyl-, $C_1$-$C_6$haloalkyl, $-SH$, $-S(O)_pR$, and $C_1$-$C_6$haloalkoxy;

n is the integer 0, 1, or 2, and when n is 2, each $R^2$ may be identical or different from each other; and p is the integer 0, 1, or 2;

stereoisomers thereof, and veterinary or pharmaceutical acceptable salts thereof.

10. The veterinary composition of claim 9 further comprising at least one veterinary or pharmaceutical acceptable carrier.

11. The veterinary composition of claim 10 further comprising at least one additional veterinary agent.

12. The veterinary composition of claim 11 wherein said additional veterinary agent is selected from the group consisting of abamectin, ivermectin, avermectin, moxidectin, emamectin, eprinomectin, selamectin, doramectin, nemadectin, albendazole, cambendazole, fenbendazole, flubendazole, mebendazole, oxfenbendazole, oxibendazole, parbendazole, tetramisole, levamisole, pyrantel pamoate, oxantel, morantel, indoxacarb, closantel, triclabendazole, clorsulon, refoxanide, niclosamide, praziquantel, epsiprantel, 2-desoxoparaherquamide, monepantel, pyripole, pyrafluprole, lufenuron, spiromesifen, tebufenozide, spinosad, spinetoram, imidacloprid, dinotefuran, metaflumizone, thibendiamide, chlorantraniliprole, indoxacarb, pyridalyl, pyrimidifen, pyrifluquinazon, milbemycin oxime, milbemycin, demiditraz, amitraz, fipronil, methoprene, hydroprene, kinoprene, permethrin, and pyrethrin, or mixtures thereof.

13. A method for the treatment of a parasitic infection or infestation in an animal comprising administering to said animal in need of such treatment an effective amount of a compound of Formula 1

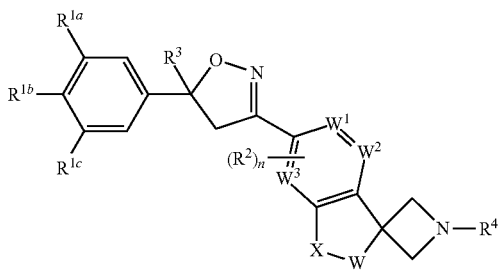

(1)

wherein
$W^1$, $W^2$, and $W^3$ are each independently C or N;
X is —$S(O)_p$ or O and W is $CH_2$, or W is —$S(O)_p$ or O and X is $CH_2$; with the proviso that if W or X is O then one of $W^1$, $W^2$, and $W^3$ is N and if $W^1$, $W^2$, and $W^3$ are all C then one of X or W is —$S(O)_p$;
$R^{1a}$, $R^{1b}$, and $R^{1c}$ are each independently hydrogen, halo, cyano, hydroxyl, nitro, $C_1$-$C_6$alkyl, $C_1$-$C_6$haloalkyl, $C_1$-$C_6$alkoxy, $C_0$-$C_3$alkyl$C_3$-$C_6$ cycloalkyl, $C_1$-$C_6$haloalkoxy, —$C(O)NH_2$, —$SF_5$, or —$S(O)_pR$;
$R^2$ is halo, cyano, $C_1$-$C_6$alkyl, $C_1$-$C_6$haloalkyl, nitro, hydroxyl, —$C(O)NR^aR^b$, $C_2$-$C_6$alkenyl, $C_2$-$C_6$alkynyl, —$S(O)_pR$, or —OR;
$R^3$ is cyano, $C_1$-$C_6$alkyl, $C_1$-$C_6$haloalkyl, —$C(O)NR^aR^b$, $C_2$-$C_6$alkenyl, $C_2$-$C_6$alkynyl, $C_2$-$C_6$haloalkenyl, or $C_2$-$C_6$haloalkynyl;
$R^4$ is hydrogen, $C_1$-$C_6$alkyl, $C_0$-$C_6$alkyl$C_3$-$C_6$cycloalkyl, —$C(O)R^5$, —$C(S)R^5$, —$C(O)NR^aR^5$, —$C(O)C(O)NR^aR^5$, —$S(O)_pR^c$, —$S(O)_2NR^aR^5$, —$C(NR^6)R^5$, —$C(NR^6)NR^aR^5$, $C_0$-$C_6$alkylphenyl, $C_0$-$C_6$alkylheteroaryl, or $C_0$-$C_6$alkylheterocycle;
$R^5$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;
$R^6$ is hydrogen, $C_1$-$C_6$alkyl, hydroxyl, cyano, nitro, —$S(O)_pR^c$, or $C_1$-$C_6$alkoxy;
R is $C_1$-$C_6$alkyl or $C_3$-$C_6$cycloalkyl optionally substituted with at least one halo substituent;
$R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;
$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —$S(O)_pR$;
$R^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —$S(O)_pR$, —SH, —$S(O)_pNR^aR^b$, —$NR^aR^b$, —$NR^aC(O)R^b$, —SC(O)R, —SCN, or —$C(O)NR^aR^b$;
each of $R^4$ and $R^5$ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, —$S(O)_pR^c$, —SH, —$S(O)_pNR^aR^b$, —$NR^aR^b$, —$NR^aC(O)R^b$, —SC(O)R, —SCN, or —$C(O)NR^aR^b$; and
wherein each of $R^4$ and $R^5$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =$NR^6$, hydroxyl, $C_1$-$C_6$alkoxy, $C_1$-$C_6$alkyl, hydroxyl$C_1$-$C_6$alkyl-, $C_1$-$C_6$haloalkyl, —SH, —$S(O)_pR$, and $C_1$-$C_6$haloalkoxy;
n is the integer 0, 1, or 2, and when n is 2, each $R^2$ may be identical or different from each other; and
p is the integer 0, 1, or 2;
stereoisomers thereof, and veterinary or pharmaceutical acceptable salts thereof.

14. The method of claim 13 wherein said animal is a companion animal or livestock and the compound is administered topically, orally, or subcutaneously.

15. The method of claim 14 wherein the companion animal is a dog, cat, or horse.

16. The method of claim 14 wherein livestock is cattle.

17. The method of claim 14 wherein the compound is administered topically.

18. The method of claim 14 wherein the compound is administered orally.

19. The method of claim 14 wherein the compound is administered subcutaneously.

* * * * *